United States Patent
Hinkle

(10) Patent No.: US 10,883,107 B2
(45) Date of Patent: Jan. 5, 2021

(54) POLYNUCLEOTIDE AGENTS TARGETING FACTOR XII (HAGEMAN FACTOR) (F12) AND METHODS OF USE THEREOF

(71) Applicant: Alnylam Pharmaceuticals, Inc., Cambridge, MA (US)

(72) Inventor: Gregory Hinkle, Plymouth, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/068,444

(22) PCT Filed: Jan. 6, 2017

(86) PCT No.: PCT/US2017/012420
§ 371 (c)(1),
(2) Date: Jan. 17, 2019

(87) PCT Pub. No.: WO2017/120397
PCT Pub. Date: Jul. 13, 2017

(65) Prior Publication Data
US 2019/0024088 A1  Jan. 24, 2019

Related U.S. Application Data

(60) Provisional application No. 62/276,279, filed on Jan. 8, 2016.

(51) Int. Cl.
*A61K 48/00* (2006.01)
*C07H 21/04* (2006.01)
*C12N 15/113* (2010.01)
*A61K 9/51* (2006.01)
*A61K 31/58* (2006.01)
*A61K 31/585* (2006.01)
*A61K 31/7088* (2006.01)

(52) U.S. Cl.
CPC ........ *C12N 15/1137* (2013.01); *A61K 9/5123* (2013.01); *A61K 31/58* (2013.01); *A61K 31/585* (2013.01); *A61K 31/7088* (2013.01); *C12N 15/113* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/351* (2013.01)

(58) Field of Classification Search
CPC .............................. C12N 15/111; C12N 15/113
See application file for complete search history.

(56) References Cited

U.S. PATENT DOCUMENTS 9,803,205 B2  10/2017 Kanner et al.
2008/0113351 A1  5/2008 Naito et al.
2011/0178283 A1  7/2011 Rigoutsos et al.
2015/0368642 A1* 12/2015 Alb K .................... A61K 47/64
                                                    514/44 A
2016/0272970 A1*  9/2016 Rozema ................ C12N 15/111
2019/0264210 A1*  8/2019 Kole ....................... C12N 15/87

FOREIGN PATENT DOCUMENTS

| CN | 102600471 A | 7/2012 |
| EP | 1752536 A1 | 2/2007 |
| WO | WO-2007059966 A1 | 5/2007 |
| WO | WO-2007130604 A2 | 11/2007 |
| WO | WO-2009053050 A1 | 4/2009 |
| WO | WO-2012170947 A2 | 12/2012 |
| WO | WO-2016149331 A2 | 9/2016 |
| WO | WO-2016179342 A2 | 11/2016 |

OTHER PUBLICATIONS

Vickers et al. (The Journal of Biological Chemistry, vol. 278, No. 9, 7108-7118, 2003).*
EMBL Database Accession No. FW736821; Sequence 143347 from PCT Publication No. WO 2005/116204.
Cai et al., "Factor XII full and partial null in rat confers robust antithrombotic efficacy with no bleeding," Blood Coagulation & Fibrinolysis, 2015, 26:893-902.
International Search Report from PCT/US2016/030876 dated Nov. 28, 2016.
Papageorgiou et al. "Coagulation Factor XIIa-kinin-mediated contribution to hypertension of chronic kidney disease," Journal of Hypertension, 2014, 32(7):1523-1533.
International Search Report from PCT/US2017/012420 dated Mar. 1, 2017.
European Search Report from EP Application No. 17736380.1 dated Jun. 18, 2019.
Reynolds et al., "Rational siRNA design for RNA interference," Nature Biotechnology, vol. 22, pp. 326-330, 2004.
Allerson et al., "Fully 2'-Modified Oligonucleotide Duplexes with Improved in Vitro Potency and Stability Compared to Unmodified Small Interfering RNA", J. Med. Chem.48(4):901-904, 2005.
U.S. Appl. No. 16/421,745, filed May 24, 2019, Not Yet Assigned, Pending.
PCT/US2018/040967, Jul. 6, 2018, WO 2019/010342, Published.

* cited by examiner

Primary Examiner — Amy H Bowman
(74) Attorney, Agent, or Firm — McCarter & English, LLP; Maria Laccotripe Zacharakis; Deborah L. Nagle

(57) ABSTRACT

The invention relates to polynucleotide agents targeting Factor XII (F12) gene, and methods of using such polynucleotide agents to inhibit expression of Factor XII and to treat subjects having a Factor XII-associated disease, e.g., heredity angioedema (HAE), prekallikrein deficiency, malignant essential hypertension, hypertension, end stage renal disease, or Fletcher Factor Deficiency.

18 Claims, No Drawings
Specification includes a Sequence Listing.

SEQUENCE LISTING

<160> NUMBER OF SEQ ID NOS: 378

<210> SEQ ID NO 1
<211> LENGTH: 2060
<212> TYPE: DNA
<213> ORGANISM: Homo sapiens

<400> SEQUENCE: 1

| | | | | | | |
|---|---|---|---|---|---|---|
| ctattgatct | ggactcctgg | ataggcagct | ggaccaacgg | acggatgcca | tgagggctct | 60 |
| gctgctcctg | gggttcctgc | tggtgagctt | ggagtcaaca | ctttcgattc | caccttggga | 120 |
| agcccccaag | gagcataagt | acaaagctga | agagcacaca | gtcgttctca | ctgtcaccgg | 180 |
| ggagccctgc | cacttcccct | tccagtacca | ccggcagctg | taccacaaat | gtacccacaa | 240 |
| gggccggcca | ggcctcagc | cctggtgtgc | taccaccccc | aactttgatc | aggaccagcg | 300 |
| atggggatac | tgtttggagc | caagaaagt | gaaagaccac | tgcagcaaac | acagcccctg | 360 |
| ccagaaagga | gggacctgtg | tgaacatgcc | aagcggcccc | cactgtctct | gtccacaaca | 420 |
| cctcactgga | aaccactgcc | agaaagagaa | gtgctttgag | cctcagcttc | tccggttttt | 480 |
| ccacaagaat | gagatatggt | atagaactga | gcaagcagct | gtggccagat | gccagtgcaa | 540 |
| gggtcctgat | gcccactgcc | agcggctggc | cagccaggcc | tgccgcacca | acccgtgcct | 600 |
| ccatggggt | cgctgcctag | aggtggaggg | ccaccgcctg | tgccactgcc | cggtgggcta | 660 |
| caccggagcc | ttctgcgacg | tggacaccaa | ggcaagctgc | tatgatggcc | gcgggctcag | 720 |
| ctaccgcggc | ctggccagga | ccacgctctc | gggtgcgccc | tgtcagccgt | gggcctcgga | 780 |
| ggccacctac | cggaacgtga | ctgccgagca | agcgcggaac | tggggactgg | gcggccacgc | 840 |
| cttctgccgg | aacccggaca | acgacatccg | ccgtgtggc | ttcgtgctga | accgcgaccg | 900 |
| gctgagctgg | gagtactgcg | acctggcaca | gtgccagacc | ccaacccagg | cggcgcctcc | 960 |
| gaccccggtg | tccctaggc | ttcatgtccc | actcatgccc | cgcagccgg | caccgccgaa | 1020 |
| gcctcagccc | acgacccgga | ccccgcctca | gtcccagacc | ccgggagcct | tgccggcgaa | 1080 |
| gcgggagcag | ccgccttccc | tgaccaggaa | cggcccactg | agctgcgggc | agcggctccg | 1140 |
| caagagtctg | tcttcgatga | cccgcgtcgt | tggcgggctg | gtggcgctac | gcggggcgca | 1200 |
| ccctacatc | gccgcgctgt | actggggcca | cagtttctgc | gccggcagcc | tcatcgcccc | 1260 |
| ctgctgggtg | ctgacggccg | ctcactgcct | gcaggaccgg | cccgcacccg | aggatctgac | 1320 |
| ggtggtgctc | ggccaggaac | gccgtaacca | cagctgtgag | ccgtgccaga | cgttggccgt | 1380 |
| gcgctcctac | cgcttgcacg | aggccttctc | gcccgtcagc | taccagcacg | acctggctct | 1440 |
| gttgcgcctt | caggaggatg | cggacggcag | ctgcgcgctc | ctgtcgcctt | acgttcagcc | 1500 |
| ggtgtgcctg | ccaagcggcg | ccgcgcgacc | ctccgagacc | acgctctgcc | aggtggccgg | 1560 |
| ctggggccac | cagttcgagg | gggcggagga | atatgccagc | ttcctgcagg | aggcgcaggt | 1620 |
| accgttcctc | tccctggagc | gctgctcagc | cccggacgtg | cacggatcct | ccatcctccc | 1680 |
| cggcatgctc | tgcgcagggt | tcctcgaggg | cggcaccgat | gcgtgccagg | gtgattccgg | 1740 |
| aggcccgctg | gtgtgtgagg | accaagctgc | agagcgccgg | ctcaccctgc | aaggcatcat | 1800 |
| cagctgggga | tcgggctgtg | gtgaccgcaa | caagccaggc | gtctacaccg | atgtggccta | 1860 |
| ctacctggcc | tggatccggg | agcacaccgt | ttcctgattg | ctcaggact | catctttccc | 1920 |
| tccttggtga | ttccgcagtg | agagagtggc | tggggcatgg | aaggcaagat | tgtgtcccat | 1980 |
| tcccccagtg | cggccagctc | cgcgccagga | tggcgcagga | actcaataaa | gtgctttgaa | 2040 |
| aatgctgaga | aaaaaaaaa | | | | | 2060 |

<210> SEQ ID NO 2
<211> LENGTH: 2198
<212> TYPE: DNA
<213> ORGANISM: Macaca fascicularis

<400> SEQUENCE: 2

| | | | | | |
|---|---|---|---|---|---|
| ttcctgactc | aagtccagag | cttccctacc | ttgcttctaa | ggtgaccaag | gaagtcagtc | 60 |
| cacttggctt | tccataaaca | gcctgtgccc | caccaggctc | aggggggcag | cttgaccaat | 120 |
| ccctatttcc | aagacctttg | gccaacccta | ttgatctgga | ctcctgggca | gacagttgga | 180 |
| ccaacggaca | gacgccatga | gggctctgct | gctcatgggg | ttcctgctgg | tgagcctgga | 240 |
| gtcaacactt | tcgattccac | cttggaaagc | gcccaaggag | cataagtaca | aagctgaaga | 300 |
| gcacacagtc | gttctcactg | tcaccgggga | gccctgccac | ttccccttcc | agtaccaccg | 360 |
| gcggctgtac | cacaaatgta | cccacaaggg | ccggccaggc | cctcagacct | ggtgtgctac | 420 |
| caccccctaac | tttgatgagg | accagcgctg | gggatactgt | gtggagccca | agaaagtgaa | 480 |
| agaccactgc | agtaaacaca | gcccctgcca | gaaaggggg | acctgtgtga | acacgctgag | 540 |
| tggcacccac | tgtctctgtc | cacaacacct | cactgggaac | cactgccaga | gagaagtg | 600 |
| ctttgagcct | cagcttctcc | ggttttcca | cgagaatgag | atatggtata | gatctgagca | 660 |
| agcagctgtg | gccagatgcc | agtgcaaggg | tcctgatgcc | cactgccagc | ggctggccag | 720 |
| ccaggcctgc | cgcaccaacc | cgtgcctcca | tggggtcgc | tgcctagagg | tggagggcca | 780 |
| ccgcctgtgc | cactgccccg | tgggctacac | cggacccttc | tgcgacttgg | acaccaaggc | 840 |
| gagctgctat | gatggccgcg | ggctcagcta | ccgcggcctg | gccaggacca | cgctctcggg | 900 |
| tgcgccctgt | cagccgtgga | cctcggaggc | cacctactgg | aacgtgacgg | ccgagcaagc | 960 |
| gcggaactgg | ggactgggcg | ccacgcctt | ctgccggaac | ccggacaacg | acatccgccc | 1020 |
| gtggtgcttc | gtgctgatcg | gcgacaggct | aagctgggag | tactgcgacg | tggcacagtg | 1080 |
| ccaggcccca | acccaggcgg | cgcctccgac | gccggtgtcc | cctgggcttc | atgtcccact | 1140 |
| catgcccccg | cagccggcac | cgccgaagct | tcagcccacg | acccggaccc | cgcctcagtc | 1200 |
| ccagacccccg | ggagccttgc | cagtgaagcg | ggagcagccg | cctcgcctga | cccggaacgg | 1260 |
| ctcagtgagc | tgcgggcagc | ggctccgcaa | gagtctgtct | tcgatgaccc | gcgtcgttgg | 1320 |
| cgggctggtg | gcgctacgcg | gggcgcaccc | ctacatcgcc | gcgctgtact | ggggccacag | 1380 |
| tttctgcgcc | ggcagcctca | tcgcccctg | ctgggtgctg | acggccgctc | actgcctgca | 1440 |
| ggaccggccg | gcacccgagg | atctgacggt | agtactcggc | caggaacgcc | ataaccacag | 1500 |
| ctgtgaacag | tgccagactc | tggccgtgcg | ctcctaccgc | ttgcacgagg | ccttctcgcc | 1560 |
| cgacagctac | cagcacgacc | tggctctgtt | gcgccttcag | gaggatgcgg | acggcagctg | 1620 |
| cgcgctcctg | tcgccttacg | ttcagccggt | gtgcctgcca | agcggcgccg | cgcgaccctc | 1680 |
| cgagcccgcg | ctctgccagg | tggctggctg | gggccaccag | ttcgaggggg | cggaggaata | 1740 |
| ttccagcttc | ctgcaggagg | cgcaggtacc | cttcctctcc | ctggagagct | gctcagcacc | 1800 |
| ggaggtgcac | ggagcctcca | tcctcccgg | catgctctgc | gcagggttcc | tcgagggcgg | 1860 |
| caccgatgca | tgccagggtg | attccggagg | cccgctggt | tgtgaggacc | aagccgcaga | 1920 |
| gcgccggctc | accctgcaag | gcatcatcag | ctggggatcg | ggctgtggtg | accgcaacaa | 1980 |
| gccaggcgtc | tacaccgatg | tggcctacta | cctggcctgg | atccgggagc | acaccgcttc | 2040 |
| ctgattgctc | agggactcat | ctttcccctcc | tcggtgattc | cgcagtggga | gactggctgg | 2100 |

```
ggcatggaag gcaaaattgt gtcccattcc cccaatgcgg ccagctccgc gccaggatgg     2160
cgcaggaact caataaagtg ctttgaaaat gctgagaa                             2198

<210> SEQ ID NO 3
<211> LENGTH: 1971
<212> TYPE: DNA
<213> ORGANISM: Mus musculus

<400> SEQUENCE: 3
actcctgggc aggcagcggg gccatcggca gacgccatga cggctctgtt gttcctgggg      60
tctctgctga tgagtctgga tctgacactt tcggctccac catggaaaga ctccaagaaa     120
tttaaggacg cacctgatgg gcccacagtg ttctcactg tggatgggag ctctgccat      180 tttccctttc agtaccaccg tcagctacac cacaaatgca tccacaaaag gcggccaggc     240
tcccgcccct ggtgtgctac cacccccaac tttgatgaag atcagcaatg gggatactgc     300
ttggagccca agaaagtgaa agaccattgc agcaaacaca acccgtgcca caaaggaggg     360
acatgtatca cacccccaa tgggccacac tgtctctgcc ctgaacacct cactgggaaa     420
cattgccaga agagaaatg ctttgagcct cagcttctca agttcttcca cgagaatgag     480
ctatggttta aacggggcc aggaggtgtg gccaggtgcg agtgcaaagg ttctgaggct     540
cactgcaagc cggtggccag ccaggcctgc agcatcaatc cgtgccttaa tggggcagc     600 tgcctcctcg tggaggacca cccactgtgc cgttgcccta caggctacac tggatatttt     660
tgcgacttgg accctttgggc gacctgctat gaaggcaggg ggctcagcta ccggggccag     720
gctgaaacta cgcaatcggg tgcgccatgt cagcggtgga ccgtggaggc cacctaccgg     780
aacatgactg agaagcaagc gctaagctgg ggcctgggcc accacgcatt tgccggaac     840 ccagataatg acacacgtcc atggtgcttc gtctggagtg cgacaggct gagctgggac     900 tattgcggcc tggagcagtg ccagacgcca acgtttgcac ctctagttgt ccctgagagt     960
caggaggagt ccccgtccca ggcaccatct ctgtcccatg caccaaatga ctcgaccgat    1020
catcagactt ctctgtccaa gaccaacacg atgggctgcg acagaggtt ccgcaaggga    1080 ctgtcctcgt tcatgcgcgt ggtgggcgga ctagtggctc tgcctgggtc gcacccctac    1140
atcgctgcac tgtactgggg taacaacttc tgcgcgggca gtctcatcgc ccctgttgg    1200 gtgctgaccg cggctcactg cctgcagaat cggccagcgc ccgaggaact gacagtggta    1260
cttggtcaag atcgccacaa ccagagctgc gagtggtgcc agactctggc tgtgcgctcc    1320
taccgccttc acgagggctt ctcctccatc acctaccagc acgacttggc tctgctgcgc    1380
ctgcaggaaa gcaaaaccaa cagttgcgcg atcctgtcac ctcacgttca gcctgtgtgt    1440
ctacccagcg gcgcggcccc accctctgag acagtgctct gcgaggtggc cggctggggt    1500
caccagttcg agggggctga agaatactcc accttcctgc aggaggcaca ggttccctt    1560 atcgccctgg atcgctgctc caactctaac gtgcacggag acgccattct ccctgggatg    1620 cttttgcgctg gcttcttgga gggaggcacc gatgcctgcc agggtgactc cgggggccct    1680
ctggtgtgtg aggaaggaac tgcagaacat cagctcaccc tgcgcggagt catcagctgg    1740
ggctccggct gtggtgaccg caacaagccc ggagtctaca cagacgtggc caactacctg    1800
gcttggatcc agaagcatat tgcttcataa ctaaccaggc tttatccttc cctccttgtg    1860
tgctccttgg gatgggacga tgaatgtggc atgctgggtc acagtgaagc tagtgccccg    1920
acactggggg cacagaaact caataaagtg ctttgaaaac gttcctcaga a             1971
```

<210> SEQ ID NO 4
<211> LENGTH: 2128
<212> TYPE: DNA
<213> ORGANISM: Rattus norvegicus

<400> SEQUENCE: 4

```
caggaaccca tctcggtact ctgcttccac cagccttgcc ctgctcacga gggttcgacg      60
gcgctgttct tctgggcttt ctgtgaagtc tgtgctcctc aggcccagga gggagcttaa     120
ccaatctcca cctctgaggt ttctgagacc tttgcccaca tctattgatc cttactctgg     180
ggcaggcagc tgggccattg gcggacgcca tgacggctct gttgttcctg ggtctctgc      240
tgatgagtct ggacttgaca ctttcggcgc accgtggaa gtccaaggag ttcaaggacg      300
gagctggcga tccctctgtg gttctcactg tggacgggaa gctctgccac tttcccttc      360
agtaccaccg tcgcctgtac cacaaatgca tccacaaagg acagccaggc tccaggccct     420
ggtgtgctac caccccaac tttgacgagg accagcaatg gggatactgc ttggagccca     480
agaaagtgaa agaccattgc agcaaacaca gcccctgcca caaggaggg acgtgtgtca      540
acacccccaa cggcccgcac tgtctctgcc ctgaacacct caccgggaaa cattgccaga     600
gagagaaatg ctttgagtct cagctcctca agttcttcca tgagaatgag atatggttta     660
gaactgggcc aggaggtgtg gccaggtgcc agtgcaaagg tcctcaggct gtttgcaagc     720
tgctgaccag tcaggtttgc agggtcaatc cgtgccttaa tggaggcacc tgcctcctcg     780
tggaggacca ccgactgtgc cactgccctg caggctatgc cggaccttt tgcgacttag      840
accttaaggc gacttgctac gaagacaggg gtctcagcta ccggggccag gctaaaacta     900
ctctgtcggg tgcaccatgt cagcggtggg cctcggaggc cacctaccgg aacatgactg     960
agacgcaagc tctaagctgg ggcctgggcc accacgcatt ctgccggaac ccagataatg    1020
acacacgtcc atggtgctac gtctggagtg gcgacaggct gagctgggac tactgcgacc    1080
tggaacagtg ccagatgcca acgctcacat ctccggtttc ccctgagagt cacgacatgc    1140
tgaagccccg gcctcccata ttgcagatgc ctcagttccc gtctctgtcc gatgcactag    1200
acaactcgac ccgtaatcag aatgttgtgt ccaggaccag tacggtggtc tgcggacaga    1260
ggtttcgcaa gcgactgtcc tcgctcaggc gcgtggtggg cggactagtg gctctgcctg    1320
gatcgcatcc ctacatcgct gcactgtact ggggcgacag cttctgcgca ggcagtctca    1380
tcgacccctg ctgggtgctg accgctgctc actgcttgca gaaacggcca gcgcccgagg    1440
aactgacagt ggtacttggt caagatcgcc ataaccagag ctgcgagagg tgccagactc    1500
tggctgtgca ctcctaccgc cttcacgagg gcttctcttc caaaacctac cagcatgatt    1560
tggctctgct gcgcctgcgg gggaggaaaa acagctgcgc gatcttgtcg cctcatgtcc    1620
agccggtgtg tctgcccagc agcgcggcc caccctctga cagtgctc tgcgaggtgg      1680
ccggctgggg tcatcagttc gagggggctg aagaatacgc cacctttctg caggaggcac    1740
aggtacccct tcatctccctg gatcgctgct ccagctctaa cgtgcacgga gacgccatcc    1800
tgcctgggat gcttgtgct ggcttcttgg agggaggcgc cgatgcctgt cagggtgact      1860
ccggggtcc tctggtatgt gatgaaggag ttacagagcg tcagctcacc ctgcgaggag    1920
tcatcagctg gggctccggc tgtggtgacc ggaacaagcc cggggtctac actgacgtgg    1980
ccaattacct ggattggatc caggagcata ctgctttcta agtaaccagg gtcggtcctt    2040
gcgaagctag tggctgggcc ccagggcacac agaaactcaa taaagtgctt tgaaaacgtt    2100
aaaaaaaaaa aaaaaaaaaa aaaaaaaa                                       2128
```

<210> SEQ ID NO 5
<211> LENGTH: 16
<212> TYPE: PRT
<213> ORGANISM: Unknown
<220> FEATURE:
<223> OTHER INFORMATION: Description of Unknown:
      RFGF peptide

<400> SEQUENCE: 5

Ala Ala Val Ala Leu Leu Pro Ala Val Leu Leu Ala Leu Leu Ala Pro
1               5                   10                  15

<210> SEQ ID NO 6
<211> LENGTH: 11
<212> TYPE: PRT
<213> ORGANISM: Unknown
<220> FEATURE:
<223> OTHER INFORMATION: Description of Unknown:
      RFGF analogue peptide

<400> SEQUENCE: 6

Ala Ala Leu Leu Pro Val Leu Leu Ala Ala Pro
1               5                   10

<210> SEQ ID NO 7
<211> LENGTH: 13
<212> TYPE: PRT
<213> ORGANISM: Human immunodeficiency virus

<400> SEQUENCE: 7

Gly Arg Lys Lys Arg Arg Gln Arg Arg Arg Pro Pro Gln
1               5                   10

<210> SEQ ID NO 8
<211> LENGTH: 16
<212> TYPE: PRT
<213> ORGANISM: Drosophila sp.

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
agcugccuat ccaggagucc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
ccguuggtcc agctgccuau                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
auggcatccg tccgtugguc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
agcagagccc tcatggcauc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
accccaggag cagcagagcc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
accagcagga accccaggag                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
acuccaagct caccagcagg                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
cgaaagtgtt gactccaagc                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ccaaggtgga atcgaaagug                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18 uggggggcttc ccaaggugga                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
acuuatgctc cttgggggcu                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 20
cuucagcttt gtactuaugc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
acugugtgct cttcagcuuu                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
acagugagaa cgactgugug                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
uccccggtga cagtgagaac                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
aguggcaggg ctccccggug                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 25
acuggaaggg gaagtggcag					20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
gcugccggtg gtactggaag					20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
uuguggtaca gctgccggug					20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
ugugggtaca tttgtgguac					20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
uggccggccc ttgtggguac					20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
    Synthetic oligonucleotide

<400> SEQUENCE: 30
ggcugagggc ctggccggcc                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 31
guagcacacc agggcugagg                                            20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 32
aguugggggt ggtagcacac                                            20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 33
ccugatcaaa gttgggggug                                            20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 34
ccccatcgct ggtccugauc                                            20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide

<400> SEQUENCE: 35
aaacagtatc cccatcgcug                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ucuugggctc caaacaguau                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37 uggctttca ctttcuuggg                                                     20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
guuugctgca gtggtcuuuc                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
aggggctgtg tttgcugcag                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
       oligonucleotide
<220> FEATURE:
<223> OTHER INFORMATION: Description of Combined DNA/RNA Molecule:
      Synthetic oligonucleotide

<400> SEQUENCE: 40
cuccuuucug gcaggggcug                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
acacaggucc cuccuuucug                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
uuggcaugtt cacacagguc                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
agugggggcc gcttggcaug                                                   20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ggacagagac agtgggggcc                                                   20

<210> SEQ ID NO 45
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ugaggtgttg tggacagaga                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
aguggtttcc agtgaggugu                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
ucucuttctg gcagtgguuu                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
caaagcactt ctcttucugg                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
gaagctgagg ctcaaagcac                                              20

<210> SEQ ID NO 50
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
ggaaaaaccg gagaagcuga                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cauucttgtg gaaaaaccgg                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
auaccatatc tcattcuugu                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ugcucagttc tataccauau                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ggccacagct gcttgcucag                                                   20

<210> SEQ ID NO 55
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
acuggcatct ggccacagcu                                                 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
aggacccttg cactggcauc                                                 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
agugggcatc aggacccuug                                                 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
cagccgctgg cagtgggcau                                                 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
aggcctggct ggccagccgc                                                 20

<210> SEQ ID NO 60
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
uggugcggca ggcctggcug                                                      20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
ggaggcacgg gttggugcgg                                                      20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
agcgaccccc atggaggcac                                                      20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
accuctaggc agcgaccccc                                                      20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
gguggccctc cacctcuagg                                                      20

<210> SEQ ID NO 65
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
uggcacaggc ggtggcccuc                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
cccaccgggc agtggcacag                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
gcuccggtgt agcccaccgg                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
cgucgcagaa ggctccggug                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
uggugtccac gtcgcagaag                                              20
```

```
<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
agcagcttgc cttggugucc                                                    20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
cggccatcat agcagcuugc                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
agcugagccc gcggccauca                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
gccaggccgc ggtagcugag                                                    20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
cguggtcctg gccaggccgc                                                    20
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 75
cacccgagag cgtgguccug        20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 76
gcugacaggg cgcacccgag        20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 77
cgaggcccac ggctgacagg        20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 78
agguggcctc cgaggcccac        20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 79
gucacgttcc ggtagguggc        20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 80
cuugctcggc agtcacguuc       20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 81
ccagutccgc gcttgcucgg       20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 82
cgcccagtcc ccagtuccgc       20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 83
aaggcgtggc cgcccagucc       20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 84
ggguuccggc agaaggcgug                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
ugucgttgtc cgggtuccgg                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
accacgggcg gatgtcguug                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
agcacgaagc accacgggcg                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
ggucgcggtt cagcacgaag                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
cagcucagcc ggtcgcgguu                                             20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
cgcagtactc ccagcucagc                                             20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
acugugccag gtcgcaguac                                             20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
gggguctggc actgtgccag                                             20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
gccgcctggg ttggggucug                                             20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 94
ggggucggag gcgccgccug                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95 agggggacacc ggggtcggag                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
acaugaagcc taggggacac                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ggcaugagtg ggacaugaag                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
cggcugcgcg ggcatgagug                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 99
uucggcggtg ccggcugcgc                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
gggcugaggc uucggcggug                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gguccgggtc gtgggcugag                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
acugaggcgg ggtccggguc                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
ccggggtctg ggactgaggc                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 104
ggcaaggctc ccggggucug                                              20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
ucccgcttcg ccggcaaggc                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
aaggcggctg ctcccgcuuc                                              20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
cuggucaggg aaggcggcug                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
agugggccgt tcctggucag                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 109
cccgcagctc agtgggccgu                                                 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
ugcggagccg ctgcccgcag                                                 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
acagactctt gcggagccgc                                                 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
gggucatcga agacagacuc                                                 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
ccaacgacgc gggtcaucga                                                 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 114
gccaccagcc cgccaacgac                                                     20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gccccgcgta gcgccaccag                                                     20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
uaggggtgcg ccccgcguag                                                     20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
agcgcggcga tgtaggggug                                                     20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
ggccccagta cagcgcggcg                                                     20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
    oligonucleotide
<220> FEATURE:
<223> OTHER INFORMATION: Description of Combined DNA/RNA Molecule:
      Synthetic oligonucleotide

<400> SEQUENCE: 119
gcagaaactg tggccccagu                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
gaggctgccg gcgcagaaac                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
gggggcgatg aggctgccgg                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
agcacccagc aggggcgau                                               20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
gagcggccgt cagcacccag                                              20

<210> SEQ ID NO 124
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
ccugcaggca gtgagcggcc                                               20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
gugcgggccg gtcctgcagg                                               20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
agauccucgg gtgcgggccg                                               20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
caccaccgtc agatccucgg                                               20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
guuccuggcc gagcaccacc                                               20

<210> SEQ ID NO 129
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ugguuacggc gttccuggcc                                                     20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
gcucacagct gtggtuacgg                                                     20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
acguctggca cggctcacag                                                     20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
gcacggccaa cgtctggcac                                                     20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
agcggtagga gcgcacggcc                                                     20

<210> SEQ ID NO 134
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
aggcctcgtg caagcgguag                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
acgggcgaga aggccucgug                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
gcuggtagct gacgggcgag                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
agccaggtcg tgctgguagc                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
aggcgcaaca gagccagguc                                              20

<210> SEQ ID NO 139
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
caucctcctg aaggcgcaac                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
agcugccgtc cgcatccucc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
aggagcgcgc agctgccguc                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
acguaaggcg acaggagcgc                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
acaccggctg aacgtaaggc                                              20

<210> SEQ ID NO 144
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
cuuggcaggc acaccggcug                                                 20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
cgcgcggcgc cgcttggcag                                                 20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
ucggagggtc gcgcggcgcc                                                 20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
agagcgtggt ctcggagggu                                                 20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
ccggccacct ggcagagcgu                                                 20
```

```
<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
uggccccagc cggccaccug                                                  20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
ccucgaactg gtggccccag                                                  20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
auuccuccgc cccctcgaac                                                  20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
aagcuggcat attccuccgc                                                  20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
cgccuccugc aggaagcugg                                                  20
```

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
aacggtacct gcgccuccug        20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
agggagagga acggtaccug        20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
agcagcgctc cagggagagg        20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
cguccggggc tgagcagcgc        20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
aggauccgtg cacgtccggg        20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
ggggaggatg gaggauccgu                                                    20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
gagcatgccg gggaggaugg                                                    20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
gaaccctgcg cagagcaugc                                                    20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
gccgccctcg aggaacccug                                                    20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
acgcatcggt gccgcccucg                                              20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
aaucaccctg gcacgcaucg                                              20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
gggcctccgg aatcacccug                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
acacaccagc gggccuccgg                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
agcuuggtcc tcacacacca                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
ccggcgctct gcagcuuggu                                                   20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
cagggtgagc cggcgcucug                                                   20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170 augaugccttt gcagggugag                                                  20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
auccccagct gatgaugccu                                                   20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
accacagccc gatccccagc                                                   20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 173
gcuugttgcg gtcaccacag                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
guagacgcct ggcttguugc                                              20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
cacaucggtg tagacgccug                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
ccaggtagta ggccacaucg                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
ggauccaggc caggtaguag                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 178
ggugugctcc cggatccagg                                               20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
aaucaggaaa cggtgugcuc                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
agucccugag caatcaggaa                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
agggaaagat gagtcccuga                                               20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
gaaucaccaa ggagggaaag                                               20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 183
ucucactgcg gaatcaccaa                                       20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
ccccagccac tctctcacug                                       20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
uugccttcca tgccccagcc                                       20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
gacacaatct tgcctuccau                                       20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187 cuggggaat gggacacaau                                        20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 188
agcuggccgc actgggggaa                                               20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
auccuggcgc ggagcuggcc                                               20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
guucctgcgc catccuggcg                                               20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
cacuutattg agttccugcg                                               20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
auuuucaaag cacttuauug                                               20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 193
uuuuuctcag catttucaaa                                               20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 194
agcugcctat ccaggagucc                                               20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
ccguuggtcc agctgccuau                                               20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
auggcatccg tccgtugguc                                               20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
agcagagccc tcatggcauc                                               20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 198
accccaggag cagcagagcc                                              20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
accagcagga accccaggag                                              20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
acuccaagct caccagcagg                                              20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
cgaaagtgtt gactccaagc                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
ccaaggtgga atcgaaagug                                              20

<210> SEQ ID NO 203
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
ugggggcttc ccaaggugga                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
acuuatgctc cttgggggcu                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
cuucagcttt gtactuaugc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
acugugtgct cttcagcuuu                                              20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
acagugagaa cgactgugug                                              20

<210> SEQ ID NO 208
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
uccccggtga cagtgagaac                                                     20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
aguggcaggg ctccccggug                                                     20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
acuggaaggg gaagtggcag                                                     20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
gcugccggtg gtactggaag                                                     20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
uuguggtaca gctgccggug                                                     20

<210> SEQ ID NO 213
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
ugugggtaca tttgtgguac                                                    20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
uggccggccc ttgtgggguac                                                   20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
ggcugagggc ctggccggcc                                                    20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
guagcacacc agggcugagg                                                    20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217 aguuggggt ggtagcacac                                                     20

<210> SEQ ID NO 218
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
ccugatcaaa gttggggggug                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
ccccatcgct ggtccugauc                                               20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
aaacagtatc cccatcgcug                                               20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
ucuugggctc caaacaguau                                               20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
ugguctttca ctttcuuggg                                               20

<210> SEQ ID NO 223
```

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 223
guuugctgca gtggtcuuuc                                               20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 224
aggggctgtg tttgcugcag                                               20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 225
cuccuttctg gcaggggcug                                               20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 226
acacaggtcc ctcctuucug                                               20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 227
uuggcatgtt cacacagguc                                               20

```
<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
agugggggcc gcttggcaug                                                    20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
ggacagagac agtgggggcc                                                    20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
ugaggtgttg tggacagaga                                                    20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
aguggtttcc agtgaggugu                                                    20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
ucucuttctg gcagtggsuuu                                                   20
```

```
<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
caaagcactt ctcttucugg                                              20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
gaagctgagg ctcaaagcac                                              20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
ggaaaaaccg gagaagcuga                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
cauucttgtg gaaaaaccgg                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
auaccatatc tcattcuugu                                              20
```

```
<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
ugcucaguuc tataccauau                                              20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
ggccacagct gcttgcucag                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
acuggcatct ggccacagcu                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
aggacccttg cactggcauc                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
```
agugggcauc aggacccuug                    20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
cagccgctgg cagtgggcau                    20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
aggcctggct ggccagccgc                    20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
uggugcggca ggcctggcug                    20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
ggaggcacgg gttggugcgg                    20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
agcgaccccc atggaggcac                                                   20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
accuctaggc agcgaccccc                                                   20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
gguggccctc cacctcuagg                                                   20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
uggcacaggc ggtggcccuc                                                   20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
cccaccgggc agtggcacag                                                   20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
gcuccggtgt agcccaccgg                                           20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
cgucgcagaa ggcuccggug                                           20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
uggugtccac gtcgcagaag                                           20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
agcagcttgc cttggugucc                                           20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
cggccatcat agcagcuugc                                           20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 257
agcugagccc gcggccauca                                                    20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
gccaggccgc ggtagcugag                                                    20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
cguggtcctg gccaggccgc                                                    20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
cacccgagag cgtgguccug                                                    20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
gcugacaggg cgcacccgag                                                    20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 262
cgaggcccac ggctgacagg                                               20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
agguggcctc cgaggcccac                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
gucacgttcc ggtagguggc                                               20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
cuugctcggc agtcacguuc                                               20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
ccagutccgc gcttgcucgg                                               20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 267
cgcccagtcc ccagtuccgc                                                     20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
aaggcgtggc cgcccagucc                                                     20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
ggguuccggc agaaggcgug                                                     20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
ugucgttgtc cgggtuccgg                                                     20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
accacgggcg gatgtcguug                                                     20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 272
agcacgaagc accacgggcg                                                   20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
ggucgcggtt cagcacgaag                                                   20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
cagcucagcc ggtcgcgguu                                                   20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
cgcagtactc ccagcucagc                                                   20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
acugugccag gtcgcaguac                                                   20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
              oligonucleotide
<220> FEATURE:
<223> OTHER INFORMATION: Description of Combined DNA/RNA Molecule:
      Synthetic oligonucleotide

<400> SEQUENCE: 277
gggguctggc actgtgccag                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
gccgcctggg ttgggucug                                               20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
ggggucggag gcgccgccug                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
aggggacacc ggggtcggag                                              20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
acaugaagcc tagggacac                                               20

<210> SEQ ID NO 282
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
ggcaugagtg ggacaugaag                                               20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
cggcugcgcg ggcatgagug                                               20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
uucggcggtg ccggcugcgc                                               20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
gggcugaggc ttcggcggug                                               20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
gguccgggtc gtgggcugag                                               20

<210> SEQ ID NO 287
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
acugaggcgg ggtccggguc                                                 20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ccggggtctg ggactgaggc                                                 20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
ggcaaggctc ccggggucug                                                 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ucccgcttcg ccggcaaggc                                                 20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
aaggcggctg ctcccgcuuc                                                 20

<210> SEQ ID NO 292
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
cuggucaggg aaggcggcug                                                   20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
agugggccgt tcctggucag                                                   20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
cccgcagctc agtgggccgu                                                   20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
ugcggagccg ctgcccgcag                                                   20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
acagactctt gcggagccgc                                                   20

<210> SEQ ID NO 297
<211> LENGTH: 20

-continued

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
gggucatcga agacagacuc                                              20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
ccaacgacgc gggtcaucga                                              20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
gccaccagcc cgccaacgac                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
gccccgcgta gcgccaccag                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
uaggggtgcg ccccgcguag                                              20

<210> SEQ ID NO 302

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
agcgcggcga tgtaggggug                                              20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
ggccccagta cagcgcggcg                                              20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
gcagaaactg tggccccagu                                              20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
gaggctgccg gcgcagaaac                                              20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
gggggcgatg aggctgccgg                                              20
```

```
<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
agcacccagc aggggcgau                                                    20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
gagcggccgt cagcacccag                                                   20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
ccugcaggca gtgagcggcc                                                   20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
gugcgggccg gtcctgcagg                                                   20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
agauccucgg gtgcgggccg                                                   20
```

```
<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
caccaccgtc agatccucgg                                               20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
guucctggcc gagcaccacc                                               20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
ugguuacggc gttccuggcc                                               20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
gcucacagct gtggtuacgg                                               20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
acguctggca cggctcacag                                               20
```

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
gcacggccaa cgtctggcac                                              20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
agcggtagga gcgcacggcc                                              20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
aggcctcgtg caagcgguag                                              20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
acgggcgaga aggccucgug                                              20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321

```
gcuggtagct gacgggcgag                                          20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 322
agccaggtcg tgctgguagc                                          20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
aggcgcaaca gagccagguc                                          20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
caucctcctg aaggcgcaac                                          20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
agcugccgtc cgcatccucc                                          20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
```
aggagcgcgc agctgccguc 20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
acguaaggcg acaggagcgc 20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
acaccggctg aacgtaaggc 20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
cuuggcaggc acaccggcug 20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
cgcgcggcgc cgcttggcag 20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
ucggagggtc gcgcggcgcc                                          20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
agagcgtggt ctcggagggu                                          20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
ccggccacct ggcagagcgu                                          20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
uggccccagc cggccaccug                                          20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
ccucgaactg gtggccccag                                          20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
auuccuccgc cccctcgaac                                                    20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
aagcuggcat attccuccgc                                                    20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
cgccuccugc aggaagcugg                                                    20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
aacggtacct gcgccuccug                                                    20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
agggagagga acggtaccug                                                    20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
Synthetic oligonucleotide

<400> SEQUENCE: 341
agcagcgctc cagggagagg                                               20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
cguccggggc tgagcagcgc                                               20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
aggauccgtg cacgtccggg                                               20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
ggggaggaug gaggauccgu                                               20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
gagcatgccg gggaggaugg                                               20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 346
gaaccctgcg cagagcaugc                                                     20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
gccgccctcg aggaacccug                                                     20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
acgcatcggt gccgcccucg                                                     20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
aaucaccctg gcacgcaucg                                                     20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
gggcctccgg aatcacccug                                                     20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 351
acacaccagc gggccuccgg                                              20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
agcuuggtcc tcacacacca                                              20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
ccggcgctct gcagcuuggu                                              20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
cagggtgagc cggcgcucug                                              20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
augaugcctt gcagggugag                                              20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
        Synthetic oligonucleotide

<400> SEQUENCE: 356
auccccagct gatgaugccu                                                      20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<223> OTHER INFORMATION: Description of Combined DNA/RNA Molecule:
        Synthetic oligonucleotide

<400> SEQUENCE: 357
accacagccc gatccccagc                                                      20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<223> OTHER INFORMATION: Description of Combined DNA/RNA Molecule:
        Synthetic oligonucleotide

<400> SEQUENCE: 358
gcuugttgcg gtcaccacag                                                      20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<223> OTHER INFORMATION: Description of Combined DNA/RNA Molecule:
        Synthetic oligonucleotide

<400> SEQUENCE: 359
guagacgcct ggcttguugc                                                      20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<223> OTHER INFORMATION: Description of Combined DNA/RNA Molecule:
        Synthetic oligonucleotide

<400> SEQUENCE: 360
cacaucggtg tagacgccug                                                      20

<210> SEQ ID NO 361
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
ccaggtagta ggccacaucg                                               20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
ggauccaggc caggtaguag                                               20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
ggugugctcc cggatccagg                                               20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
aaucaggaaa cggtgugcuc                                               20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
agucccugag caatcaggaa                                               20

<210> SEQ ID NO 366
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 366
agggaaagat gagtcccuga                                                   20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367
gaaucaccaa ggagggaaag                                                   20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
ucucactgcg gaatcaccaa                                                   20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
ccccagccac tctctcacug                                                   20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
uugccttcca tgcccagcc                                                    20

<210> SEQ ID NO 371
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371
gacacaatct tgcctuccau                                                   20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372 cuggggggaat gggacacaau                                                  20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
agcuggccgc actgggggaa                                                   20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
auccuggcgc ggagcuggcc                                                   20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
guucctgcgc catccuggcg                                                   20

<210> SEQ ID NO 376
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
cacuutattg agttccugcg                                              20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
auuuucaaag cacttuauug                                              20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378
uuuuuctcag catttucaaa                                              20
```

POLYNUCLEOTIDE AGENTS TARGETING FACTOR XII (HAGEMAN FACTOR) (F12) AND METHODS OF USE THEREOF

RELATED APPLICATIONS

This application is a 35 U.S.C. § 371 national stage filing of International Application No. PCT/US2017/012420, filed on Jan. 6, 2017, which in turn claims the benefit of priority to U.S. Provisional Patent Application No. 62/276,279, filed on Jan. 8, 2016. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on Dec. 19, 2016, is named 121301-05320_SL.txt and is 133,631 bytes in size.

BACKGROUND OF THE INVENTION

Hereditary Angioedema (HAE) is a rare autosomal dominant disorder that causes recurrent edema and swelling of the extremities, face, larynx, upper respiratory tract, abdomen, trunk, and genitals and a nonpruritic rash in one-third of patients. Untreated HAE patients experience an average of one-to-two angioedema attacks per month, but the frequency and severity of episodes can vary significantly. Edema swelling is often disfiguring and disabling, results in frequent hospitalization, and patients may require psychiatric care to treat disease-associated anxiety. Abdominal attacks can cause severe pain, nausea and vomiting, and may lead to inappropriate surgeries. Furthermore, over half of HAE patients also experience life-threatening laryngeal edema during their lifetime that may require emergency tracheostomy to prevent asphyxiation. HAE affects an estimated 6,000 to 10,000 individuals of varying ethnic groups in the United States and causes significant economic harm to patients, accounting for 15,000 to 30,000 hospital visits and 20 to 100 sick days per year.

HAE results from a mutation of the C1 inhibitor (C1INH, SERPING1) gene that results in a deficiency of C1INH protein. Over 250 different C1INH mutations have been demonstrated to cause an HAE clinical presentation. These C1INH mutations are typically inherited genetically, however, up to 25% of HAE cases result from de novo mutation of C1INH. HAE type I is caused by C1INH mutations that result in lower levels of truncated or misfolded proteins that are inefficiently secreted, and accounts for approximately 85% of HAE cases. HAE type II constitutes about 15% of cases and is caused by mutations near the active site of C1INH that result in normal levels of dysfunctional C1INH protein. HAE type III, a rare third form the disease, occurs as a result of a gain-of-function mutation in coagulation factor XII (F12) (Hageman Factor).

C1 inhibitor is a serine protease inhibitor of the serpin family and a major inhibitor of proteases in the complement and contact activation pathways, as well as a minor inhibitor of fibrinolytic protease plasmin. These plasma proteolytic cascades are activated during an HAE attack, generating substances that increase vascular permeability. Studies have shown that the bradykinin peptide, which activates proinflammatory signaling pathways that dilate vessels and induces chemotaxis of neutrophils, is the primary substance that enhances vascular permeability in an HAE attack by binding to the bradykinin receptor on vascular endothelial cells. The formation of bradykinin in plasma generally requires interaction of three proteins, namely F12, prekallikrein and high-molecular-weight kininogen, collectively referred to as the "contact activation pathway" or the "Kallikrein-Kinin System." Prekallikrein and high-molecular-weight kininogen circulate as a bi-molecular complex. The contact activation pathway is initiated on binding of F12 to negatively charged surfaces (or macromolecules) which induces a conformational change in F12 resulting in active F12 (F12a). F12a cleaves prekallikrein to generate active kallikrein, which in turn reciprocally activates F12. The active kallikrein then digests high-molecular-weight kininogen to liberate bradykinin.

Typically, C1INH inhibits the autoactivation of F12, the ability of F12a to activate prekallilrein, the activation of high molecular weight kininogen by kallikrein, and the feedback activation of F12 by kallikrein. Consequently, mutations causing C1INH deficiency or F12 gain-of-function result in excess production of bradykinin and onset of HAE angioedema.

Currently, HAE may be treated with 17α-alkylated androgens prophylactically to reduce to probability of recurrent episodes, or with disease-specific therapeutics to treat acute attacks. About 70% of individuals with HAE are treated with androgens or remain untreated, and about 30% receive therapeutics. Androgens are unsuitable for short-term treatment of acute attacks because they take several days to become effective, and they can have significant side effects and may affect growth and development adversely. As a result, androgens are used only for long-term prophylaxis and are typically not administered to pregnant women or children. Furthermore, current therapeutics used to treat acute attacks must be administered intravenously numerous times per week or may cause side-effects that require drug administration and subsequent patient monitoring in a hospital, thereby limiting their regular prophylactic use to manage the disease long-term. Therefore, in the absence of regimens which be administered safely, effectively and by more convenient routes and regimens to treat acute angioedema attacks and prophylactically manage recurrent attacks in a large proportion of patients, including pregnant women and children, there is a need for alternative therapies for subjects suffering from HAE.

SUMMARY OF THE INVENTION

The present invention provides polynucleotide agents and compositions comprising such agents which target nucleic acids encoding a Factor XII (F12) gene and interfere with the normal function of the targeted nucleic acid. The Factor XII nucleic acid may be within a cell, e.g., a cell within a subject, such as a human. The present invention also provides methods and combination therapies for treating a subject having a disorder that would benefit from inhibiting or reducing the expression of a Factor XII mRNA, e.g., a Factor XII-associated disease, such as a contact activation pathway-associated disease, such as hereditary angioedema (HAE), Flectcher Factor Deficiency, or essential hypertension using the polynucleotide agents and compositions of the invention.

Accordingly, in some aspects, the present invention provides antisense polynucleotide agents for inhibiting expression of Factor XII. The agents comprise 4 to 50 contiguous nucleotides, wherein at least one of the contiguous nucleotides is a modified nucleotide, and wherein the nucleotide sequence of the agent is at least 80% complementary over its entire length to the equivalent region of the nucleotide sequence of any one of SEQ ID NOs:1-4.

In one embodiment, the equivalent region is a target region of SEQ ID NO:1, e.g., residues 21-74, 87-106, 143-183, 209-239, 254-273, 287-315, 320-350, 352-392, 395-414, 352-414, 430-470, 472-568, 595-680, 595-669, 682-701, 736-899, 793-843, 793-899, 804-899, 901-942, 736-942, 968-987, 990-1097, 990-1042, 1100-1197, 1100-1206, 1210-1252, 1210-1240, 1253-1272, 1298-1406, 1308-1406, 1430-1515, 1430-1482, 1541-1560, 1583-1602, 1683-1714, 1727-1768, 1737-1756, 1781-1976, 1816-1868, 1902-1967, 1891-1957, 1992-2043, or 1992-203 of SEQ ID NO:1. In certain embodiments, the target region of SEQ ID NO: 1 is any one of the target regions listed in Table 3. In certain embodiments, the target region of SEQ ID NO: 1 is one of the target regions selected from the group consisting of the regions targeted by antisense agent A-145669, A-145668, A-145667, A-145572, A-145567, A-145666, A-145670, A-145674, A-145660, A-145676, A-145539, A-145566, A-145527, A-145548, A-145549, A-145573, A-145661, A-145570, A-145597, A-145600, A-145658; A-145556, A-145656, A-145659, A-145671, A-145675, A-145519, A-145538, A-145619, A-145520, A-145594, A-145540, A-145547, A-145550, A-145551, A-145657, A-145568, A-145575, A-145565, A-145584, A-145616, A-145541, A-145542, A-145555, A-145571, A-145596, A-145599, A-145617, A-145655, A-145663, A-145532, A-145603, A-145665, A-145537, A-145612, A-145651, A-145586; A-145533, A-145569, A-145561, A-145604, A-145506, A-145664, A-145585, A-145595, A-145618, A-145613, A-145615, A-145677, A-145523, A-145552, A-145593, A-145598, A-145633, A-145543, A-145557, A-145624, A-145629, A-145646, A-145512, A-145536, A-145583, A-145625, A-145576, A-145623, A-145626; A-145562, A-145577, A-145588, A-145650, A-145534, A-145601, A-145662, A-145522, A-145525, A-145589, A-145607, A-145516, A-145529, A-145564, A-145605, A-145495, A-145496, A-145507, A-145614, A-145637, A-145497, A-145526, A-145591, A-145628, A-145647, A-145498, A-145501, A-145508, A-145560, A-145590, A-145611, A-145627, A-145652, A-145672, A-145513, A-145563, A-145581, A-145553, or A-145587. In certain embodiments, the target region of SEQ ID NO: 1 is one of the target regions selected from the group consisting of the regions targeted by antisense agent A-145669, A-145668, A-145667, A-145572, A-145567, A-145666, A-145670, A-145674, A-145660, A-145676, A-145539, A-145566, A-145527, A-145548, A-145549, A-145573, A-145661, A-145570, A-145597, A-145600, A-145658; A-145556, A-145656, A-145659, A-145671, A-145675, A-145519, A-145538, A-145619, A-145520, A-145594, A-145540, A-145547, A-145550, A-145551, A-145657, A-145568, A-145575, A-145565, A-145584, A-145616, A-145541, A-145542, A-145555, A-145571, A-145596, A-145599, A-145617, A-145655, A-145663, A-145532, A-145603, A-145665, A-145537, A-145612, A-145651, A-145586; A-145533, A-145569, A-145561, A-145604, A-145506, A-145664, A-145585, A-145595, A-145618, A-145613, A-145615, A-145677, A-145523, A-145552, A-145593, A-145598, A-145633, A-145543, A-145557, A-145624, A-145629, A-145646, A-145512, A-145536, A-145583, A-145625, A-145576, A-145623, or A-145626. In certain embodiments, the target region of SEQ ID NO: 1 is one of the target regions selected from the group consisting of the regions targeted by antisense agent A-145669, A-145668, A-145667, A-145572, A-145567, A-145666, A-145670, A-145674, A-145660, A-145676, A-145539, A-145566, A-145527, A-145548, A-145549, A-145573, A-145661, A-145570, A-145597, A-145600, A-145658; A-145556, A-145656, A-145659, A-145671, A-145675, A-145519, A-145538, A-145619, A-145520, A-145594, A-145540, A-145547, A-145550, A-145551, A-145657, A-145568, A-145575, A-145565, A-145584, A-145616, A-145541, A-145542, A-145555, A-145571, A-145596, A-145599, A-145617, A-145655, A-145663, A-145532, A-145603, A-145665, A-145537, A-145612, A-145651, or A-145586.

In another aspect, the present invention provides antisense polynucleotide agents for inhibiting expression of Factor XII, wherein the agent comprises at least 8 contiguous nucleotides differing by no more than 3 nucleotides from any one of the nucleotide sequences listed in Table 3. In certain embodiments, the agent comprises at least 8 contiguous nucleotides differing by no more than 3 nucleotides from any one of A-145669, A-145668, A-145667, A-145572, A-145567, A-145666, A-145670, A-145674, A-145660, A-145676, A-145539, A-145566, A-145527, A-145548, A-145549, A-145573, A-145661, A-145570, A-145597, A-145600, A-145658; A-145556, A-145656, A-145659, A-145671, A-145675, A-145519, A-145538, A-145619, A-145520, A-145594, A-145540, A-145547, A-145550, A-145551, A-145657, A-145568, A-145575, A-145565, A-145584, A-145616, A-145541, A-145542, A-145555, A-145571, A-145596, A-145599, A-145617, A-145655, A-145663, A-145532, A-145603, A-145665, A-145537, A-145612, A-145651, A-145586; A-145533, A-145569, A-145561, A-145604, A-145506, A-145664, A-145585, A-145595, A-145618, A-145613, A-145615, A-145677, A-145523, A-145552, A-145593, A-145598, A-145633, A-145543, A-145557, A-145624, A-145629, A-145646, A-145512, A-145536, A-145583, A-145625, A-145576, A-145623, A-145626; A-145562, A-145577, A-145588, A-145650, A-145534, A-145601, A-145662, A-145522, A-145525, A-145589, A-145607, A-145516, A-145529, A-145564, A-145605, A-145495, A-145496, A-145507, A-145614, A-145637, A-145497, A-145526, A-145591, A-145628, A-145647, A-145498, A-145501, A-145508, A-145560, A-145590, A-145611, A-145627, A-145652, A-145672, A-145513, A-145563, A-145581, A-145553, or A-145587.

In some embodiments, substantially all of the nucleotides of the antisense polynucleotide agents of the invention are modified nucleotides. In other embodiments, all of the nucleotides of the antisense polynucleotide agent are modified nucleotides.

The antisense polynucleotide agent may be about 10 to 40 nucleotides in length; 10 to 30 nucleotides in length; 18 to 30 nucleotides in length; 10 to 24 nucleotides in length; 18 to 24 nucleotides in length; 12 or 20 nucleotides in length.

In one embodiment, the modified nucleotide comprises a modified sugar moiety selected from the group consisting of a 2'-O-methoxyethyl modified sugar moiety, a 2'-methoxy modified sugar moiety, a 2'-O-alkyl modified sugar moiety, and a bicyclic sugar moiety.

In one embodiment, the bicyclic sugar moiety has a (—CRH—)n group forming a bridge between the 2' oxygen and the 4' carbon atoms of the sugar ring, wherein n is 1 or 2 and wherein R is H, $CH_3$ or $CH_3OCH_3$.

In a further embodiment, n is 1 and R is $CH_3$.

In another embodiment, the modified nucleotide is a 5-methylcytosine.

In one embodiment, the modified nucleotide comprises a modified internucleoside linkage, such as a phosphorothioate internucleoside linkage.

In one embodiment, an agent of the invention comprises a plurality of 2'-deoxynucleotides flanked on each side by at least one nucleotide having a modified sugar moiety.

In one embodiment, the agent is a gapmer comprising a gap segment comprised of linked 2'-deoxynucleotides positioned between a 5' and a 3' wing segment.

In some embodiments, the agents of the invention further comprise a ligand.

In one embodiment, the agent is conjugated to the ligand at the 3'-terminus.

In one embodiment, the ligand is an N-acetylgalactosamine (GalNAc) derivative.

In one embodiment, the ligand is

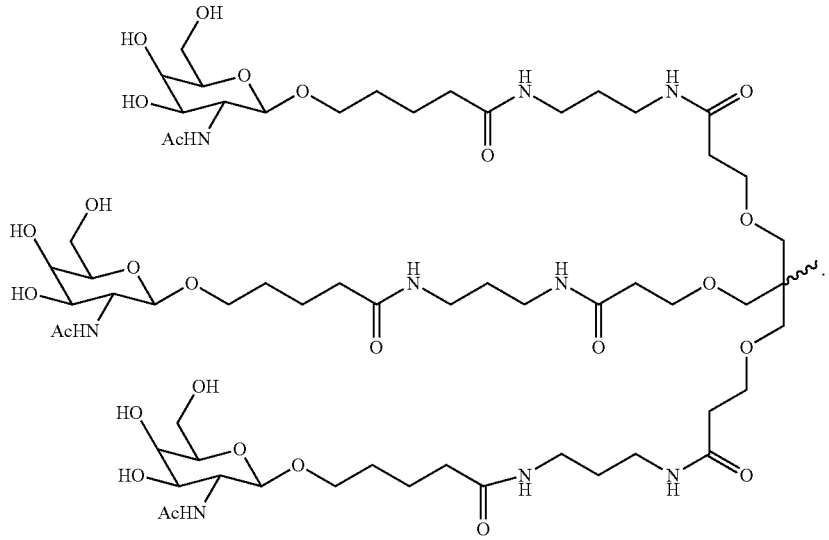 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In one embodiment, the 5'-wing segment is about 1 to 6 nucleotides in length, e.g., 2, 3, 4, or 5 nucleotides in length.

In one embodiment, the 3'-wing segment is about 1 to 6 nucleotides in length, e.g., 2, 3, 4, or 5 nucleotides in length.

In one embodiment, the gap segment is about 5 to 14 nucleotides in length, e.g., 6, 7, 8, 9, 10, 11, 12, 13, or 14 nucleotides in length.

In one aspect, the present invention provides antisense polynucleotide agents for inhibiting Factor XII expression, comprising a gap segment consisting of linked deoxynucleotides; a 5'-wing segment consisting of linked nucleotides; a 3'-wing segment consisting of linked nucleotides; wherein the gap segment is positioned between the 5'-wing segment and the 3'-wing segment and wherein each nucleotide of each wing segment comprises a modified sugar.

In one embodiment, the gap segment is ten 2'-deoxynucleotides in length and each of the wing segments is five nucleotides in length.

In another embodiment, the gap segment is ten 2'-deoxynucleotides in length and each of the wing segments is four nucleotides in length.

In yet another embodiment, the gap segment is ten 2'-deoxynucleotides in length and each of the wing segments is three nucleotides in length.

In another embodiment, the gap segment is ten 2'-deoxynucleotides in length and each of the wing segments is two nucleotides in length.

In one embodiment, the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

In one aspect, the present invention provides pharmaceutical compositions for inhibiting expression of a Factor XII gene comprising the agents of the invention.

In one embodiment, the agent is present in an unbuffered solution, such as saline or water.

In another embodiment, the agent is is present in a buffer solution, such as a buffer comprising acetate, citrate, prolamine, carbonate, or phosphate or any combination thereof.

In one embodiment, the buffer solution is phosphate buffered saline (PBS).

In another aspect, the present invention provides pharmaceutical composition comprising an agent of the invention and a lipid formulation, such as a lipid formulation comprising an LNP or a MC3.

In one aspect, the present invention provides methods of inhibiting Factor XII expression in a cell. The methods include contacting the cell with the agent of the invention or a pharmaceutical composition of the invention; and maintaining the cell for a time sufficient to obtain antisense inhibition of a Factor XII gene, thereby inhibiting expression of the Factor XII gene in the cell.

In some embodiments, the cell is within a subject.

In some embodiments, the subject is a human. In some embodiments, the subject is not human.

In one embodiment, the Factor XII expression is inhibited by at least 30%, 40%, 50%, 60%, 70%, 80%, 90%, 95%, or to below the level of detection of the assay.

In certain embodiments, the expression of the target is normalized, i.e., decreased to a level accepted as within the range of normal for an individual without such disorder. For example, the difference between a the expression level in a subject prior to treatment and normal expression level is decreased by at least 30%, 40%, 50%, 60%, 70%, 80%, 90%, 95%, or more.

In another aspect, the present invention provides methods of treating a subject having a disease or disorder that would benefit from reduction in Factor XII expression. The methods include administering to the subject a therapeutically effective amount of an agent of the invention or a pharmaceutical composition of the invention, thereby treating the subject.

In one embodiment, the administration of the antisense polynucleotide agent to the subject causes a decrease or normalization in at least one of elevated levels of bradykinin, prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain, or a decrease in Factor XII protein levels.

In one embodiment, the disorder is a Factor XII-associated disease.

In another embodiment, the Factor XII-associated disease is selected from heredity angioedema (HAE) (such as hereditary angioedema type I; hereditary angioedema type II; hereditary angioedema type III; or any other hereditary angioedema caused by elevated levels of bradykinin); prekallikrein deficiency, hypertension, e.g., malignant essential hypertension, end stage renal disease, or Fletcher Factor Deficiency.

In some embodiments, the Factor XII-associated disease is HAE.

In other embodiments, the Factor XII-associated disease is prekallikrein deficiency.

In other embodiments, the Factor XII-associated disease is hypertension, e.g., malignant essential hypertension.

In other embodiments, the Factor XII-associated disease is end stage renal disease.

In other embodiments, the Factor XII-associated disease is Fletcher Factor Deficiency.

In some embodiments the subject is human. In some embodiments, the subject is not human.

In some embodiments, the methods of the invention further include administering to the subject an androgen, such as danazol or oxandrolone, Berinert®, Cinryze™, Rhuconest®, Ecallantide, Firazyr®, Kalbitor®, or a combination of any of the foregoing to the subject.

In some embodiments, the methods of the invention further include determining Factor XII levels in the subject.

In some embodiments, the methods of the invention further include determining the level of bradykinin; prekallikrein, or blood pressure in the subject.

DETAILED DESCRIPTION OF THE INVENTION

The present invention provides polynucleotide agents, e.g., antisense polynucleotide agents, and compositions comprising such agents which target nucleic acids encoding Factor XII (e.g., mRNA encoding Factor XII as provided in, for example, any one of SEQ ID NOs:1-4). The polynucleotide agents bind to nucleic acids encoding Factor XII via, e.g., Watson-Crick base pairing, and interfere with the normal function of the targeted nucleic acid.

The antisense polynucleotide agents of the invention include a nucleotide sequence which is 4 to 50 nucleotides or less in length and which is 80% complementary to at least part of an mRNA transcript of a Factor XII gene. The use of these antisense polynucleotide agents enables the targeted inhibition of RNA expression or activity of a Factor XII gene in mammals.

The present inventors have demonstrated that antisense polynucleotide agents targeting Factor XII can mediate antisense inhibition in vitro resulting in significant inhibition of expression of a Factor XII gene. Thus, methods and compositions including these antisense polynucleotide agents are useful for treating a subject who would benefit by a reduction in the levels or activity of a Factor XII protein, such as a subject having a Factor XII-associated disease, such as heredity angioedema (HAE), prekallikrein deficiency, malignant essential hypertension, hypertension, end stage renal disease, or Fletcher Factor Deficiency.

The present invention also provides methods and combination therapies for treating a subject having a disorder that would benefit from inhibiting or reducing the expression of a Factor XII gene, e.g., a Factor XII-associated disease, such as heredity angioedema (HAE), prekallikrein deficiency, malignant essential hypertension, hypertension, end stage renal disease, or Fletcher Factor Deficiency using the antisense polynucleotide agents and compositions of the invention.

The present invention also provides methods for preventing at least one symptom, e.g., elevated levels of bradykinin, prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain, in a subject having a disorder that would benefit from inhibiting or reducing the expression of a Factor XII gene, e.g., a Factor XII-associated disease, such as heredity angioedema (HAE), prekallikrein deficiency, malignant essential hypertension, hypertension, end stage renal disease, or Fletcher Factor Deficiency. The present invention further provides compositions comprising antisense polynucleotide agents which effect antisense inhibition of a Factor XII gene. The Factor XII gene may be within a cell, e.g., a cell within a subject, such as a human.

The combination therapies of the present invention include administering to a subject having a Factor XII-associated disease, an antisense polynucleotide agent of the invention and an additional therapeutic, such as an androgen, such as danazol or oxandrolone, Berinert®, Cinryze™, Rhuconest®, Ecallantide, Firazyr®, Kalbitor®, and a combination of any of the foregoing.

The following detailed description discloses how to make and use antisense polynucleotide agents to inhibit the mRNA or protein expression of a Factor XII gene, as well as compositions, uses, and methods for treating subjects having diseases and disorders that would benefit from inhibition or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, a nucleoside with a modified base or a modified sugar is understood to include the options of a nucleoside with a modified base, a nucleoside with a modified sugar, and a nucleoside with a modified base and a modified sugar.

The term "about" is used herein to mean within the typical ranges of tolerances in the art. For example, "about" can be understood as about 2 standard deviations from the mean. In certain embodiments, about means +10%. In certain embodiments, about means +5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 17 nucleotides of a 20 nucleotide nucleic acid molecule" means that 17, 18, 19, or 20 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with mismatches to a target site of "no more than 2 nucleotides" has a 2, 1, or 0 mismatches. When "no more than" is present before a series of numbers or a range, it is understood that "no more than" can modify each of the numbers in the series or range.

As used herein, "up to" as in "up to 10" is understood as up to and including 10, i.e., 0, 1, 2, 3, 4, 5, 6, 7, 8, 9, or 10.

Ranges provided herein are understood to include all individual integer values and all subranges within the ranges.

As used herein, "Factor XII (Hageman Factor)," used interchangeably with the terms "coagulation factor XII," "FXII," "F12," active F12," and "F12a," refers to the naturally occurring gene that encodes the zymogen form of F12a. F12 a is an enzyme (EC 3.4.21.38) of the serine protease (or serine endopeptidase) class that cleaves prekallikrein to form kallikrein, which subsequently releases bradykinin from high-molecular weight kininogen and activates F12. The amino acid and complete coding sequences of the reference sequence of the F12 gene may be found in, for example, GenBank Accession No. GI:145275212 (RefSeq Accession No. NM_000505; SEQ ID NO:1). Mammalian orthologs of the human F12 gene may be found in, for example, GenBank Accession Nos. GI:544441267 (RefSeq Accession No. XM_005558647, cynomolgus monkey; SEQ ID NO:2); GI:805299477 (RefSeq Accession No. NM_021489, mouse; SEQ ID NO:3); and GI:62078740 (RefSeq Accession No. NM_001014006, rat; SEQ ID NO:4).

Additional examples of Factor XII mRNA sequences are readily available using publicly available databases, e.g., GenBank. Additional information on the human Factor XII gene can be found, for example, at www.ncbi.nlm.nih.gov/gene/2161 which is incorporated herein by reference in the version available on the filing date of the instant application.

The term"Factor XII," as used herein, also refers to naturally occurring DNA sequence variations of the Factor XII gene, such as a single nucleotide polymorphism in the Factor XII gene. Numerous SNPs within the Factor XII gene have been identified and may be found at, for example, NCBI dbSNP (see, e.g., www.ncbi.nlm.nih.gov/SNP/snp_ref.cgi?locusld=2161, which is incorporated herein by reference in the version available on the filing date of the instant application)

The terms "antisense polynucleotide agent" "antisense compound", and "agent" as used interchangeably herein, refer to an agent comprising a single-stranded oligonucleotide that contains RNA as that term is defined herein, and which targets nucleic acid molecules encoding Factor XII (e.g., mRNA encoding Factor XII as provided in, for example, any one of SEQ ID NOs:1-4). The antisense polynucleotide agents specifically bind to the target nucleic acid molecules via hydrogen bonding (e.g., Watson-Crick, Hoogsteen, or reversed Hoogsteen hydrogen bonding) and interfere with the normal function of the targeted nucleic acid (e.g., by an antisense mechanism of action). This interference with or modulation of the function of a target nucleic acid by the polynucleotide agents of the present invention is referred to as "antisense inhibition."

The functions of the target nucleic acid molecule to be interfered with may include functions such as, for example, translocation of the RNA to the site of protein translation, translation of protein from the RNA, splicing of the RNA to yield one or more mRNA species, and catalytic activity which may be engaged in or facilitated by the RNA.

In some embodiments, antisense inhibition refers to "inhibiting the expression" of target nucleic acid levels or target protein levels in a cell, e.g., a cell within a subject, such as a mammalian subject, in the presence of the antisense polynucleotide agent complementary to a target nucleic acid as compared to target nucleic acid levels or target protein levels in the absence of the antisense polynucleotide agent. For example, the antisense polynucleotide agents of the invention can inhibit translation in a stoichiometric manner by base pairing to the mRNA and physically obstructing the translation machinery, see Dias, N. et al., (2002) *Mol Cancer Ther* 1:347-355.

As used herein, "target sequence" refers to a contiguous portion of the nucleotide sequence of an mRNA molecule formed during the transcription of a Factor XII gene, including mRNA that is a product of RNA processing of a primary transcription product.

As used herein, "target nucleic acid" refers to a nucleic acid molecule to which an antisense polynucleotide agent specifically hybridizes.

As used herein, the term "specifically hybridizes" refers to an antisense polynucleotide agent having a sufficient degree of complementarity between the antisense polynucleotide agent and a target nucleic acid to induce a desired effect, while exhibiting minimal or no effects on non-target nucleic acids under conditions in which specific binding is desired, e.g., under physiological conditions in the case of in vivo assays and therapeutic treatments.

A target sequence may be about 4-50 nucleotides in length, e.g., about 8-45, 10-45, 10-40, 10-35, 10-30, 10-20, 11-45, 11-40, 11-35, 11-30, 11-20, 12-45, 12-40, 12-35, 12-30, 12-25, 12-20, 13-45, 13-40, 13-35, 13-30, 13-25, 13-20, 14-45, 14-40, 14-35, 14-30, 14-25, 14-20, 15-45, 15-40, 15-35, 15-30, 15-25, 15-20, 16-45, 16-40, 16-35, 16-30, 16-25, 16-20, 17-45, 17-40, 17-35, 17-30, 17-25, 17-20, 18-45, 18-40, 18-35, 18-30, 18-25, 18-20, 19-45, 19-40, 19-35, 19-30, 19-25, 19-20, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides of the nucleotide sequence of an mRNA molecule formed during the transcription of a Factor XII gene. Ranges and lengths intermediate to the above recited ranges and lengths are also contemplated to be part of the invention.

The terms "complementary," "fully complementary" and "substantially complementary" are used herein with respect to the base matching between an antisense polynucleotide agent and a target sequence. The term "complementarity" refers to the capacity for pairing between nucleobases of a first nucleic acid and a second nucleic acid.

As used herein, an antisense polynucleotide agent that is "substantially complementary to at least part of" a messenger RNA (mRNA) refers to an antisense polynucleotide agent that is substantially complementary to a contiguous portion of the mRNA of interest (e.g., an mRNA encoding Factor XII). For example, a polynucleotide is complementary to at least a part of a Factor XII mRNA if the sequence is substantially complementary to a non-interrupted portion of an mRNA encoding Factor XII.

As used herein, the term "region of complementarity" refers to the region of the antisense polynucletiode agent that is substantially complementary to a sequence, for example a target sequence, e.g., a Factor XII nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- or 3'-terminus of the antisense polynucleotide.

As used herein, and unless otherwise indicated, the term "complementary," when used to describe a first nucleotide sequence in relation to a second nucleotide sequence, refers to the ability of a polynucleotide comprising the first nucleotide sequence to hybridize and form a duplex structure under certain conditions with the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the nucleotides.

Complementary sequences include those nucleotide sequences of an antisense polynucleotide agent of the invention that base-pair to a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., antisense inhibition of target gene expression.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine and uracil as a base, respectively. However, it will be understood that the terms "deoxyribonucleotide", "ribonucleotide" and "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of the agents featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

A "nucleoside" is a base-sugar combination. The "nucleobase" (also known as "base") portion of the nucleoside is normally a heterocyclic base moiety. "Nucleotides" are nucleosides that further include a phosphate group covalently linked to the sugar portion of the nucleoside. For those nucleosides that include a pentofuranosyl sugar, the phosphate group can be linked to the 2', 3', or 5' hydroxyl moiety of the sugar. "Polynucleotides," also referred to as "oligonucleotides," are formed through the covalent linkage of adjacent nucleosides to one another, to form a linear polymeric oligonucleotide. Within the polynucleotide structure, the phosphate groups are commonly referred to as forming the internucleoside linkages of the polynucleotide.

In general, the majority of nucleotides of the antisense polynucleotide agents are ribonucleotides, but as described in detail herein, the agents may also include one or more non-ribonucleotides, e.g., a deoxyribonucleotide. In addition, as used in this specification, an "antisense polynucleotide agent" may include nucleotides (e.g., ribonucleotides or deoxyribonucleotides) with chemical modifications; an antisense polynucleotide agent may include substantial modifications at multiple nucleotides.

As used herein, the term "modified nucleotide" refers to a nucleotide having, independently, a modified sugar moiety, a modified internucleotide linkage, or modified nucleobase. Thus, the term modified nucleotide encompasses substitutions, additions or removal of, e.g., a functional group or atom, to internucleoside linkages, sugar moieties, or nucleobases. The modifications suitable for use in the antisense polynucleiotde agents of the invention include all types of modifications disclosed herein or known in the art. Any such modifications, as used in nucleotides, are encompassed by "antisense polynucleotide agent" for the purposes of this specification and claims.

As used herein, a "subject" is an animal, such as a mammal, including a primate (such as a human, a non-human primate, e.g., a monkey, and a chimpanzee), a non-human primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder, or condition that would benefit from reduction in Factor XII expression; a human at risk for a disease, disorder, or condition that would benefit from reduction in Factor XII expression; or a human having a disease, disorder or condition that would benefit from reduction in Factor XII expression.

As used herein, the terms "treating" or "treatment" refer to a beneficial or desired result including, but not limited to, alleviation or amelioration of one or more symptoms associated with heredity angioedema (HAE), prekallikrein deficiency, malignant essential hypertension, hypertension, end stage renal disease, or Fletcher Factor Deficiency. "Treatment" can also mean prolonging survival as compared to expected survival in the absence of treatment.

The term "lower" or "reduce" and the like in the context of the level of a Factor XII in a subject or a disease marker or symptom refers to a statistically significant decrease in such level. The decrease can be, for example, at least 20%, 25%, 30%, 35%, 40%, 45%, 50%, 55%, 60%, 65%, 70%, 75%, 80%, 85%, 90%, or 95%; or a similar level of reduction in the difference between a disease level and a normal level of a marker in an appropriate control subject. In certain embodiments, the decrease is down to a level accepted as within the range of normal for an individual without such disorder which can also be referred to as a normalization of a level. For example, lowering cholesterol to 180 mg/dl or lower would be considered to be within the range of normal for a subject. A subject having a cholesterol level of 230 mg/dl with a cholesterol level decreased to 210 mg/dl would have a cholesterol level that was decreased by 40% (230−210/230−180=20/50=40% reduction). In certain embodiments, the reduction is the normalization of the level of a sign or symptom of a disease, a reduction in the difference between the subject level of a sign of the disease and the normal level of the sign for the disease (e.g., upper level of normal, lower level of normal, average of upper and lower level of normal). For example, reduction can be understood as normalization of blood pressure, decreasing an elevated blood pressure or increasing a low blood pressure to reduce the difference from a normal reading.

As used herein, the term "Factor XII-associated disease" is a disease or disorder that is caused by, or associated with abnormal signaling in the contact activation pathway, e.g., abnormal contact activation pathway gene expression (i.e., KLKB1 gene expression, F12 gene expression, and/or KNG1 gene expression) or contact activation pathway protein production (i.e., KLKB1 protein production, F12 protein production, and/or KNG1 protein production). Such diseases are typically include a disease, disorder or condition that would benefit from reduction in contact activation pathway gene expression and/or activity. Non-limiting examples of contact activation pathway-associated diseases include, for example, diseases and conditions including heredity angioedema (HAE) (such as hereditary angioedema type I; hereditary angioedema type II; hereditary angioedema type III; or any other hereditary angioedema caused by elevated levels of bradykinin), prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain.

In one embodiment, a Factor XII-associated disease is HAE. In another embodiment, a Factor XII-associated disease is prekallikrein deficiency. In another embodiment, a Factor XII-associated disease is hypertension, e.g., malignant essential hypertension. In another embodiment, a Factor XII-associated disease is end stage renal disease. In another embodiment, a Factor XII-associated disease is Fletcher Factor deficiency.

II. Polynucleotide Agents of the Invention

The present invention provides polynucleotide agents, e.g., antisense polynucleotide agents, and compositions comprising such agents, which target a Factor XII gene and inhibit the expression of the Factor XII gene. In one embodiment, the polynucleotide agents, e.g., antisense polynucleotide agents, inhibit the expression of a Factor XII gene in a cell, such as a cell within a subject, e.g., a mammal, such as a human having a Factor XII-associated disease, e.g., heredity angioedema (HAE), prekallikrein deficiency, malignant essential hypertension, hypertension, end stage renal disease, or Fletcher Factor Deficiency.

The antisense polynucleotide agents of the invention include a region of complementarity which is complementary to at least a part of an mRNA formed in the expression of a Factor XII gene. The region of complementarity may be about 50 nucleotides or less in length (e.g., 22-12, 20-14, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4 nucleotides or less in length). Upon contact with a cell expressing the Factor XII gene, the antisense polynucleotide agent inhibits the expression of the Factor XII gene (e.g., a human, a primate, a non-primate, or a bird Factor XII gene) by at least 20% as assayed by, for example, a PCR or branched DNA (bDNA)-based method, or by a protein-based method, such as by immunofluorescence analysis, using, for example, western blotting, or flow cytometric techniques. In preferred embodiments, the inhibition of expression is determined using the qPCR method provided in Example 2 herein.

The region of complementarity between an antisense polynucleotide agent and a target sequence may be substantially complementary (e.g., there is a sufficient degree of complementarity between the antisense polynucleotide agent and a target nucleic acid to so that they specifically hybridize and induce a desired effect), but is generally fully complementary to the target sequence. The target sequence can be derived from the sequence of an mRNA formed during the expression of a Factor XII gene.

Accordingly, in one aspect, an antisense polynucleotide agent of the invention specifically hybridizes to a target nucleic acid molecule, such as the mRNA encoding Factor XII, and comprises a contiguous nucleotide sequence which corresponds to the reverse complement of a nucleotide sequence of any one of SEQ ID NOs:1-4, or a fragment of any one of SEQ ID NOs:1-4.

In some embodiments, the antisense polynucleotide agents of the invention may be substantially complementary to the target sequence. For example, an antisense polynucleotide agent that is substantially complementary to the target sequence may include a contiguous nucleotide sequence comprising no more than 5 mismatches (e.g., no more than 1, no more than 2, no more than 3, no more than 4, or no more than 5 mismatches) when hybridizing to a target sequence, such as to the corresponding region of a nucleic acid which encodes a mammalian Factor XII mRNA. In some embodiments, the contiguous nucleotide sequence comprises no more than a single mismatch when hybridizing to the target sequence, such as the corresponding region of a nucleic acid which encodes a mammalian Factor XII mRNA.

In some embodiments, the antisense polynucleotide agents of the invention that are substantially complementary to the target sequence comprise a contiguous nucleotide sequence which is at least 80% complementary over its entire length to the equivalent region of the nucleotide sequence of any one of SEQ ID NOs:1-4, or a fragment of any one of SEQ ID NOs:1-4, such as at least 85%, 90%, 95%, or 100% complementary.

In some embodiments, an antisense polynucleotide agent comprises a contiguous nucleotide sequence which is fully complementary over its entire length to the equivalent region of the nucleotide sequence of any one of SEQ ID NOs: 1-4 (or a fragment of any one of SEQ ID NOs:1-4). For example, the nucleotide sequence of an antisense polynucleotide agent is fully complementary over its entire length to the equivalent region of nucleotides 1-20 of GI:145275212 (SEQ ID NO:1) (see, e.g., Table 3).

An antisense polynucleotide agent may comprise a contiguous nucleotide sequence of about 4 to 50 nucleotides in length, or any subrange falling within that range, e.g., about 8-49, 8-48, 8-47, 8-46, 8-45, 8-44, 8-43, 8-42, 8-41, 8-40, 8-39, 8-38, 8-37, 8-36, 8-35, 8-34, 8-33, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 8-12, 8-11, 8-10, 8-9, 10-49, 10-48, 10-47, 10-46, 10-45, 10-44, 10-43, 10-42, 10-41, 10-40, 10-39, 10-38, 10-37, 10-36, 10-35, 10-34, 10-33, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 10-14, 10-13, 10-12, 10-11,11-49, 11-48, 11-47, 11-46, 11-45, 11-44, 11-43, 11-42, 11-41, 11-40, 11-39, 11-38, 11-37, 11-36, 11-35, 11-34, 11-33, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 11-14, 11-13, 11-12, 12-49, 12-48, 12-47, 12-46, 12-45, 12-44, 12-43, 12-42, 12-41, 12-40, 12-39, 12-38, 12-37, 12-36, 12-35, 12-34, 12-33, 12-32, 12-31, 12-30, 12-29, 12-28, 12-27, 12-26, 12-25, 12-24, 12-23, 12-22, 12-21, 12-20, 12-19, 12-18, 12-17, 12-16, 12-15, 12-14, 12-13, 13-49, 13-48, 13-47, 13-46, 13-45, 13-44, 13-43, 13-42, 13-41, 13-40, 13-39, 13-38, 13-37, 13-36, 13-35, 13-34, 13-33, 13-32, 13-31, 13-30, 13-29, 13-28, 13-27, 13-26, 13-25, 13-24, 13-23, 13-22, 13-21, 13-20, 13-19, 13-18, 13-17, 13-16, 13-15, 13-14, 14-49, 14-48, 14-47, 14-46, 14-45, 14-44, 14-43, 14-42, 14-41, 14-40, 14-39, 14-38, 14-37, 14-36, 14-35, 14-34, 14-33, 14-32, 14-31, 14-30, 14-29, 14-28, 14-27, 14-26, 14-25, 14-24, 14-23, 14-22, 14-21, 14-20, 14-19, 14-18, 14-17, 14-16, 14-15, 15-49, 15-48, 15-47, 15-46, 15-45, 15-44, 15-43, 15-42, 15-41, 15-40, 15-39, 15-38, 15-37, 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 15-16,16-49, 16-48, 16-47, 16-46, 16-45, 16-44, 16-43, 16-42, 16-41, 16-40, 16-39, 16-38, 16-37, 16-36, 16-35, 16-34, 16-33, 16-32, 16-31, 16-30, 16-29, 16-28, 16-27, 16-26, 16-25, 16-24, 16-23, 16-22, 16-21, 16-20, 16-19, 16-18, 16-17, 17-49, 17-48, 17-47, 17-46, 17-45, 17-44, 17-43, 17-42, 17-41, 17-40, 17-39, 17-38, 17-37, 17-36, 17-35, 17-34, 17-33, 17-32, 17-31, 17-30, 17-29, 17-28, 17-27, 17-26, 17-25, 17-24, 17-23, 17-22, 17-21, 17-20, 17-19, 17-18, 18-49, 18-48, 18-47, 18-46, 18-45, 18-44, 18-43, 18-42, 18-41, 18-40, 18-39, 18-38, 18-37, 18-36, 18-35, 18-34, 18-33, 18-32, 18-31, 18-30, 18-29, 18-28, 18-27, 18-26, 18-25, 18-24, 18-23, 18-22, 18-21, 18-20, 19-49, 19-48, 19-47, 19-46, 19-45, 19-44, 19-43, 19-42, 19-41, 19-40, 19-39, 19-38, 19-37, 19-36, 19-35, 19-34, 19-33, 19-32, 19-31, 19-30, 19-29, 19-28, 19-27, 19-26, 19-25, 19-24, 19-23, 19-22, 19-21, 19-20, 20-49, 20-48, 20-47, 20-46, 20-45, 20-44, 20-43, 20-42, 20-41, 20-40, 20-39, 20-38, 20-37, 20-36, 20-35, 20-34, 20-33, 20-32, 20-31, 20-30, 20-29, 20-28, 20-27, 20-26, 20-25, 20-24,20-23, 20-22, 20-21, 21-49, 21-48, 21-47, 21-46, 21-45, 21-44, 21-43, 21-42, 21-41, 21-40, 21-39, 21-38, 21-37, 21-36, 21-35, 21-34, 21-33, 21-32, 21-31, 21-30, 21-29, 21-28, 21-27, 21-26, 21-25, 21-24, 21-23, 21-22, 22-49, 22-48, 22-47, 22-46, 22-45, 22-44, 22-43, 22-42, 22-41, 22-40, 22-39, 22-38, 22-37, 22-36, 22-35, 22-34, 22-33, 22-32, 22-31, 22-30, 22-29, 22-28, 22-27, 22-26, 22-25, 22-24, 22-23, 23-49, 23-48, 23-47, 23-46, 23-45, 23-44, 23-43, 23-42, 23-41, 23-40, 23-39, 23-38, 23-37, 23-36, 23-35, 23-34, 23-33, 23-32, 23-31, 23-30, 23-29, 23-28, 23-27, 23-26, 23-25, 23-24, 24-49, 24-48, 24-47, 24-46, 24-45, 24-44, 24-43, 24-42, 24-41, 24-40, 24-39, 24-38, 24-37, 24-36, 24-35, 24-34, 24-33, 24-32, 24-31, 24-30, 24-29, 24-28, 24-27, 24-26, 24-25, 25-49, 25-48, 25-47, 25-46, 25-45, 25-44, 25-43, 25-42, 25-41, 25-40, 25-39, 25-38, 25-37, 25-36, 25-35, 25-34, 25-33, 25-32, 25-31, 25-30, 25-29, 25-28, 25-27, 25-26,26-49, 26-48, 26-47, 26-46, 26-45, 26-44, 26-43, 26-42, 26-41, 26-40, 26-39, 26-38, 26-37, 26-36, 26-35, 26-34, 26-33, 26-32, 26-31, 26-30, 26-29, 26-28, 26-27, 27-49, 27-48, 27-47, 27-46, 27-45, 27-44, 27-43, 27-42, 27-41, 27-40, 27-39, 27-38, 27-37, 27-36, 27-35, 27-34, 27-33, 27-32, 27-31, 27-30, 27-29, 27-28, 28-49, 28-48, 28-47, 28-46, 28-45, 28-44, 28-43, 28-42, 28-41, 28-40, 28-39, 28-38, 28-37, 28-36, 28-35, 28-34, 28-33, 28-32, 28-31, 28-30, 28-29, 29-49, 29-48, 29-47, 29-46, 29-45, 29-44, 29-43, 29-42, 29-41, 29-40, 29-39, 29-38, 29-37, 29-36, 29-35, 29-34, 29-33, 29-32, 29-31, 29-30, 30-49, 30-48, 30-47, 30-46, 30-45, 30-44, 30-43, 30-42, 30-41, 30-40, 30-39, 30-38, 30-37, 30-36, 30-35, 30-34, 30-33, 30-32, or 30-31 nucleotides in length, e.g., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

In some embodiments, an antisense polynucleotide agent may comprise a contiguous nucleotide sequence of no more than 22 nucleotides, e.g., no more than any of 21 nucleotides, 20 nucleotides, 19 nucleotides, no more than 18 nucleotides, 17 nucleotides, 16 nucleotides, 15 nucleotides, or 14 nucleotides. In other embodiments, the antisense polynucleotide agents of the invention are 20 nucleotides in length. In other embodiments, the antisense polynucleotide agents of the invention are 14 nucleotides in length. In certain embodiments, the antisense polynucleotide agents of the invention are at least 12 nucleotides in length.

In one aspect, an antisense polynucleotide agents of the invention include a sequence selected from the group of sequences provided in Table 3. It will be understood that, although some of the sequences in Table 3 are described as modified or conjugated sequences, an antisense polynucleotide agent of the invention, may also comprise any one of the sequences set forth in Table 3 that is un-modified, un-conjugated, or modified or conjugated differently than described therein.

By virtue of the nature of the nucleotide sequences provided in Table 3, antisense polynucleotide agents of the invention may include one of the sequences of Table 3 minus only a few nucleotides on one or both ends and yet remain similarly effective as compared to the antisense polynucleotide agents described above. Hence, antisense polynucleotide agents having a sequence of at least 4, 5, 6, 7, 8, 9, 10, 11, 12, 13, 14, 15, 16, 17, 18, 19, or 20 contiguous nucleotides derived from one of the sequences of Table 3 and differing in their ability to inhibit the expression of a Factor XII gene by not more than 5, 10, 15, 20, 25, or 30% inhibition from an antisense polynucleotide agent comprising the full sequence, are contemplated to be within the scope of the present invention.

In addition, the antisense polynucleotide agents provided in Table 3 identify a region(s) in a Factor XII transcript that is susceptible to antisense inhibition (e.g., the regions encompassed by the start and end positions of the nucleotide sequence of any one of the antisense agents selected from the group consisting of A-145669, A-145668, A-145667, A-145572, A-145567, A-145666, A-145670, A-145674, A-145660, A-145676, A-145539, A-145566, A-145527, A-145548, A-145549, A-145573, A-145661, A-145570, A-145597, A-145600, A-145658; A-145556, A-145656, A-145659, A-145671, A-145675, A-145519, A-145538, A-145619, A-145520, A-145594, A-145540, A-145547, A-145550, A-145551, A-145657, A-145568, A-145575, A-145565, A-145584, A-145616, A-145541, A-145542, A-145555, A-145571, A-145596, A-145599, A-145617, A-145655, A-145663, A-145532, A-145603, A-145665, A-145537, A-145612, A-145651, A-145586; A-145533, A-145569, A-145561, A-145604, A-145506, A-145664, A-145585, A-145595, A-145618, A-145613, A-145615, A-145677, A-145523, A-145552, A-145593, A-145598, A-145633, A-145543, A-145557, A-145624, A-145629, A-145646, A-145512, A-145536, A-145583, A-145625, A-145576, A-145623, A-145626; A-145562, A-145577, A-145588, A-145650, A-145534, A-145601, A-145662, A-145522, A-145525, A-145589, A-145607, A-145516, A-145529, A-145564, A-145605, A-145495, A-145496, A-145507, A-145614, A-145637, A-145497, A-145526, A-145591, A-145628, A-145647, A-145498, A-145501, A-145508, A-145560, A-145590, A-145611, A-145627, A-145652, A-145672, A-145513, A-145563, A-145581, A-145553, and A-145587 in Table 3). As such, the present invention further features antisense polynucleotide agents that target within one of these sites. As used herein, an antisense polynucleotide agent is said to target within a particular site of an RNA transcript if the antisense polynucleotide agent promotes antisense inhibition of the target at that site. Such an antisense polynucleotide agent will generally include at least 14 contiguous nucleotides from one of the sequences provided in Table 3 coupled to additional nucleotide sequences taken from the region contiguous to the selected sequence in a Factor XII gene.

While a target sequence is generally 4-50 nucleotides in length, there is wide variation in the suitability of particular sequences in this range for directing antisense inhibition of any given target RNA. Various software packages and the guidelines set out herein provide guidance for the identification of optimal target sequences for any given gene target, but an empirical approach can also be taken in which a "window" or "mask" of a given size (as a non-limiting example, 20 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an antisense polynucleotide agent, mediate the best inhibition of target gene expression. Thus, while the sequences identified, for example, in Table 3 represent effective target sequences, it is contemplated that further optimization of antisense inhibition efficiency can be achieved by progressively "walking the window" one nucleotide upstream or downstream of the given sequences to identify sequences with equal or better inhibition characteristics.

Further, it is contemplated that for any sequence identified, e.g., in Table 3, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of antisense polynucleotide agents based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in length, or other modifications as known in the art or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

III. Modified Antisense Polynucleotide Agents of the Invention

In some embodiments, the nucleotides of an antisense polynucleotide agent of the invention is un-modified, and does not comprise, e.g., chemical modifications or conjugations known in the art and described herein. In another embodiment, at least one of the nucleotides of an antisense polynucleotide agent of the invention is chemically modified to enhance stability or other beneficial characteristics. In certain embodiments of the invention, substantially all of the nucleotides of an antisense polynucleotide agent of the invention are modified. In other embodiments of the invention, all of the nucleotides of an antisense polynucleotide agent of the invention are modified. Antisense polynucleotide agents of the invention in which "substantially all of the nucleotides are modified" are largely but not wholly modified and can include not more than 5, 4, 3, 2, or 1 unmodified nucleotides.

The nucleic acids featured in the invention can be synthesized or modified by standard methods known in the art as further discussed below, e.g., solution-phase or solid-phase organic synthesis or both, e.g., by use of an automated DNA synthesizer, such as are commercially available from, for example, Biosearch, Applied Biosystems, Inc. Well-established methods for the synthesis or modification of the nucleic acids featured in the invention are described in, for example, "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages.

Specific examples of modified nucleotides useful in the embodiments described herein include, but are not limited to nucleotides containing modified backbones or no natural internucleoside linkages. Nucleotides having modified backbones include, among others, those that do not have a phosphorus atom in the backbone. For the purposes of this specification, and as sometimes referenced in the art, modified nucleotides that do not have a phosphorus atom in their internucleoside backbone can also be considered to be oligonucleosides. In some embodiments, a modified antisense polynucleotide agent will have a phosphorus atom in its internucleoside backbone.

Modified nucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6, 239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and U.S. Pat. RE39464, the entire contents of each of which are hereby incorporated herein by reference.

Modified nucleotide backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable nucleotide mimetics are contemplated for use in antisense polynucleotide agents, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the antisense polynucleotide agents of the invention are described in, for example, in Nielsen et al., *Science,* 1991, 254, 1497-1500.

Some embodiments featured in the invention include polynucleotides with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—and —N($CH_3$)—$CH_2$—$CH_2$— [wherein the native phosphodiester backbone is represented as —O—P—O—$CH_2$—] of the above-referenced U.S. Pat. No. 5,489, 677, and the amide backbones of the above-referenced U.S. Pat. No. 5,602,240. In some embodiments, the antisense polynucleotide agents featured herein have morpholino backbone structures of the above-referenced U.S. Pat. No. 5,034,506.

Modified nucleotides can also contain one or more modified or substituted sugar moieties. The antisense polynucleotide agents featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$ $CH_3$, O($CH_2$)$_n$OCH$_3$, O($CH_2$)$_n$NH$_2$, O($CH_2$)$_n$CH$_3$, O($CH_2$)$_n$ ONH$_2$, and O($CH_2$)$_n$ON[($CH_2$)$_n$CH$_3$)]$_2$, where n and m are from 1 to 10.

In other embodiments, antisense polynucleotide agents include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an antisense polynucleotide, or a group for improving the pharmacodynamic properties of an antisense polynucleotide agent, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., *Helv. Chin. Acta,* 1995, 78:486-504) i.e., an alkoxyalkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other modifications include 2'-methoxy (2'-OCH$_3$), 2'-aminopropoxy (2'-OCH$_2$CH$_2$CH$_2$NH$_2$) and 2'-fluoro (2'-F) Similar modifications can also be made at other positions on a nucleotide of an antisense polynucleotide agent, particularly the 3' position of the sugar on the 3' terminal nucleotide. Antisense polynucleotide agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

Additional nucleotides having modified or substituted sugar moieties for use in the polynucleotide agents of the invention include nucleotides comprising a bicyclic sugar. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an antisense polynucleotide agent may include one or more locked nucleic acids. A "locked nucleic acid" ("LNA") is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH$_2$—O-2' bridge. This structure effectively "locks" the ribose in the 3'-endo structural conformation. The addition of locked nucleic acids to santisense polynucleotide agents has been shown to increase santisense polynucleotide agent stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.,* 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

In one particular embodiment of the invention, an antisense polynucleotide agent can include one or more constrained ethyl nucleotides. As used herein, a "constrained ethyl nucleotide" or "cEt" is a locked nucleic acid comprising a bicyclic sugar moiety comprising a 4'-CH(CH$_3$)—O-2' bridge. In one embodiment, a constrained ethyl nucleotide is in an S conformation and is referred to as an "S-constrained ethyl nucleotide" or "S-cEt."

Modified nucleotides included in the antisense polynucleotide agents of the invention can also contain one or more sugar mimetics. For example, the antisense polynucleotide agent may include a "modified tetrahydropyran nucleotide" or "modified THP nucleotide." A "modified tetrahydropyran nucleotide" has a six-membered tetrahydropyran "sugar" substituted in for the pentofuranosyl residue in normal nucleotides (a sugar surrogate). Modified THP nucleotides include, but are not limited to, what is referred to in the art as hexitol nucleic acid (HNA), anitol nucleic acid (ANA), manitol nucleic acid (MNA) (see, e.g., Leumann, *Bioorg. Med. Chem.,* 2002, 10, 841-854), or fluoro HNA (F-HNA).

In some embodiments of the invention, sugar surrogates comprise rings having more than 5 atoms and more than one heteroatom. For example nucleotides comprising morpholino sugar moieties and their use in oligomeric compounds has been reported (see for example: Braasch et al., *Biochemistry,* 2002, 41, 4503-4510; and U.S. Pat. Nos. 5,698,685; 5,166,315; 5,185,444; and 5,034,506). Morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH2-0-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., J. Am. Chem. Soc., 2008, 130(6), 1979-1984; Horvath et al., Tetrahedron Letters, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J. Org. Chem., 2001, 66, 8478-82; Wang et al., Nucleosides, Nucleotides & Nucleic Acids, 2001, 20(4-7), 785-788; Wang et al., J. Am. Chem., 2000, 122, 8595-8602; Published PCT application, WO 06/047842; and Published PCT Application WO 01/049687; the text of each is incorporated by reference herein, in their entirety).

An antisense polynucleotide agent can also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in "Modified Nucleosides in Biochemistry," *Biotechnology and Medicine*, Herdewijn, P. ed. Wiley-VCH, 2008; those disclosed in *The Concise Encyclopedia Of Polymer Science And Engineering*, pages 858-859, Kroschwitz, J. L, ed. John Wiley & Sons, 1990, these disclosed by Englisch et al., *Angewandte Chemie, International Edition*, 1991, 30, 613, and those disclosed by Sanghvi, Y S., Chapter 15, *antisense polynucleotide agent Research and Applications, pages* 289-302, Crooke, S. T. and Lebleu, B., Ed., CRC Press, 1993. Certain of these nucleobases are particularly useful for increasing the binding affinity of the agents featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., *antisense polynucleotide agent Research and Applications*, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification. Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Additional modification which may potentially stabilize the ends of antisense polynucleotide agents can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in US20120142101.

Any of the antisense polynucleotide agents of the invention may be optionally conjugated with a GalNAc derivative ligand, as described below.

As described in more detail below, an agent that contains conjugations of one or more carbohydrate moieties to an antisense polynucleotide agent can optimize one or more properties of the agent. In many cases, the carbohydrate moiety will be attached to a modified subunit of the antisense polynucleotide agent. For example, the ribose sugar of one or more ribonucleotide subunits of an agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The antisense polynucleotide agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the antisense polynucleotide agent for use in the methods of the invention is an agent selected from the group of agents listed in Table 3. These agents may further comprise a ligand, as described below.

A. Antisense Polynucleotide Agents Comprising Motifs

In certain embodiments of the invention, at least one of the contiguous nucleotides of the antisense polynucleotide agents of the invention may be a modified nucleotide. In one embodiment, the modified nucleotide comprises one or more modified sugars. In other embodiments, the modified nucleotide comprises one or more modified nucleobases. In yet other embodiments, the modified nucleotide comprises one or more modified internucleoside linkages. In some embodiments, the modifications (sugar modifications, nucleobase modifications, or linkage modifications) define a pattern or motif. In one embodiment, the patterns of modifications of sugar moieties, internucleoside linkages, and nucleobases are each independent of one another.

Antisense polynucleotide agents having modified oligonucleotides arranged in patterns, or motifs may, for example, confer to the agents properties such as enhanced inhibitory activity, increased binding affinity for a target nucleic acid, or resistance to degradation by in vivo nucleases. For example, such agents may contain at least one region modified so as to confer increased resistance to nuclease degradation, increased cellular uptake, increased binding affinity for the target nucleic acid, or increased inhibitory activity. A second region of such agents may optionally serve as a substrate for the cellular endonuclease RNase H, which cleaves the RNA strand of an RNA:DNA duplex.

An exemplary antisense polynucleotide agent having modified oligonucleotides arranged in patterns, or motifs is a gapmer. In a "gapmer", an internal region or "gap" having a plurality of linked nucleotides that supports RNaseH cleavage is positioned between two external flanking regions or "wings" having a plurality of linked nucleotides that are chemically distinct from the linked nucleotides of the internal region. The gap segment generally serves as the substrate for endonuclease cleavage, while the wing segments comprise modified nucleotides.

The three regions of a gapmer motif (the 5'-wing, the gap, and the 3'-wing) form a contiguous sequence of nucleotides and may be described as "X-Y-Z", wherein "X" represents the length of the 5-wing, "Y" represents the length of the gap, and "Z" represents the length of the 3'-wing. In one embodiment, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different.

In certain embodiments, the regions of a gapmer are differentiated by the types of modified nucleotides in the region. The types of modified nucleotides that may be used to differentiate the regions of a gapmer, in some embodiments, include β-D-ribonucleotides, β-D-deoxyribonucleotides, 2'-modified nucleotides, e.g., 2'-modified nucleotides (e.g., 2'-MOE, and 2'-O—CH3), and bicyclic sugar modified nucleotides (e.g., those having a 4'-(CH2)n-O-2' bridge, where n=1 or n=2).

In one embodiment, at least some of the modified nucleotides of each of the wings may differ from at least some of the modified nucleotides of the gap. For example, at least some of the modified nucleotides of each wing that are closest to the gap (the 3'-most nucleotide of the 5'-wing and the 5'-most nucleotide of the 3-wing) differ from the modified nucleotides of the neighboring gap nucleotides, thus defining the boundary between the wings and the gap. In certain embodiments, the modified nucleotides within the gap are the same as one another. In certain embodiments, the gap includes one or more modified nucleotides that differ from the modified nucleotides of one or more other nucleotides of the gap.

The length of the 5'-wing (X) of a gapmer may be 1 to 6 nucleotides in length, e.g., 2 to 6, 2 to 5, 3 to 6, 3 to 5, 1 to 5, 1 to 4, 1 to 3, 2 to 4 nucleotides in length, e.g., 1, 2, 3, 4, 5, or 6 nucleotides in length.

The length of the 3'-wing (Z) of a gapmer may be 1 to 6 nucleotides in length, e.g., 2 to 6, 2-5, 3 to 6, 3 to 5, 1 to 5, 1 to 4, 1 to 3, 2 to 4 nucleotides in length, e.g., 1, 2, 3, 4, 5, or 6 nucleotides in length.

The length of the gap (Y) of a gapmer may be 5 to 14 nucleotides in length, e.g., 5 to 13, 5 to 12, 5 to 11, 5 to 10, 5 to 9, 5 to 8, 5 to 7, 5 to 6, 6 to 14, 6 to 13, 6 to 12, 6 to 11, 6 to 10, 6 to 9, 6 to 8, 6 to 7, 7 to 14, 7 to 13, 7 to 12, 7 to 11, 7 to 10, 7 to 9, 7 to 8, 8 to 14, 8 to 13, 8 to 12, 8 to 11, 8 to 10, 8 to 9, 9 to 14, 9 to 13, 9 to 12, 9 to 11, 9 to 10, 10 to 14, 10 to 13, 10 to 12, 10 to 11, 11 to 14, 11 to 13, 11 to 12, 12 to 14, 12 to 13, or 13 to 14 nucleotides in length, e.g., 5, 6, 7, 8, 9, 10, 11, 12, 13, or 14 nucleotides in length.

In some embodiments of the invention X consists of 2, 3, 4, 5 or 6 nucleotides, Y consists of 7, 8, 9, 10, 11, or 12 nucleotides, and Z consists of 2, 3, 4, 5 or 6 nucleotides. Such gapmers include (X-Y-Z) 2-7-2, 2-7-3, 2-7-4, 2-7-5, 2-7-6, 3-7-2, 3-7-3, 3-7-4, 3-7-5, 3-7-6, 4-7-3, 4-7-4, 4-7-5, 4-7-6, 5-7-3, 5-7-4, 5-7-5, 5-7-6, 6-7-3, 6-7-4, 6-7-5, 6-7-6, 3-7-3, 3-7-4, 3-7-5, 3-7-6, 4-7-3, 4-7-4, 4-7-5, 4-7-6, 5-7-3, 5-7-4, 5-7-5, 5-7-6, 6-7-3, 6-7-4, 6-7-5, 6-7-6, 2-8-2, 2-8-3, 2-8-4, 2-8-5, 2-8-6, 3-8-2, 3-8-3, 3-8-4, 3-8-5, 3-8-6, 4-8-3, 4-8-4, 4-8-5, 4-8-6, 5-8-3, 5-8-4, 5-8-5, 5-8-6, 6-8-3, 6-8-4, 6-8-5, 6-8-6, 2-9-2, 2-9-3, 2-9-4, 2-9-5, 2-9-6, 3-9-2, 3-9-3, 3-9-4, 3-9-5, 3-9-6, 4-9-3, 4-9-4, 4-9-5, 4-9-6, 5-9-3, 5-9-4, 5-9-5, 5-9-6, 6-9-3, 6-9-4, 6-9-5, 6-9-6, 2-10-2, 2-10-3, 2-10-4, 2-10-5, 2-10-6, 3-10-2, 3-10-3, 3-10-4, 3-10-5, 3-10-6, 4-10-3, 4-10-4, 4-10-5, 4-10-6, 5-10-3, 5-10-4, 5-10-5, 5-10-6, 6-10-3, 6-10-4, 6-10-5, 6-10-6, 2-11-2, 2-11-3, 2-11-4, 2-11-5, 2-11-6, 3-11-2, 3-11-3, 3-11-4, 3-11-5, 3-11-6, 4-11-3, 4-11-4, 4-11-5, 4-11-6, 5-11-3, 5-11-4, 5-11-5, 5-11-6, 6-11-3, 6-11-4, 6-11-5, 6-11-6, 2-12-2, 2-12-3, 2-12-4, 2-12-5, 2-12-6, 3-12-2, 3-12-3, 3-12-4, 3-12-5, 3-12-6, 4-12-3, 4-12-4, 4-12-5, 4-12-6, 5-12-3, 5-12-4, 5-12-5, 5-12-6, 6-12-3, 6-12-4, 6-12-5, or 6-12-6.

In some embodiments of the invention, antisense polynucleotide agents targeting Factor XII include a 5-10-5 gapmer motif. In other embodiments of the invention, antisense polynucleotide agents targeting Factor XII include a 4-10-4 gapmer motif. In another embodiment of the invention, antisense polynucleotide agents targeting Factor XII include a 3-10-3 gapmer motif. In yet other embodiments of the invention, antisense polynucleotide agents targeting Factor XII include a 2-10-2 gapmer motif.

The 5'-wing or 3'-wing of a gapmer may independently include 1-6 modified nucleotides, e.g., 1, 2, 3, 4, 5, or 6 modified nucleotides.

In some embodiment, the 5'-wing of a gapmer includes at least one modified nucleotide. In one embodiment, the 5'-wing of a gapmer comprises at least two modified nucleotides. In another embodiment, the 5'-wing of a gapmer comprises at least three modified nucleotides. In yet another embodiment, the 5'-wing of a gapmer comprises at least four modified nucleotides. In another embodiment, the 5'-wing of a gapmer comprises at least five modified nucleotides. In certain embodiments, each nucleotide of the 5'-wing of a gapmer is a modified nucleotide.

In some embodiments, the 3'-wing of a gapmer includes at least one modified nucleotide. In one embodiment, the 3'-wing of a gapmer comprises at least two modified nucleotides. In another embodiment, the 3'-wing of a gapmer comprises at least three modified nucleotides. In yet another embodiment, the 3'-wing of a gapmer comprises at least four modified nucleotides. In another embodiment, the 3'-wing of a gapmer comprises at least five modified nucleotides. In certain embodiments, each nucleotide of the 3'-wing of a gapmer is a modified nucleotide.

In certain embodiments, the regions of a gapmer are differentiated by the types of sugar moieties of the nucleotides. In one embodiment, the nucleotides of each distinct region comprise uniform sugar moieties. In other embodiments, the nucleotides of each distinct region comprise different sugar moieties. In certain embodiments, the sugar nucleotide modification motifs of the two wings are the same as one another. In certain embodiments, the sugar nucleotide modification motifs of the 5'-wing differs from the sugar nucleotide modification motif of the 3'-wing.

The 5'-wing of a gapmer may include 1-6 modified nucleotides, e.g., 1, 2, 3, 4, 5, or 6 modified nucleotides.

In one embodiment, at least one modified nucleotide of the 5'-wing of a gapmer is a bicyclic nucleotide, such as a constrained ethyl nucleotide, or an LNA. In another embodiment, the 5'-wing of a gapmer includes 2, 3, 4, or 5 bicyclic nucleotides. In some embodiments, each nucleotide of the 5'-wing of a gapmer is a bicyclic nucleotide.

In one embodiment, the 5'-wing of a gapmer includes at least 1, 2, 3, 4, or 5 constrained ethyl nucleotides. In some embodiments, each nucleotide of the 5'-wing of a gapmer is a constrained ethyl nucleotide.

In one embodiment, the 5'-wing of a gapmer comprises at least one LNA nucleotide. In another embodiment, the 5'-wing of a gapmer includes 2, 3, 4, or 5 LNA nucleotides. In other embodiments, each nucleotide of the 5'-wing of a gapmer is an LNA nucleotide.

In certain embodiments, at least one modified nucleotide of the 5'-wing of a gapmer is a non-bicyclic modified nucleotide, e.g., a 2'-substituted nucleotide. A "2'-substituted nucleotide" is a nucleotide comprising a modification at the 2'-position which is other than H or OH, such as a 2'-OMe nucleotide, or a 2'-MOE nucleotide. In one embodiment, the 5'-wing of a gapmer comprises 2, 3, 4, or 5 2'-substituted nucleotides. In one embodiment, each nucleotide of the 5'-wing of a gapmer is a 2'-substituted nucleotide.

In one embodiment, the 5'-wing of a gapmer comprises at least one 2'-OMe nucleotide. In one embodiment, the 5'-wing of a gapmer comprises at least 2, 3, 4, or 5 2'-OMe nucleotides. In one embodiment, each of the nucleotides of the 5'-wing of a gapmer comprises a 2'-OMe nucleotide.

In one embodiment, the 5'-wing of a gapmer comprises at least one 2'-MOE nucleotide. In one embodiment, the 5'-wing of a gapmer comprises at least 2, 3, 4, or 5 2'-MOE nucleotides. In one embodiment, each of the nucleotides of the 5'-wing of a gapmer comprises a 2'-MOE nucleotide.

In certain embodiments, the 5'-wing of a gapmer comprises at least one 2'-deoxynucleotide. In certain embodiments, each nucleotide of the 5'-wing of a gapmer is a 2'-deoxynucleotide. In a certain embodiments, the 5'-wing of a gapmer comprises at least one ribonucleotide. In certain embodiments, each nucleotide of the 5'-wing of a gapmer is a ribonucleotide.

The 3'-wing of a gapmer may include 1-6 modified nucleotides, e.g., 1, 2, 3, 4, 5, or 6 modified nucleotides.

In one embodiment, at least one modified nucleotide of the 3'-wing of a gapmer is a bicyclic nucleotide, such as a constrained ethyl nucleotide, or an LNA. In another embodiment, the 3'-wing of a gapmer includes 2, 3, 4, or 5 bicyclic nucleotides. In some embodiments, each nucleotide of the 3'-wing of a gapmer is a bicyclic nucleotide.

In one embodiment, the 3'-wing of a gapmer includes at least one constrained ethyl nucleotide. In another embodiment, the 3'-wing of a gapmer includes 2, 3, 4, or 5 constrained ethyl nucleotides. In some embodiments, each nucleotide of the 3'-wing of a gapmer is a constrained ethyl nucleotide.

In one embodiment, the 3'-wing of a gapmer comprises at least one LNA nucleotide. In another embodiment, the 3'-wing of a gapmer includes 2, 3, 4, or 5 LNA nucleotides. In other embodiments, each nucleotide of the 3'-wing of a gapmer is an LNA nucleotide.

In certain embodiments, at least one modified nucleotide of the 3'-wing of a gapmer is a non-bicyclic modified nucleotide, e.g., a 2'-substituted nucleotide. In one embodiment, the 3'-wing of a gapmer comprises 2, 3, 4, or 5 2'-substituted nucleotides. In one embodiment, each nucleotide of the 3'-wing of a gapmer is a 2'-substituted nucleotide.

In one embodiment, the 3'-wing of a gapmer comprises at least one 2'-OMe nucleotide. In one embodiment, the 3'-wing of a gapmer comprises at least 2, 3, 4, or 5 2'-OMe nucleotides. In one embodiment, each of the nucleotides of the 3'-wing of a gapmer comprises a 2'-OMe nucleotide.

In one embodiment, the 3'-wing of a gapmer comprises at least one 2'-MOE nucleotide. In one embodiment, the 3'-wing of a gapmer comprises at least 2, 3, 4, or 5 2'-MOE nucleotides. In one embodiment, each of the nucleotides of the 3'-wing of a gapmer comprises a 2'-MOE nucleotide.

In certain embodiments, the 3'-wing of a gapmer comprises at least one 2'-deoxynucleotide. In certain embodiments, each nucleotide of the 3'-wing of a gapmer is a 2'-deoxynucleotide. In a certain embodiments, the 3'-wing of a gapmer comprises at least one ribonucleotide. In certain embodiments, each nucleotide of the 3'-wing of a gapmer is a ribonucleotide.

The gap of a gapmer may include 5-14 modified nucleotides, e.g., 5, 6, 7, 8, 9, 10, 11, 12, 13, or 14 modified nucleotides.

In one embodiment, the gap of a gapmer comprises at least one 5-methylcytosine. In one embodiment, the gap of a gapmer comprises at least 2, 3, 4, 5, 6, 7, 8, 9, 10, 11, 12, or 13 5-methylcytosines. In one embodiment, all of the nucleotides of the the gap of a gapmer are 5-methylcytosines.

In one embodiment, the gap of a gapmer comprises at least one 2'-deoxynucleotide. In one embodiment, the gap of a gapmer comprises at least 2, 3, 4, 5, 6, 7, 8, 9, 10, 11, 12, or 13 2'-deoxynucleotides. In one embodiment, all of the nucleotides of the the gap of a gapmer are 2'-deoxynucleotides.

A gapmer may include one or more modified internucleotide linkages. In some embodiments, a gapmer includes one or more phosphodiester internucleotide linkages. In other embodiments, a gapmer includes one or more phosphorothioate internucleotide linkages.

In one embodiment, each nucleotide of a 5'-wing of a gapmer are linked via a phosphorothioate internucleotide linkage. In another embodiment, each nucleotide of a 3'-wing of a gapmer are linked via a phosphorothioate internucleotide linkage. In yet another embodiment, each nucleotide of a gap segment of a gapmer is linked via a phosphorothioate internucleotide linkage. In one embodiment, all of the nucleotides in a gapmer are linked via phosphorothioate internucleotide linkages.

In one embodiment, an antisense polynucleotide agent targeting a Factor XII gene comprises a gap segment of ten 2'-deoxyribonucleotides positioned immediately adjacent to and between a 5'-wing segment comprising five nucleotides and a 3'-wing segment comprising 5 nucleotides.

In another embodiment, an antisense polynucleotide agent targeting a Factor XII gene comprises a gap segment of ten 2'-deoxyribonucleotides positioned immediately adjacent to and between a 5'-wing segment comprising four nucleotides and a 3'-wing segment comprising four nucleotides.

In another embodiment, an antisense polynucleotide agent targeting a Factor XII gene comprises a gap segment of ten 2'-deoxyribonucleotides positioned immediately adjacent to and between a 5'-wing segment comprising three nucleotides and a 3'-wing segment comprising three nucleotides.

In another embodiment, an antisense polynucleotide agent targeting a Factor XII gene comprises a gap segment of ten 2'-deoxyribonucleotides positioned immediately adjacent to and between a 5'-wing segment comprising two nucleotides and a 3'-wing segment comprising two nucleotides.

In one embodiment, each nucleotide of a 5-wing flanking a gap segment of 10 2'-deoxyribonucleotides comprises a modified nucleotide. In another embodiment, each nucleotide of a 3-wing flanking a gap segment of 10 2'-deoxyribonucleotides comprises a modified nucleotide. In one embodiment, each of the modified 5'-wing nucleotides and each of the modified 3'-wing nucleotides comprise a 2'-sugar modification. In one embodiment, the 2'-sugar modification is a 2'-OMe modification. In another embodiment, the 2'-sugar modification is a 2'-MOE modification. In one embodiment, each of the modified 5'-wing nucleotides and each of the modified 3'-wing nucleotides comprise a bicyclic nucleotide. In one embodiment, the bicyclic nucleotide is a constrained ethyl nucleotide. In another embodiment, the bicyclic nucleotide is an LNA nucleotide. In one embodiment, each cytosine in an antisense polynucleotide agent targeting a Factor XII gene is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising five nucleotides comprising a 2'OMe modification and a 3'-wing segment comprising five nucleotides comprising a 2'OMe modification, wherein each internucleotde linkage of the agent is a phosphorothioate linkage. In one embodiment, each cytosine of the agent is a 5-methylcytosine. In some embodiments, the agent further comprises a ligand.

In one embodiment, an antisense polynucleotide agent targeting a Factor XII gene comprises a gap segment of ten 2'-deoxyribonucleotides positioned immediately adjacent to and between a 5'-wing segment comprising five nucleotides comprising a 2'MOE modification and a 3'-wing segment comprising five nucleotides comprising a 2'MOE modification, wherein each internucleotide linkage of the agent is a phosphorothioate linkage. In one embodiment, each cytosine of the agent is a 5-methylcytosine. In some embodiments, the agent further comprises a ligand.

In one embodiment, an antisense polynucleotide agent targeting a Factor XII gene comprises a gap segment of ten 2'-deoxyribonucleotides positioned immediately adjacent to and between a 5'-wing segment comprising five constrained ethyl nucleotides and a 3'-wing segment comprising five constrained ethyl nucleotides, wherein each internucleoitde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising five LNA nucleotides and a 3'-wing segment comprising five LNA nucleotides, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising four nucleotides comprising a 2'OMe modification and a 3'-wing segment comprising four nucleotides comprising a 2'OMe modification, wherein each internucleotde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising four nucleotides comprising a 2'MOE modification and a 3'-wing segment comprising four nucleotides comprising a 2'MOE modification, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising four constrained ethyl nucleotides and a 3'-wing segment comprising four constrained ethyl nucleotides, wherein each internucleoitde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising four LNA nucleotides and a 3'-wing segment comprising four LNA nucleotides, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising three nucleotides comprising a 2'OMe modification and a 3'-wing segment comprising three nucleotides comprising a 2'OMe modification, wherein each internucleotde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising three nucleotides comprising a 2'MOE modification and a 3'-wing segment comprising three nucleotides comprising a 2'MOE modification, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising three constrained ethyl nucleotides and a 3'-wing segment comprising three constrained ethyl nucleotides, wherein each internucleoitde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising three LNA nucleotides and a 3'-wing segment comprising three LNA nucleotides, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising two nucleotides comprising a 2'OMe modification and a 3'-wing segment comprising two nucleotides comprising a 2'OMe modification, wherein each internucleotde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising two nucleotides comprising a 2'MOE modification and a 3'-wing segment comprising two nucleotides comprising a 2'MOE modification, wherein each internucleotide linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising two constrained ethyl nucleotides and a 3'-wing segment comprising two constrained ethyl nucleotides, wherein each internucleoitde linkage of the agent is a phosphorothioate linkage. In some embodiments, each cytosine of the agent is a 5-methylcytosine.

In one embodiment, an antisense polynucleotide agent targeting a Factor XII gene comprises a gap segment of ten 2'-deoxyribonucleotides positioned immediately adjacent to and between a 5'-wing segment comprising two LNA nucleotides and a 3'-wing segment comprising two LNA nucleotides, wherein each internucleotide linkage of the agent is a phosphorothioate linkage. In some embodiments, each cytosine of the agent is a 5-methylcytosine.

Further gapmer designs suitable for use in the agents, compositions, and methods of the invention are disclosed in, for example, U.S. Pat. Nos. 7,687,617 and 8,580,756; U.S. Patent Publication Nos. 20060128646, 20090209748, 20140128586, 20140128591, 20100210712, and 20080015162A1; and International Publication No. WO 2013/159108, the entire content of each of which are incorporated herein by reference.

IV. Antisense Polynucleotide Agents Conjugated to Ligands

Another modification of the polynucleotide agents of the invention involves chemically linking to the agent one or more ligands, moieties, or conjugates that enhance the activity, cellular distribution, or cellular uptake of the antisense polynucleotide agent. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethylammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In one embodiment, a ligand alters the distribution, targeting, or lifetime of an antisense polynucleotide agent into which it is incorporated. In preferred embodiments a ligand provides an enhanced affinity for a selected target, e.g., molecule, cell, or cell type; compartment, e.g., a cellular or organ compartment, tissue, organ, or region of the body, as, e.g., compared to a species absent such a ligand. Preferred ligands will not take part in hybridization of an antisense polynucleotide agent to the targeted mRNA.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid, or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the antisense polynucleotide agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, jasplakinolide, latrunculin A, phalloidin, swinholide A, indanocine, or myoservin.

In some embodiments, a ligand attached to an antisense polynucleotide agent as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated polynucleotides of the invention may be synthesized by the use of a polynucleotide that bears a pendant reactive functionality, such as that derived from the attachment of a linking molecule onto the oligonucleotide (described below). This reactive polynucleotide may be reacted directly with commercially-available ligands, ligands that are synthesized bearing any of a variety of protecting groups, or ligands that have a linking moiety attached thereto.

The polynucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other polynucleotides, such as the phosphorothioates and alkylated derivatives.

In the ligand-conjugated polynucleotides and ligand-molecule bearing sequence-specific linked nucleosides of the present invention, the polynucleotides and polynucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the polynucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to antisense polynucleotide agents can affect pharmacokinetic distribution of the agent, such as by enhancing cellular recognition and absorption. The peptide or peptidomimetic moiety can be 5-50 amino acids long, e.g., 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 5). An RFGF analogue (e.g., amino acid sequence AALLPVL-LAAP (SEQ ID NO: 6) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 7) and the *Drosophila* Antennapedia protein (RQIKIWFQ-NRRMKWKK (SEQ ID NO: 8) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an antisens epolynucleotide agent via an incorporated monomer unit for cell targeting purposes is an arginine-glycine-aspartic acid (RGD)-peptide, or RGD mimic. A peptide moiety can range in length from 5 amino acids to 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an antisense polynucleotide agent further comprises a carbohydrate. The carbohydrate conjugated agents are advantageous for the in vivo delivery of nucleic acids, as well as compositions suitable for in vivo therapeutic use, as described herein (see, e.g., Prakash, et al. (2014) *Nuc Acid Res* doi 10.1093/nar/gku531). As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as

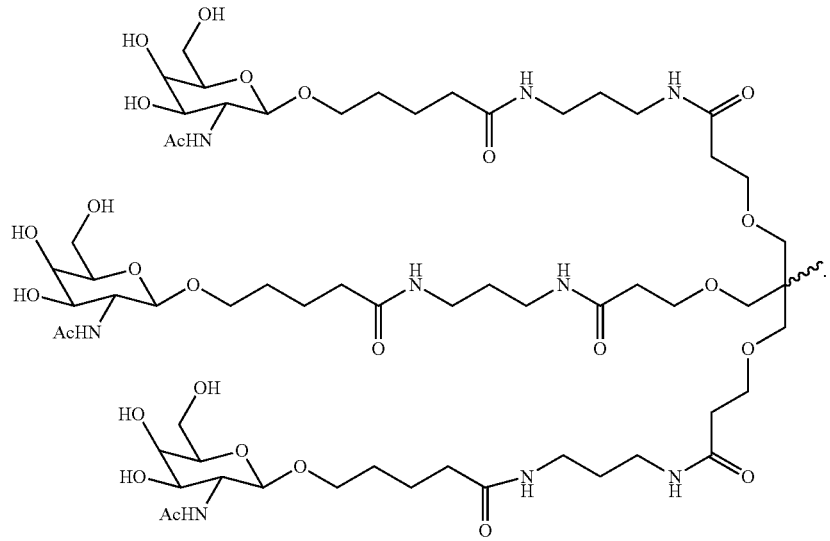

Formula II

In another embodiment, a carbohydrate conjugate for use in the compositions and methods of the invention is selected from the group consisting of:
Formula II
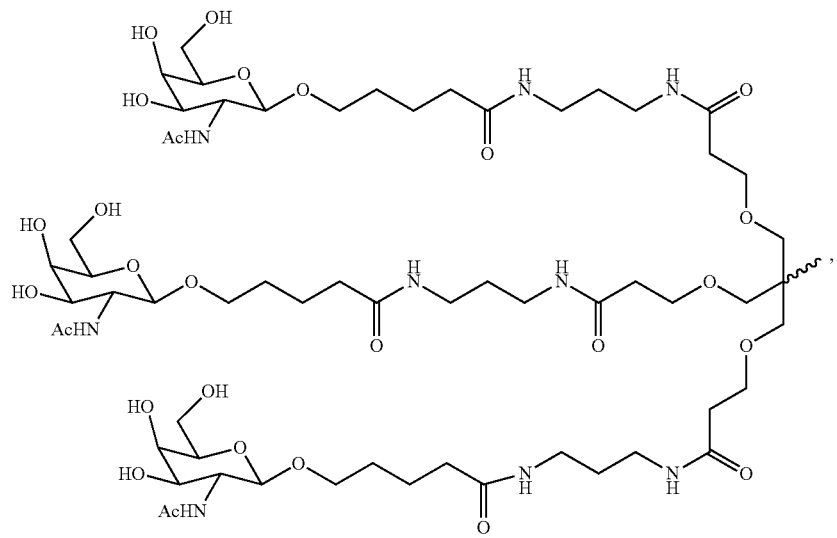
Formula III
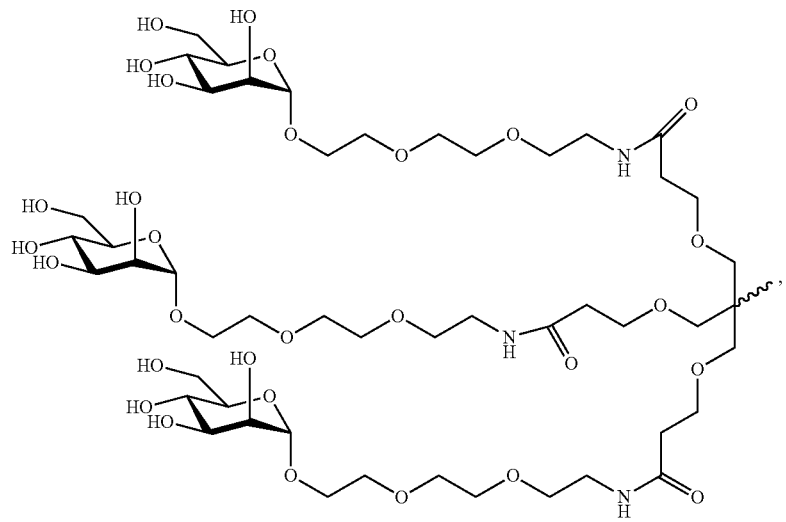
Formula IV
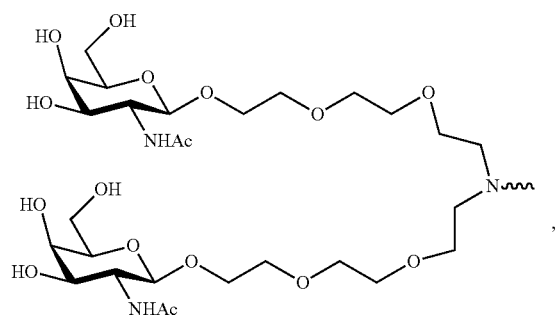
Formula V
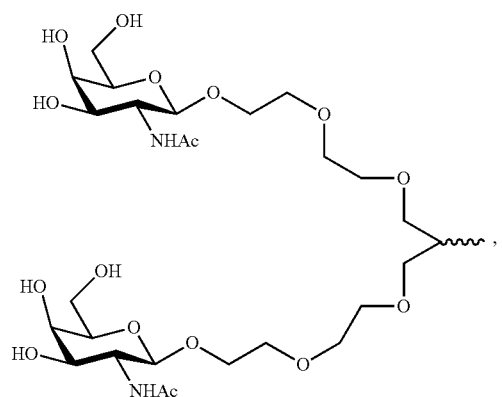

Formula VI
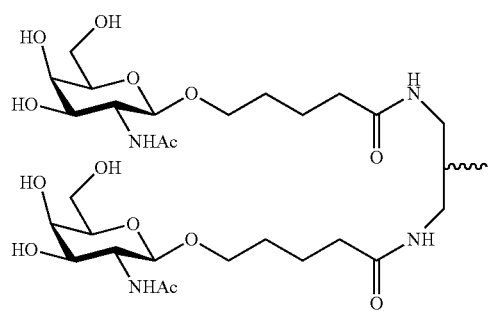
Formula VII
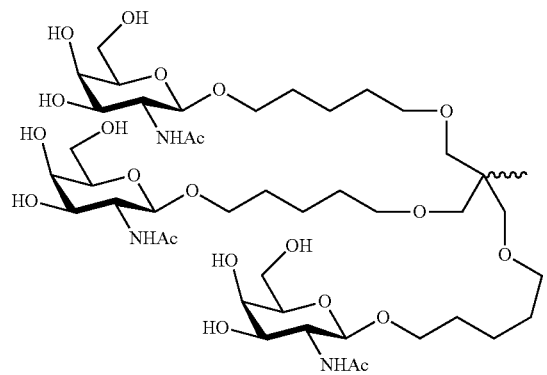
Formula VIII
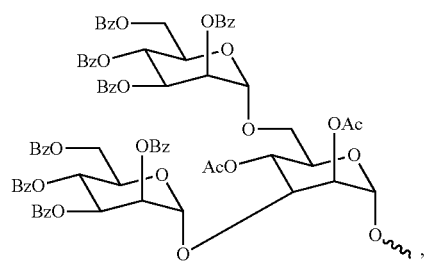
Formula IX
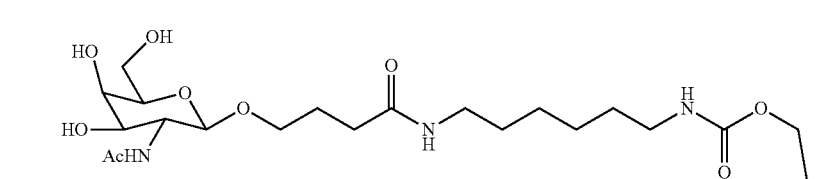
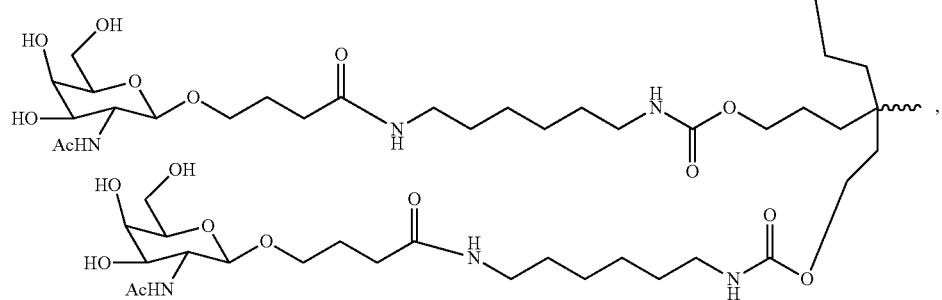

-continued
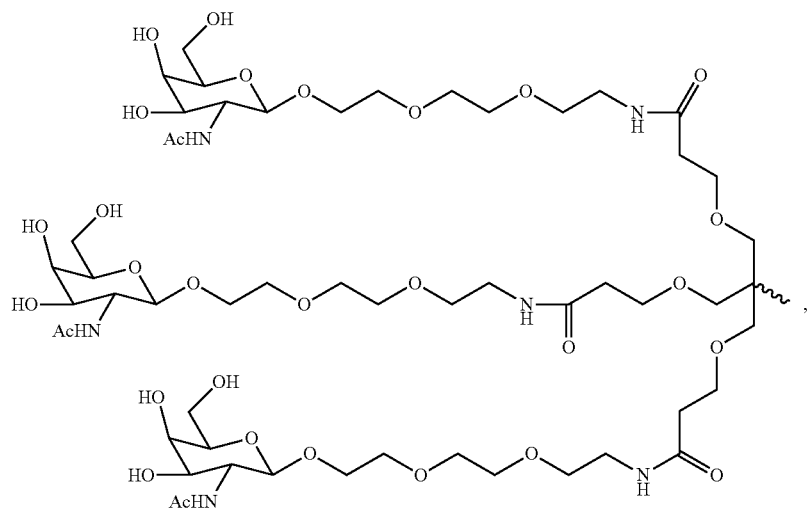
Formula X
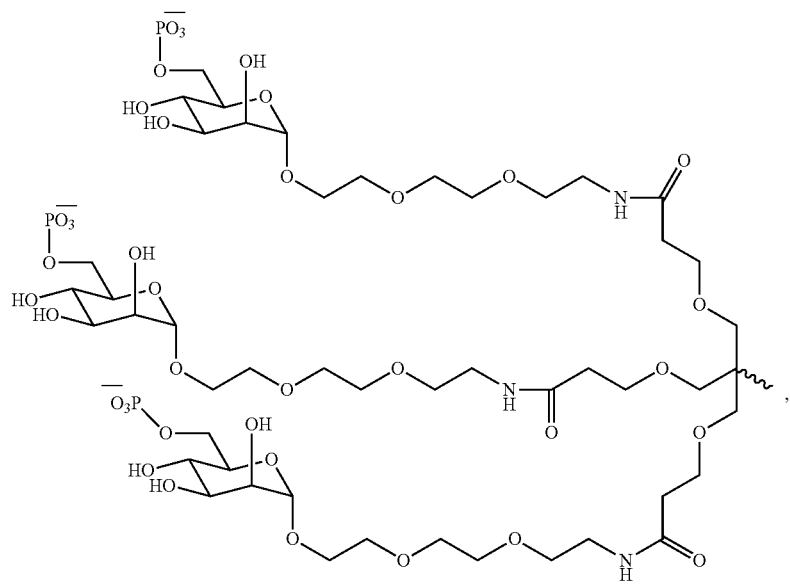
Formula XI

Formula XII
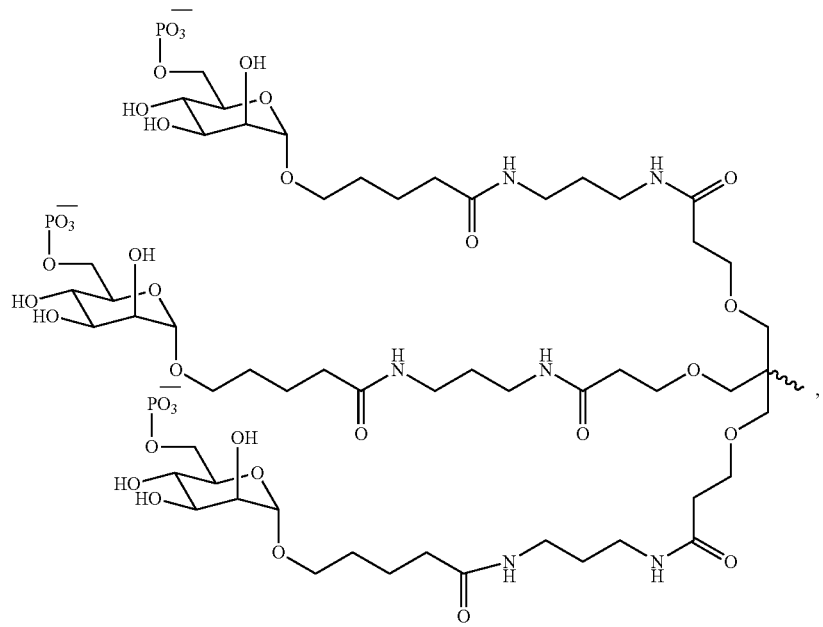
Formula XIII
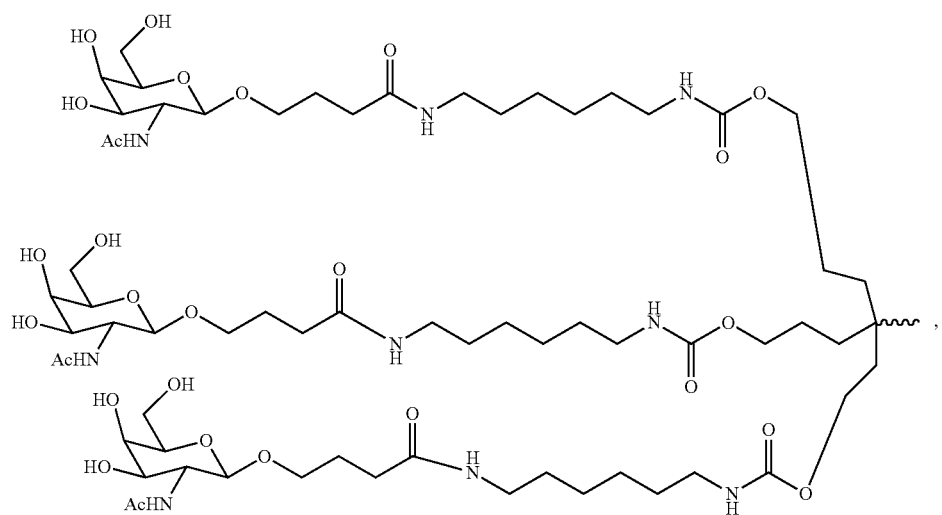
Formula XIV
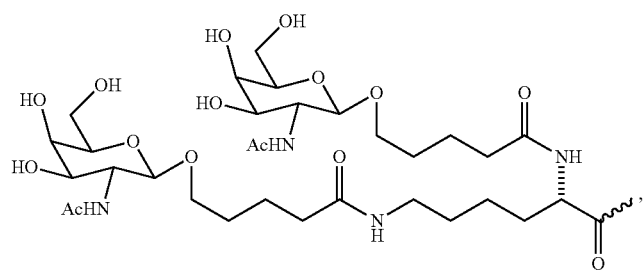

Formula XV
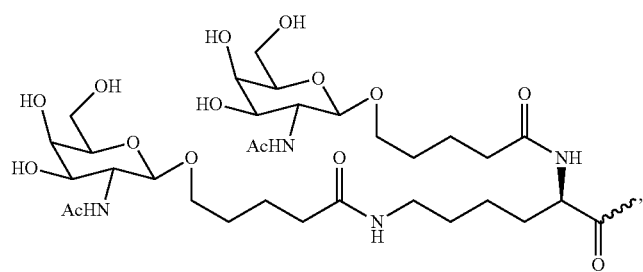
Formula XVI
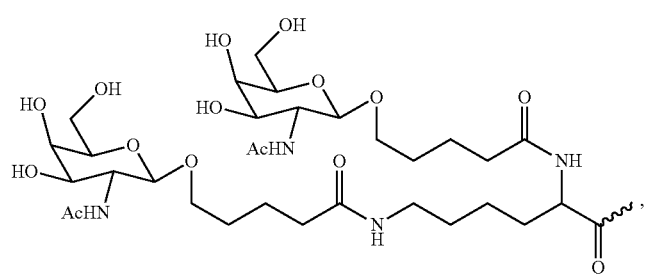
Formula XVII
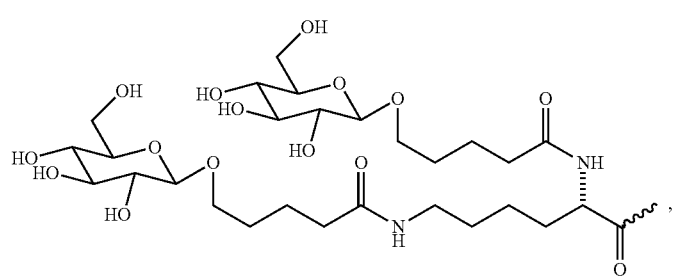
Formula XVIII
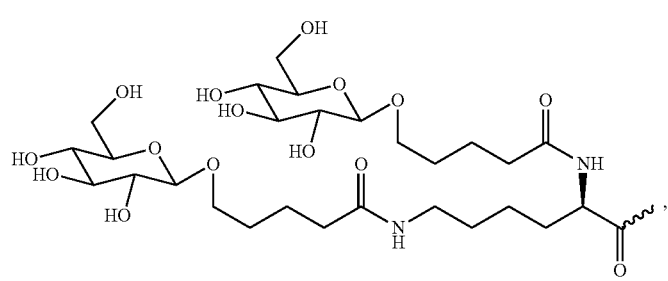
Formula XIX
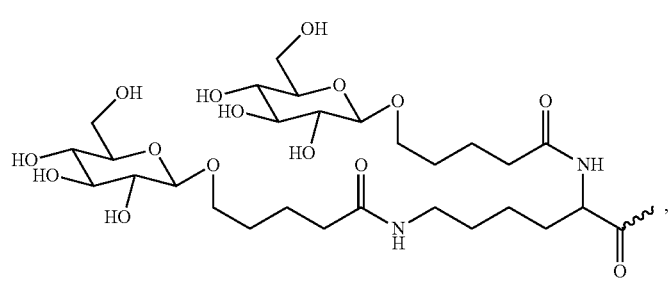

-continued
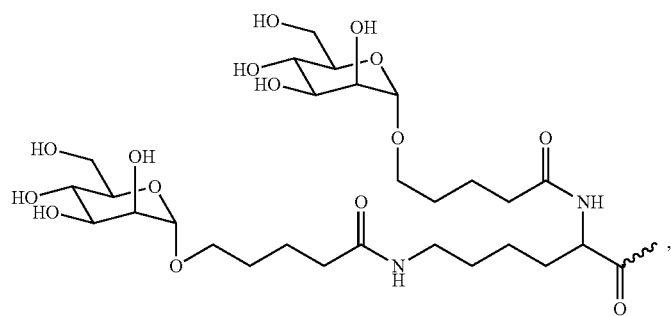
Formula XX
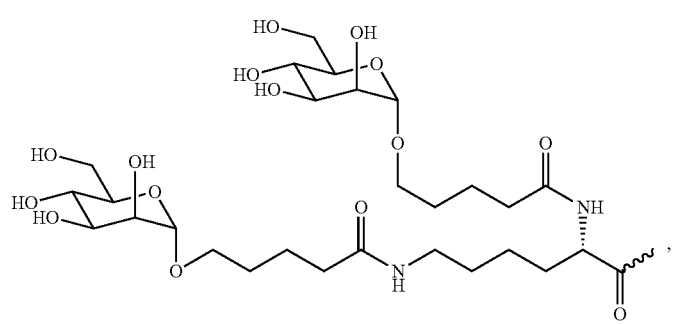
Formula XXI
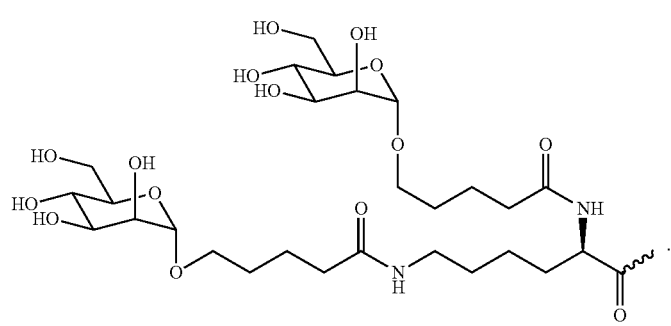
Formula XXII

Another representative carbohydrate conjugate for use in the embodiments described herein includes, but is not limited to,

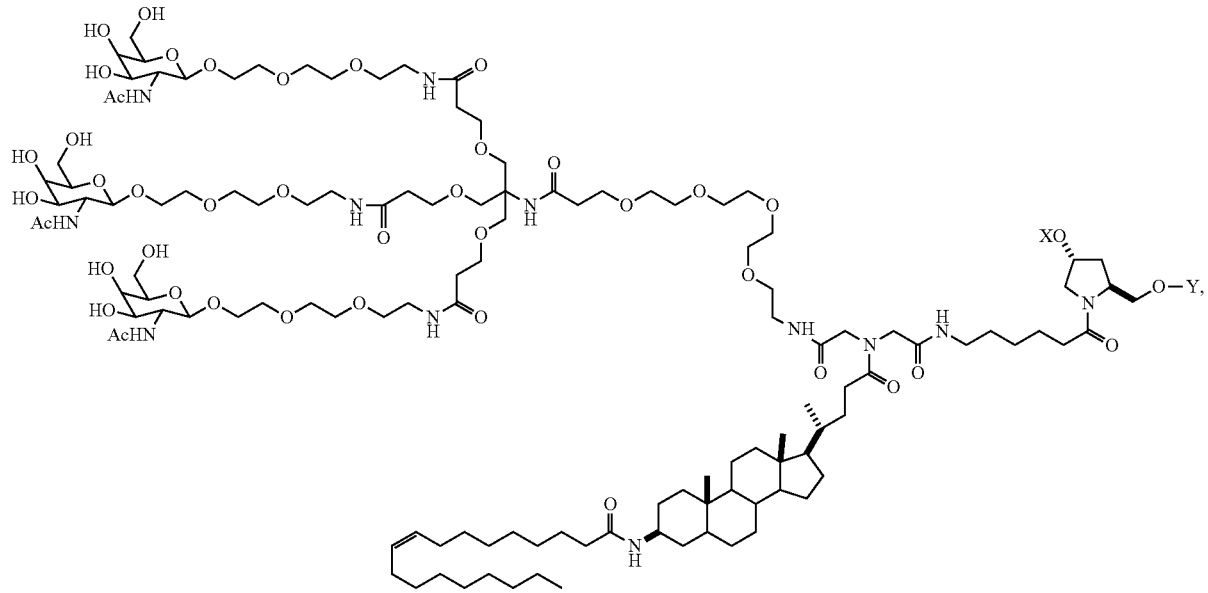

(Formula XXIII)

when one of X or Y is an oligonucleotide, the other is a hydrogen.

In some embodiments, the carbohydrate conjugate further comprises one or more additional ligands as described above, such as, but not limited to, a PK modulator or a cell permeation peptide.

D. Linkers

In some embodiments, the conjugate or ligand described herein can be attached to an antisense polynucleotide agent with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynyl- hereroaryl, which one or more methylenes can be interrupted or terminated by O, S, S(O), SO$_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between 1-24 atoms or any subrange within that range, e.g., 2-24, 3-24, 4-24, 5-24, 6-24, 6-18, 7-18, 8-18, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times, 20, times, 30 times, 40 times, 50 times, 60 times, 70 times, 80 times, 90 times or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate cleavable linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular antisense polynucleotide agent moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most 10% in the blood. In other embodiments, useful candidate compounds are degraded at least 2, 4, 10, 20, 30, 40, 50, 60, 70, 80, 90, or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of 6.5 or lower (e.g., 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an antisense polynucleotide agent of the invention is conjugated to a carbohydrate through a linker. Non-limiting examples of antisense polynucleotide agent carbohydrate conjugates with linkers of the compositions and methods of the invention include, but are not limited to, (Formula XXIV)
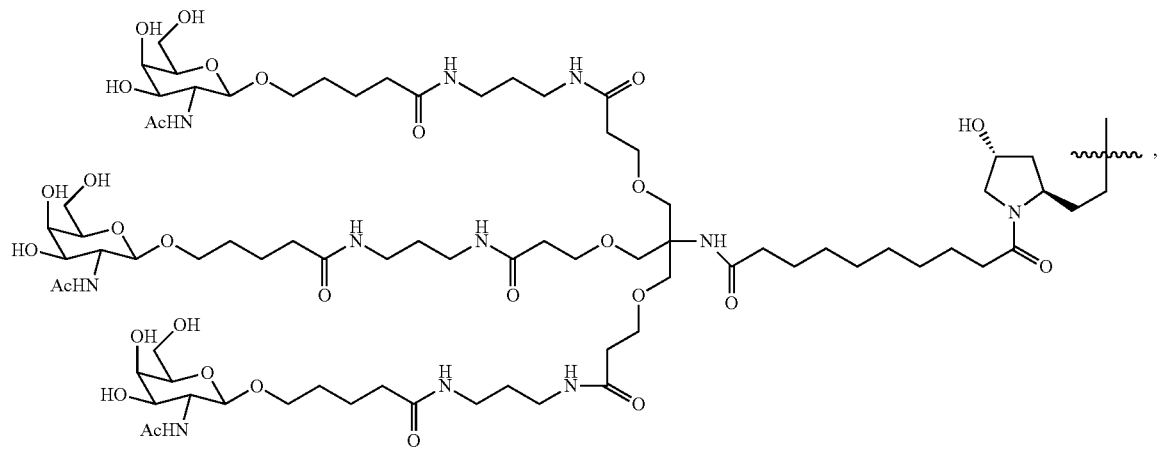
(Formula XXV)
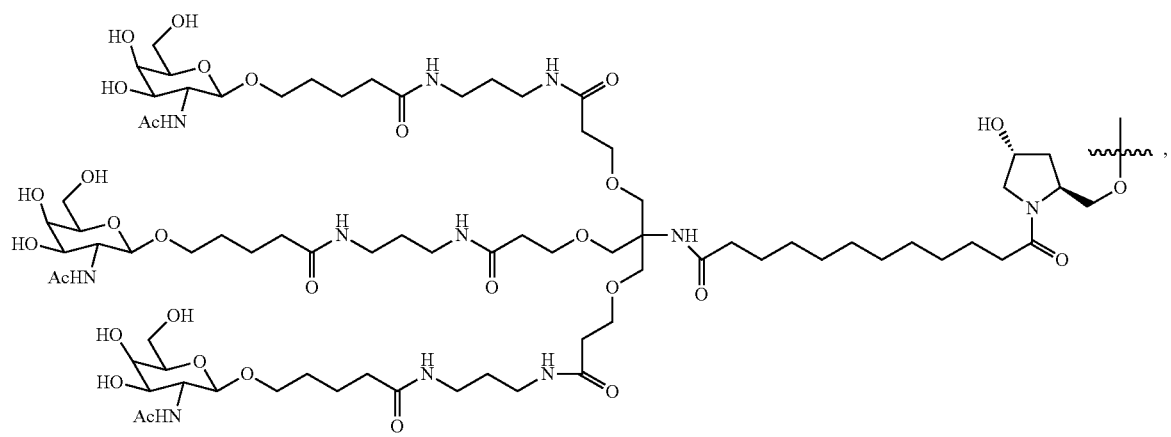
(Formula XXVI)
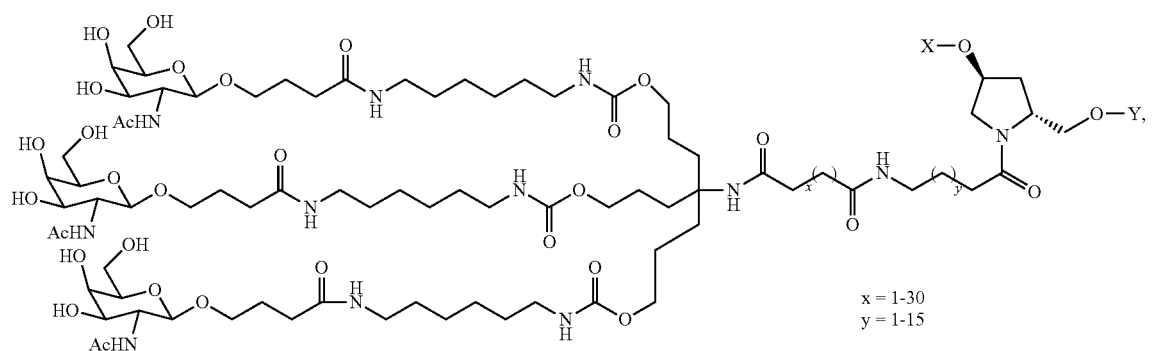
x = 1-30
y = 1-15
(Formula XXVII)
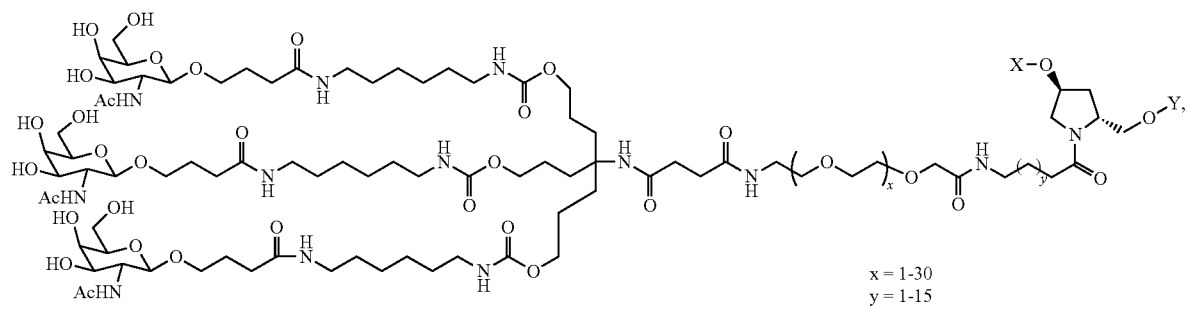
x = 1-30
y = 1-15

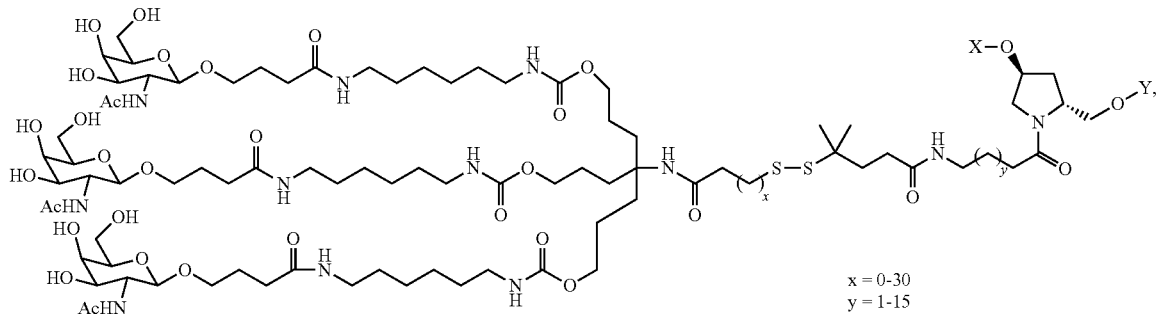
(Formula XXVIII)
x = 0-30
y = 1-15
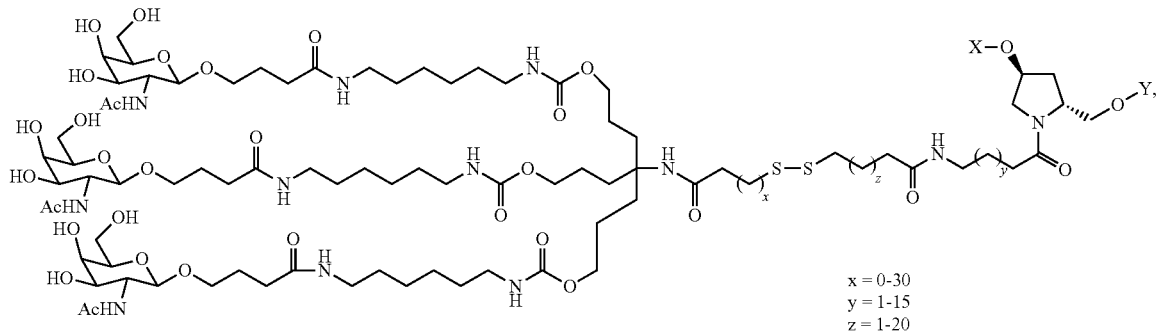
(Formula XXIX)
x = 0-30
y = 1-15
z = 1-20
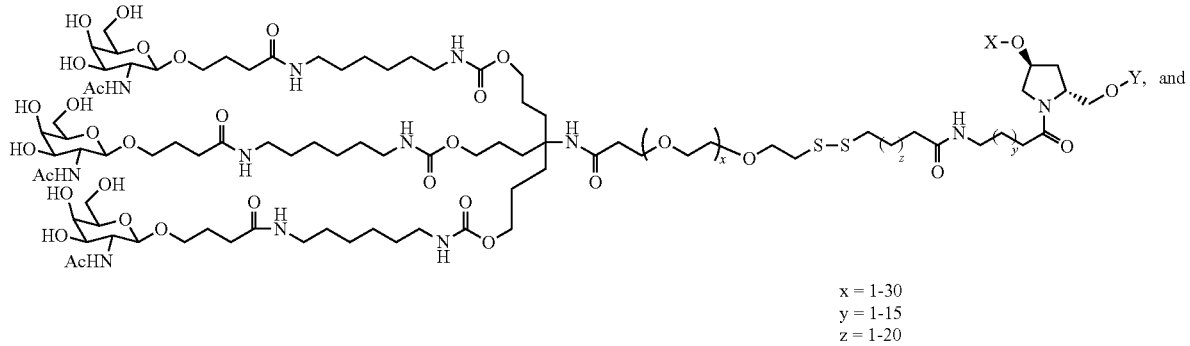
(Formula XXX)
x = 1-30
y = 1-15
z = 1-20
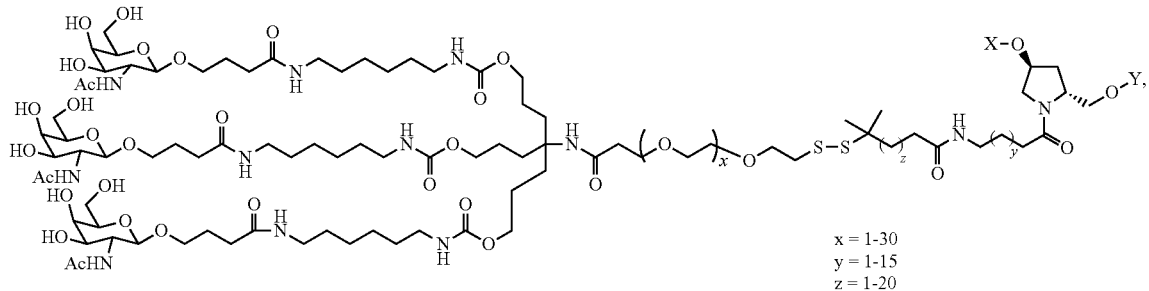
(Formula XXXI)
x = 1-30
y = 1-15
z = 1-20
when one of X or Y is an oligonucleotide, the other is a hydrogen.

In certain embodiments of the compositions and methods of the invention, a ligand is one or more GalNAc (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

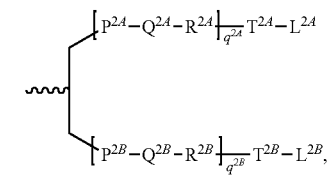

Formula XXXII

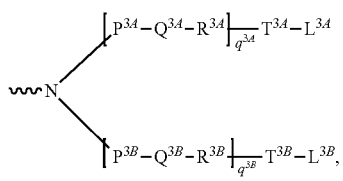

Formula XXXIII

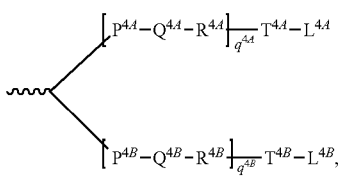

Formula XXXIV

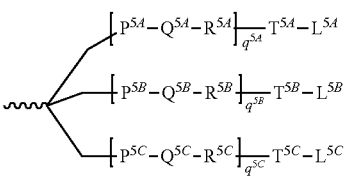

Formula XXXV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherin one or more methylenes can be interrupted or terminated by one or more of O, S, S(O), $SO_2$, $N(R^N)$, C(R')=C(R"), C≡C or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—

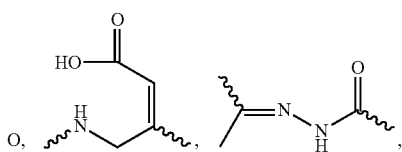

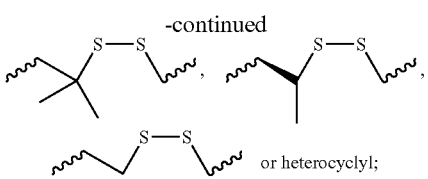
or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXVI):

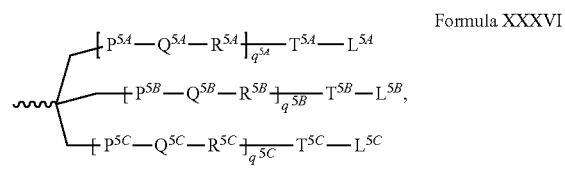

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an antisense polynucleotide agent. The present invention also includes antisense polynucleotide agents that are chimeric compounds.

"Chimeric" antisense polynucleotide agents or "chimeras," in the context of this invention, are antisense polynucleotide agent compounds, which contain two or more chemically distinct regions, each made up of at least one monomer unit, i.e., a nucleotide in the case of an antisense polynucleotide agent. These antisense polynucleotide agents typically contain at least one region wherein the RNA is modified so as to confer upon the antisense polynucleotide agent increased resistance to nuclease degradation, increased cellular uptake, or increased binding affinity for the target nucleic acid. An additional region of the antisense polynucleotide agent can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense polynucleotide agent inhibition of gene expression. Consequently, comparable results can often be obtained with shorter antisense polynucleotide agents when chimeric antisense polynucleotide agents are used, compared to phosphorothioate deoxy antisense polynucleotide agents hybridizing to the same target region. Cleavage of the RNA target can be routinely detected by gel electrophoresis and, if necessary, associated nucleic acid hybridization techniques known in the art.

In certain instances, the nucleotide of an antisense polynucleotide agent can be modified by a non-ligand group. A number of non-ligand molecules have been conjugated to antisense polynucleotide agents in order to enhance the activity, cellular distribution or cellular uptake of the antisense polynucleotide agent, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylaminocarbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an Antisense Polynucleotide Agent of the Invention

The delivery of an antisense polynucleotide agent of the invention to a cell e.g., a cell within a subject, such as a human subject (e.g., a subject in need thereof, such as a subject having a Factor XII-associated disease) can be achieved in a number of different ways. For example, delivery may be performed by contacting a cell with an antisense polynucleotide agent of the invention either in vitro or in vivo. In vivo delivery may also be performed directly by administering a composition comprising an antisense polynucleotide agent to a subject.

In general, any method of delivering a nucleic acid molecule (in vitro or in vivo) can be adapted for use with an antisense polynucleotide agent of the invention (see e.g., Akhtar S. and Julian R L. (1992) *Trends Cell. Biol.* 2(5): 139-144 and WO94/02595, which are incorporated herein by reference in their entireties). For in vivo delivery, factors to consider in order to deliver an antisense polynucleotide agent include, for example, biological stability of the delivered molecule, prevention of non-specific effects, and accumulation of the delivered molecule in the target tissue. The non-specific effects of an antisense polynucleotide agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the antisense polynucleotide agent to be administered.

Several studies have shown successful knockdown of gene products when an antisense polynucleotide agent is administered locally. For example, intraocular delivery of a VEGF antisense polynucleotide agent by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a antisense polynucleotide agent in mice reduces tumor volume (Pille, J., et al (2005) *Mol. Ther.*11: 267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55).

For administering an antisense polynucleotide agent systemically for the treatment of a disease, the agent can be modified or alternatively delivered using a drug delivery system; both methods act to prevent the rapid degradation of the antisense polynucleotide agent by endo- and exo-nucleases in vivo. Modification of the agent or the pharmaceutical carrier can also permit targeting of the antisense polynucleotide agent composition to the target tissue and avoid undesirable off-target effects. Antisense polynucleotide agent can be modified by chemical conjugation to lipophilic groups such as cholesterol to enhance cellular uptake and prevent degradation. In an alternative embodiment, the antisense polynucleotide agent can be delivered using drug delivery systems such as a nanoparticle, a dendrimer, a polymer, liposomes, or a cationic delivery system. Positively charged cationic delivery systems facilitate binding of an antisense polynucleotide agent molecule (negatively charged) and also enhance interactions at the negatively charged cell membrane to permit efficient uptake of an antisense polynucleotide agent by the cell. Cationic lipids, dendrimers, or polymers can either be bound to an antisense polynucleotide agent, or induced to form a vesicle or micelle (see e.g., Kim S H., et al (2008) *Journal of Controlled*

*Release* 129(2):107-116) that encases an antisense polynucleotide agent. The formation of vesicles or micelles further prevents degradation of the antisense polynucleotide agent when administered systemically.

Methods for making and administering cationic-antisense polynucleotide agent complexes are well within the abilities of one skilled in the art (see e.g., Sorensen, D R., et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of antisense polynucleotide agents include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an antisense polynucleotide agent forms a complex with cyclodextrin for systemic administration. Methods for administration and pharmaceutical compositions of antisense polynucleotide agents and cyclodextrins can be found in U.S. Pat. No. 7,427,605, which is herein incorporated by reference in its entirety.

VI. Pharmaceutical Compositions of the Invention

The present invention also includes pharmaceutical compositions and formulations which include the antisense polynucleotide agents of the invention. In one embodiment, provided herein are pharmaceutical compositions containing an antisense polynucleotide agent, as described herein, and a pharmaceutically acceptable carrier.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum components, such as serum albumin, HDL and LDL; and (22) other non-toxic compatible substances employed in pharmaceutical formulations.

The pharmaceutical compositions containing the antisense polynucleotide agents are useful for treating a disease or disorder associated with the expression or activity of a Factor XII gene, e.g. a Factor XII-associated disease. Such pharmaceutical compositions are formulated based on the mode of delivery. One example is compositions that are formulated for systemic administration via parenteral delivery, e.g., by subcutaneous (SC) or intravenous (IV) delivery. The pharmaceutical compositions of the invention may be administered in dosages sufficient to inhibit expression of a Factor XII gene. In general, a suitable dose of an antisense polynucleotide agent of the invention will be in the range of 0.001 to 200.0 milligrams per kilogram body weight of the recipient per day, generally in the range of 1 to 50 mg per kilogram body weight per day. For example, the antisense polynucleotide agent can be administered at 0.01 mg/kg, 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg. Values and ranges intermediate to the recited values are also intended to be part of this invention.

In another embodiment, the antisense polynucleotide agent is administered at a dose of about 0.1 to 50 mg/kg, 0.25 to 50 mg/kg, 0.5 to 50 mg/kg, 0.75 to 50 mg/kg, 1 to 50 mg/mg, 1.5 to 50 mg/kb, 2 to 50 mg/kg, 2.5 to 50 mg/kg, 3 to 50 mg/kg, 3.5 to 50 mg/kg, 4 to 50 mg/kg, 4.5 to 50 mg/kg, 5 to 50 mg/kg, 7.5 to 50 mg/kg, 10 to 50 mg/kg, 15 to 50 mg/kg, 20 to 50 mg/kg, 20 to 50 mg/kg, 25 to 50 mg/kg, 25 to 50 mg/kg, 30 to 50 mg/kg, 35 to 50 mg/kg, 40 to 50 mg/kg, 45 to 50 mg/kg, 0.1 to 45 mg/kg, 0.25 to 45 mg/kg, 0.5 to 45 mg/kg, 0.75 to 45 mg/kg, 1 to 45 mg/mg, 1.5 to 45 mg/kb, 2 to 45 mg/kg, 2.5 to 45 mg/kg, 3 to 45 mg/kg, 3.5 to 45 mg/kg, 4 to 45 mg/kg, 4.5 to 45 mg/kg, 5 to 45 mg/kg, 7.5 to 45 mg/kg, 10 to 45 mg/kg, 15 to 45 mg/kg, 20 to 45 mg/kg, 20 to 45 mg/kg, 25 to 45 mg/kg, 25 to 45 mg/kg, 30 to 45 mg/kg, 35 to 45 mg/kg, 40 to 45 mg/kg, 0.1 to 40 mg/kg, 0.25 to 40 mg/kg, 0.5 to 40 mg/kg, 0.75 to 40 mg/kg, 1 to 40 mg/mg, 1.5 to 40 mg/kb, 2 to 40 mg/kg, 2.5 to 40 mg/kg, 3 to 40 mg/kg, 3.5 to 40 mg/kg, 4 to 40 mg/kg, 4.5 to 40 mg/kg, 5 to 40 mg/kg, 7.5 to 40 mg/kg, 10 to 40 mg/kg, 15 to 40 mg/kg, 20 to 40 mg/kg, 20 to 40 mg/kg, 25 to 40 mg/kg, 25 to 40 mg/kg, 30 to 40 mg/kg, 35 to 40 mg/kg, 0.1 to 30 mg/kg, 0.25 to 30 mg/kg, 0.5 to 30 mg/kg, 0.75 to 30 mg/kg, 1 to 30 mg/mg, 1.5 to 30 mg/kb, 2 to 30 mg/kg, 2.5 to 30 mg/kg, 3 to 30 mg/kg, 3.5 to 30 mg/kg, 4 to 30 mg/kg, 4.5 to 30 mg/kg, 5 to 30 mg/kg, 7.5 to 30 mg/kg, 10 to 30 mg/kg, 15 to 30 mg/kg, 20 to 30 mg/kg, 20 to 30 mg/kg, 25 to 30 mg/kg, 0.1 to 20 mg/kg, 0.25 to 20 mg/kg, 0.5 to 20 mg/kg, 0.75 to 20 mg/kg, 1 to 20 mg/mg, 1.5 to 20 mg/kb, 2 to 20 mg/kg, 2.5 to 20 mg/kg, 3 to 20 mg/kg, 3.5 to 20 mg/kg, 4 to 20 mg/kg, 4.5 to 20 mg/kg, 5 to 20 mg/kg, 7.5 to 20 mg/kg, 10 to 20 mg/kg, or 15 to 20 mg/kg. Values and ranges intermediate to the recited values are also intended to be part of this invention.

For example, the antisense polynucleotide agent may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 2, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg. Values and ranges intermediate to the recited values are also intended to be part of this invention.

In another embodiment, the antisense polynucleotide agent is administered at a dose of about 0.5 to 50 mg/kg, 0.75 to 50 mg/kg, 1 to 50 mg/mg, 1.5 to 50 mg/kgb, 2 to 50 mg/kg, 2.5 to 50 mg/kg, 3 to 50 mg/kg, 3.5 to 50 mg/kg, 4 to 50 mg/kg, 4.5 to 50 mg/kg, 5 to 50 mg/kg, 7.5 to 50 mg/kg, 10 to 50 mg/kg, 15 to 50 mg/kg, 20 to 50 mg/kg, 20 to 50 mg/kg, 25 to 50 mg/kg, 25 to 50 mg/kg, 30 to 50 mg/kg, 35 to 50 mg/kg, 40 to 50 mg/kg, 45 to 50 mg/kg, 0.5 to 45 mg/kg, 0.75 to 45 mg/kg, 1 to 45 mg/mg, 1.5 to 45 mg/kb, 2 to 45 mg/kg, 2.5 to 45 mg/kg, 3 to 45 mg/kg, 3.5 to 45 mg/kg, 4 to 45 mg/kg, 4.5 to 45 mg/kg, 5 to 45 mg/kg, 7.5 to 45 mg/kg, 10 to 45 mg/kg, 15 to 45 mg/kg, 20 to 45 mg/kg, 20 to 45 mg/kg, 25 to 45 mg/kg, 25 to 45 mg/kg, 30 to 45 mg/kg, 35 to 45 mg/kg, 40 to 45 mg/kg, 0.5 to 40 mg/kg, 0.75 to 40 mg/kg, 1 to 40 mg/mg, 1.5 to 40 mg/kb, 2 to 40 mg/kg, 2.5 to 40 mg/kg, 3 to 40 mg/kg, 3.5 to 40 mg/kg, 4 to 40 mg/kg, 4.5 to 40 mg/kg, 5 to 40 mg/kg, 7.5 to 40 mg/kg, 10 to 40 mg/kg, 15 to 40 mg/kg, 20 to 40 mg/kg, 20 to 40 mg/kg, 25 to 40 mg/kg, 25 to 40 mg/kg, 30 to 40 mg/kg, 35 to 40 mg/kg, 0.5 to 30 mg/kg, 0.75 to 30 mg/kg, 1 to 30 mg/mg, 1.5 to 30 mg/kb, 2 to 30 mg/kg, 2.5 to 30 mg/kg, 3 to 30 mg/kg, 3.5 to 30 mg/kg, 4 to 30 mg/kg, 4.5 to 30 mg/kg, 5 to 30 mg/kg, 7.5 to 30 mg/kg, 10 to 30 mg/kg, 15 to 30 mg/kg, 20 to 30 mg/kg, 20 to 30 mg/kg, 25 to 30 mg/kg, 0.5 to 20 mg/kg, 0.75 to 20 mg/kg, 1 to 20 mg/kg, 1.5 to 20 mg/kg, 2 to 20 mg/kg, 2.5 to 20 mg/kg, 3 to 20 mg/kg, 3.5 to 20 mg/kg, 4 to 20 mg/kg, 4.5 to 20 mg/kg, 5 to 20 mg/kg, 7.5 to 20 mg/kg, 10 to 20 mg/kg, or 15 to 20 mg/kg. In one embodiment, the antisense polynucleotide agent is administered at a dose of 10 mg/kg to 30 mg/kg. Values and ranges intermediate to the recited values are also intended to be part of this invention.

For example, subjects can be administered, e.g., subcutaneously or intravenously, a single therapeutic amount of antisense polynucleotide agent, such as about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or 50 mg/kg. Values and ranges intermediate to the recited values are also intended to be part of this invention.

In some embodiments, subjects are administered, e.g., subcutaneously or intravenously, multiple doses of a therapeutic amount of antisense polynucleotide agent, such as a dose about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or 50 mg/kg. A multi-dose regimen may include administration of a therapeutic amount of antisense polynucleotide agent daily, such as for two days, three days, four days, five days, six days, seven days, or longer.

In other embodiments, subjects are administered, e.g., subcutaneously or intravenously, a repeat dose of a therapeutic amount of antisense polynucleotide agent, such as a dose of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or 50 mg/kg. A repeat-dose regimine may include administration of a therapeutic amount of antisense polynucleotide agent on a regular basis, such as every other day, every third day, every fourth day, twice a week, once a week, every other week, or once a month.

The pharmaceutical composition can be administered by intravenous infusion over a period of time, such as over about a 5, 6, 7, 8, 9, 10, 11, 12, 13, 14, 15, 16, 17, 18, 19, 20, and 21, 22, 23, 24, 25, 26, 27, 28, or 29 minute period. In certain embodiments, the infusion is administered over about 0.5, 1, 1.5, 2, 2.5, 3, 3.5, or 4 hours. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered once daily, or the antisense polynucleotide agent can be administered as two, three, or more sub-doses at appropriate intervals throughout the day or even using continuous infusion or delivery through a controlled release formulation. In that case, the antisense polynucleotide agent contained in each sub-dose must be correspondingly smaller in order to achieve the total daily dosage. The dosage unit can also be compounded for delivery over several days, e.g., using a conventional sustained release formulation which provides sustained release of the antisense polynucleotide agent over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments. Estimates of effective dosages and in vivo half-lives for the individual antisense polynucleotide agents encompassed by the invention can be made using conventional methodologies or on the basis of in vivo testing using an appropriate animal model, as described elsewhere herein.

Advances in mouse genetics have generated a number of mouse models for the study of various human diseases, such as a disorder that would benefit from reduction in the expression of Factor XII. Such models can be used for in vivo testing of an antisense polynucleotide agent, as well as for determining a therapeutically effective dose. Suitable mouse models are known in the art and can be selected based on the specific disease or condition to be treated.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The antisense polynucleotide agent can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the antisense polynucleotide agents featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoyl-phosphatidyl glycerol DMPG) and cationic (e.g., dioleoylte-tramethylaminopropyl DOTAP and dioleoylphosphatidyl ethanolamine DOTMA). Antisense polynucleotide agents featured in the invention can be encapsulated within liposomes or can form complexes thereto, in particular to cationic liposomes. Alternatively, antisense polynucleotide agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. Antisense Polynucleotide Agent Formulations Comprising Membranous Molecular Assemblies An antisense polynucleotide agent for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the antisense polynucleotide agent composition. The lipophilic material isolates the aqueous interior from an aqueous exterior, which typically does not include the antisense polynucleotide agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the antisense polynucleotide agent are delivered into the cell where the antisense polynucleotide agent can specifically bind to a target RNA and can mediate antisense inhibition. In some cases the liposomes are also specifically targeted, e.g., to direct the antisense polynucleotide agent to particular cell types.

A liposome containing an antisense polynucleotide agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The antisense polynucleotide agent preparation is then added to the micelles that include the lipid component. The cationic groups on the lipid interact with the antisense polynucleotide agent and condense around the antisense polynucleotide agent to form a liposome. After condensation, the detergent is removed, e.g., by dialysis, to yield a liposomal preparation of antisense polynucleotide agent.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging antisense polynucleotide agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid or phosphatidylcholine or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P.Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver antisense polynucleotide agents to macrophages.

Further advantages of liposomes include: liposomes obtained from natural phospholipids are biocompatible and biodegradable; liposomes can incorporate a wide range of water and lipid soluble drugs; liposomes can protect encapsulated antisense polynucleotide agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of Antisense polynucleotide agent (see, e.g., Feigner, P. L. et al., *Proc. Natl. Acad. Sci., USA* 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration; liposomes present several advantages over other formulations. Such advantages include reduced side effects related to high systemic absorption of the administered drug, increased accumulation of the administered drug at the desired target, and the ability to administer an antisense polynucleotide agent into the skin. In some implementations, liposomes are used for delivering antisense polynucleotide agent to epidermal cells and also to enhance the penetration of antisense polynucleotide agent into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2,405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with antisense polynucleotide agents are useful for treating a dermatological disorder.

Liposomes that include antisense polynucleotide agent can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include antisense polynucleotide agents can be delivered, for example, subcutaneously by infection in order to deliver antisense polynucleotide agents to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in WO2009088892, WO2009086558, WO2009132131, and WO2008042973.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The antisense polynucleotide agent for use in the compositions and methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the antisense polynucleotide agent composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the antisense polynucleotide agent composition and at least the alkali metal alkyl sulphate. The first micellar composition is then mixed with at least three micelle forming compounds to form a mixed micellar composition. In another method, the micellar composition is prepared by mixing the antisense polynucleotide agent composition, the alkali metal alkyl sulphate and at least one of the micelle forming compounds, followed by addition of the remaining micelle forming compounds, with vigorous mixing.

Phenol or m-cresol may be added to the mixed micellar composition to stabilize the formulation and protect against bacterial growth. Alternatively, phenol or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

Antisense polynucleotide agents of in the invention may be fully encapsulated in a lipid formulation, e.g., a LNP, or other nucleic acid-lipid particle.

As used herein, the term "LNP" refers to a stable nucleic acid-lipid particle comprising a lipid layer encapsulating a pharmaceutically active molecule. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of 50 nm to 150 nm, more typically 60 nm to 130 nm, more typically 70 nm to 110 nm, most typically 70 nm to 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; 6,858,225; 8,158,601; and 8,058,069; U.S. Publication No. 2010/0324120 and PCT Publication No. WO 96/40964.

In one embodiment, the lipid to drug ratio (mass/mass ratio) (e.g., lipid to antisense polynucleotide agent ratio) will be in the range of from 1:1 to 50:1, from 1:1 to 25:1, from 3:1 to 15:1, from 4:1 to 10:1, from 5:1 to 9:1, or 6:1 to 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (D-OTAP), N-(1-(2,3-dioleyloxy)propyl)-N,N,N-trimethylammonium chloride (DOTMA), N,N-dimethyl-2,3-dioleyloxy) propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-

Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-D- MAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLin-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from 20 mol % to 50 mol % or 40 mol % of the total lipid present in the particle.

In another embodiment, the compound 2,2-Dilinoleyl-4-dimethylaminoethyl-[1,3]-dioxolane can be used to prepare lipid-santisense polynucleotide agent nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-antisense polynucleotide agent particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 antisense polynucleotide agent/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol(DOPG), dipalmitoylpho sphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from 5 mol % to 90 mol %, 10 mol %, or 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to 20 mol % or 2 mol % of the total lipid present in the particle.

In some embodiments, the nucleic acid-lipid particle further includes cholesterol at, e.g., 10 mol % to 60 mol % or 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-antisense polynucleotide agent nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous antisense polynucleotide agent (e.g., in sodium acetate pH 5) such that the final ethanol concentration is 35-45% and the final sodium acetate concentration is 100-300 mM. Lipid-antisense polynucleotide agent nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at pH 7, e.g., pH 6.9, pH 7.0, pH 7.1, pH 7.2, pH 7.3, or pH 7.4.

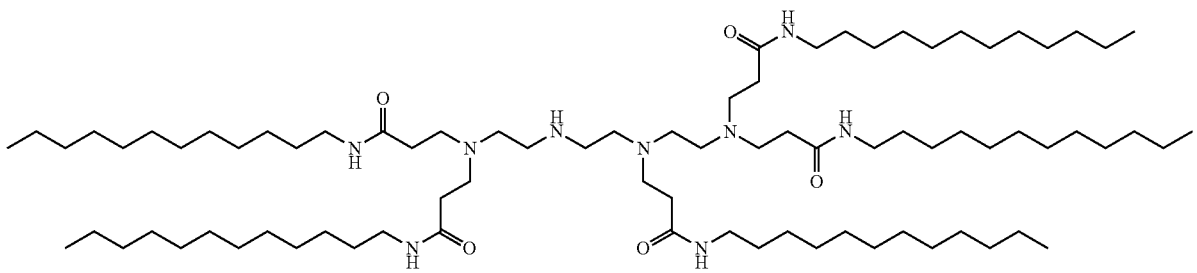

ND98 Isomer I

LNP01 formulations are described, e.g., in International Application Publication No. WO 2008/042973, which is hereby incorporated by reference.

Additional exemplary lipid-antisense polynucleotide agent formulations are described in Table 1.

TABLE 1

| | Ionizable/Cationic Lipid | cationic lipid/non-cationic lipid/cholesterol/PEG-lipid conjugate Lipid:santisense polynucleotide agent ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:santisense polynucleotide agent~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:santisense polynucleotide agent~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:santisense polynucleotide agent~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:santisense polynucleotide agent~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:santisense polynucleotide agent 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:santisense polynucleotide agent 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:santisense polynucleotide agent 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:santisense polynucleotide agent 10:1 |
| LNP13 | XTC | XTC/DSPC/Chol/PEG-DMG 50/10/38.5/1.5 Lipid:santisense polynucleotide agent: 33:1 |
| LNP14 | MC3 | MC3/DSPC/Chol/PEG-DMG 40/15/40/5 Lipid:santisense polynucleotide agent: 11:1 |
| LNP15 | MC3 | MC3/DSPC/Chol/PEG-DSG/GalNAc-PEG-DSG 50/10/35/4.5/0.5 Lipid:santisense polynucleotide agent: 11:1 |
| LNP16 | MC3 | MC3/DSPC/Chol/PEG-DMG 50/10/38.5/1.5 Lipid:santisense polynucleotide agent: 7:1 |
| LNP17 | MC3 | MC3/DSPC/Chol/PEG-DSG 50/10/38.5/1.5 Lipid:santisense polynucleotide agent: 10:1 |
| LNP18 | MC3 | MC3/DSPC/Chol/PEG-DMG 50/10/38.5/1.5 Lipid:santisense polynucleotide agent: 12:1 |

TABLE 1-continued

| | Ionizable/Cationic Lipid | cationic lipid/non-cationic lipid/cholesterol/PEG-lipid conjugate Lipid:santisense polynucleotide agent ratio |
|---|---|---|
| LNP19 | MC3 | MC3/DSPC/Chol/PEG-DMG 50/10/35/5 Lipid:santisense polynucleotide agent: 8:1 |
| LNP20 | MC3 | MC3/DSPC/Chol/PEG-DPG 50/10/38.5/1.5 Lipid:santisense polynucleotide agent: 10:1 |
| LNP21 | C12-200 | C12-200/DSPC/Chol/PEG-DSG 50/10/38.5/1.5 Lipid:santisense polynucleotide agent: 7:1 |
| LNP22 | XTC | XTC/DSPC/Chol/PEG-DSG 50/10/38.5/1.5 Lipid:santisense polynucleotide agent: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. W02009/127060, which is hereby incorporated by reference.
XTC comprising formulations are described in WO2010008537, which is hereby incorporated by reference.
MC3 comprising formulations are described in U.S. Publication No. 2010/0324120, filed Jun. 10, 2010, the entire contents of which are hereby incorporated by reference.
ALNY-100 comprising formulations are described in WO201054406, which is hereby incorporated by reference.
C12-200 comprising formulations are described in WO2010129709, which is hereby incorporated by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which the antisense polynucleotide agents featured in the invention are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. Antisense polynucleotide agents featured in the invention can be delivered orally, in granular form including sprayed dried particles, or complexed to form micro or nanoparticles. Antisense polynucleotide agent complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for antisense polynucleotide agents and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver, e.g., when treating hepatic disorders, e.g., hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of antisense polynucleotide agents are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or antisense polynucleotide agents. Microemulsions have also been effective in the transdermal delivery of active components in both cosmetic and pharmaceutical applications. It is expected that the microemulsion compositions and formulations of the present invention will facilitate the increased systemic absorption of antisense polynucleotide agents from the gastrointestinal tract, as well as improve the local cellular uptake of antisense polynucleotide agents and nucleic acids.

Microemulsions of the present invention can also contain additional components and additives such as sorbitan monostearate (Grill 3), Labrasol, and penetration enhancers to improve the properties of the formulation and to enhance the absorption of the antisense polynucleotide agents of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

iii. Microparticles

An antisense polynucleotide agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly antisense polynucleotide agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p.92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of antisense polynucleotide agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p.92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p.92; Muranishi, Critical Reviews in Therapeutic Drug Carrier Systems, 1990, 7, 1-33; El Hariri et al., *J. Pharm. Pharmacol.*, 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of antisense polynucleotide agents through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of antisense polynucleotide agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of antisense polynucleotide agents at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of antisense polynucleotide agents. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated antisense polynucleotide agent in hepatic tissue can be reduced when it is coadministered with polyinosinic acid, dextran sulfate, polycytidic acid or 4-acetamido-4'isothiocyano-stilbene-2, T-disulfonic acid (Miyao et al., Antisense polynucleotide agent Res. Dev., 1995, 5, 115-121; Takakura et al., Antisense polynucleotide agent & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol or dextran. The suspension can also contain stabilizers.

In some embodiments, pharmaceutical compositions featured in the invention include (a) one or more antisense polynucleotide agents and (b) one or more agents which function by a non-antisense inhibition mechanism and which are useful in treating a hemolytic disorder. Examples of such agents include, but are not limited to an anti-inflammatory agent, anti-steatosis agent, anti-viral, or anti-fibrosis agent. In addition, other substances commonly used to protect the liver, such as silymarin, can also be used in conjunction with the antisense polynucleotide agents described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the $ED_{50}$ with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the antisense polynucleotide agents featured in the invention can be administered in combination with other known agents effective in treatment of pathological processes mediated by Factor XII expression. In any event, the administering physician can adjust the amount and timing of antisense polynucleotide agent administration on the basis of results observed using standard measures of efficacy known in the art or described herein.

VII. Methods For Inhibiting Factor XII Expression

The present invention provides methods of inhibiting expression of Factor XII in a cell. The methods include contacting a cell with an antisense polynucleotide agent of the invention in an amount effective to inhibit expression of the Factor XII in the cell, thereby inhibiting expression of the Factor XII in the cell.

Contacting of a cell with an antisense polynucleotide agent may be done in vitro or in vivo. Contacting a cell in vivo with the antisense polynucleotide agent includes contacting a cell or group of cells within a subject, e.g., a human subject, with the antisense polynucleotide agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the antisense polynucleotide agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a Factor XII" is intended to refer to inhibition of expression of any Factor XII gene (such as, e.g., a mouse Factor XII gene, a rat Factor XII gene, a monkey Factor XII gene, or a human Factor XII gene) as well as variants or mutants of a Factor XII gene. Thus, the Factor XII gene may be a wild-type Factor XII gene, a mutant Factor XII gene, or a transgenic Factor XII gene in the context of a genetically manipulated cell, group of cells, or organism.

"Inhibiting expression of a Factor XII gene" includes any level of inhibition of a Factor XII gene, e.g., at least partial suppression of the expression of a Factor XII gene. The expression of the Factor XII gene may be assessed based on the level, or the change in the level, of any variable associated with Factor XII gene expression, e.g., Factor XII mRNA level, Factor XII protein level, or for example, bradykinin elevation, prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain may also be measured to assess Factor XII expression. This level may be assessed in an individual cell or in a group of cells, including, for example, a sample derived from a subject.

Inhibition may be assessed by a decrease in an absolute or relative level of one or more variables that are associated with Factor XII expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a Factor XII gene is inhibited by at least 20%, 25%, 30%, 35%, 40%, 45%, 50%, 55%, 60%, 65%, at least 70%, 75%, 80%, 85%, 90%, 95%, or to below the level of detection of the assay method; or a similar level of reduction in the difference between a disease level and a normal level in an appropriate control subject. In preferred embodiments, the level of expression is detected using the in vitro method provided in the Examples.

Inhibition of the expression of a Factor XII gene may be manifested by a reduction of the amount of mRNA expressed by a first cell or group of cells (such cells may be present, for example, in a sample derived from a subject) in which a Factor XII gene is transcribed and which has or have been treated (e.g., by contacting the cell or cells with an antisense polynucleotide agent of the invention, or by administering an antisense polynucleotide agent of the invention to a subject in which the cells are or were present) such that the expression of a Factor XII gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a Factor XII gene may be assessed in terms of a reduction of a parameter that is functionally linked to Factor XII gene expression, e.g., Factor XII protein expression, bradykinin level, prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain. Factor XII gene silencing may be determined in any cell expressing Factor XII, either constitutively or by genetic engineering, and by any assay known in the art. The liver is a major site of Factor XII expression.

Inhibition of the expression of a Factor XII protein may be manifested by a reduction in the level of the Factor XII protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a Factor XII gene includes a cell or group of cells that has not yet been contacted with an antisense polynucleotide agent of the invention. For example, the control cell or group of cells may be derived from an individual subject (e.g., a human or animal subject) prior to treatment of the subject with an antisense polynucleotide agent.

The level of Factor XII mRNA that is expressed by a cell or group of cells may be determined using any method known in the art for assessing mRNA expression. In one embodiment, the level of expression of Factor XII in a sample is determined by detecting a transcribed polynucleotide, or portion thereof, e.g., mRNA of the Factor XII gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (Pre-Analytix, Switzerland). Typical assay formats utilizing ribo-nucleic acid hybridization include nuclear run-on assays, RT-PCR, RNase protection assays (Melton et al., *Nuc. Acids Res.* 12:7035), northern blotting, in situ hybridization, and microarray analysis.

In one embodiment, the level of expression of Factor XII is determined using a nucleic acid probe. The term "probe", as used herein, refers to any molecule that is capable of selectively binding to a specific Factor XII. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to Factor XII mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of Factor XII mRNA.

An alternative method for determining the level of expression of Factor XII in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of Factor XII is determined by quantitative fluorogenic RT-PCR (i.e., the TaqMan™ System).

The expression levels of Factor XII mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of Factor XII expression level may also comprise using nucleic acid probes in solution.

In preferred embodiments, the level of mRNA expression is assessed using branched DNA (bDNA) assays or real time PCR (qPCR). The use of a qPCR methods is described and exemplified in the Examples presented herein.

The level of Factor XII protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the antisense polynucleotide agent is administered to a subject such that the antisense polynucleotide agent is delivered to a specific site within the subject. The inhibition of expression of Factor XII may be assessed using measurements of the level or change in the level of Factor XII mRNA or Factor XII protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

The phrase "contacting a cell with an antisense polynucleotide agent," as used herein, includes contacting a cell by any possible means. Contacting a cell with an antisense polynucleotide agent includes contacting a cell in vitro with the antisense polynucleotide agent or contacting a cell in vivo with the antisense polynucleotide agent. The contacting may be done directly or indirectly. Thus, for example, the antisense polynucleotide agent may be put into physical contact with the cell by the individual performing the method, or alternatively, the antisense polynucleotide agent may be put into a situation that will permit or cause it to subsequently come into contact with the cell.

Contacting a cell in vitro may be done, for example, by incubating the cell with the antisense polynucleotide agent. Contacting a cell in vivo may be done, for example, by injecting the antisense polynucleotide agent into or near the tissue where the cell is located, or by injecting the antisense polynucleotide agent into another area, e.g., the bloodstream or the subcutaneous space, such that the agent will subsequently reach the tissue where the cell to be contacted is located. For example, the antisense polynucleotide agent may contain or be coupled to a ligand, e.g., GalNAc3, that directs the antisense polynucleotide agent to a site of interest, e.g., the liver. Combinations of in vitro and in vivo methods of contacting are also possible. For example, a cell may also be contacted in vitro with an antisense polynucleotide agent and subsequently transplanted into a subject.

In one embodiment, contacting a cell with an antisense polynucleotide agent includes "introducing" or "delivering the antisense polynucleotide agent into the cell" by facilitating or effecting uptake or absorption into the cell. Absorption or uptake of an antisense polynucleotide agent can occur through unaided diffusive or active cellular processes, or by auxiliary agents or devices. Introducing an antisense polynucleotide agent into a cell may be in vitro or in vivo. For example, for in vivo introduction, antisense polynucleotide agent can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below or are known in the art.

VIII. Methods for Treating a Factor XII-Associated Disorder

The present invention also provides therapeutic and prophylactic methods which include administering to a subject having a Factor XII-associated disease, e.g., heredity angioedema (HAE), prekallikrein deficiency, malignant essential hypertension, hypertension, end stage renal disease, or Fletcher Factor Deficiency, an antisense polynucleotide agent or pharmaceutical compositions comprising an antisense polynucleotide agent of the invention.

In one aspect, the present invention provides methods of treating a subject having a disorder that would benefit from reduction in Factor XII expression, e.g., a Factor XII-associated disease, e.g., heredity angioedema (HAE), prekallikrein deficiency, malignant essential hypertension, hypertension, end stage renal disease, or Fletcher Factor Deficiency. The treatment methods (and uses) of the invention include administering to the subject, e.g., a human, a therapeutically effective amount of an antisense polynucleotide agent targeting a Factor XII gene or a pharmaceutical composition comprising an antisense polynucleotide agent targeting a Factor XII gene, thereby treating the subject having a disorder that would benefit from reduction in Factor XII expression.

In another aspect, the present invention provides methods of treating a subject having a disorder that would benefit from reduction in Factor XII expression, e.g., a Factor XII-associated disease, e.g., heredity angioedema (HAE), prekallikrein deficiency, malignant essential hypertension, hypertension, end stage renal disease, or Fletcher Factor Deficiency, which include administering to the subject, e.g., a human, a therapeutically effective amount of an antisense polynucleotide agent targeting a Factor XII gene or a pharmaceutical composition comprising an antisense polynucleotide agent targeting a Factor XII gene, and an additional therapeutic agent, such as an androgen, such as danazol or oxandrolone, Berinert®, Cinryze™, Rhuconest®, Ecallantide, Firazyr®, Kalbitor®, and a combination of any of the foregoing, thereby treating the subject having a disorder that would benefit from reduction in Factor XII expression.

"Therapeutically effective amount," as used herein, is intended to include the amount of an antisense polynucleotide agent, that, when administered to a subject having a Factor XII-associated disease, is sufficient to effect treatment of the disease (e.g., by diminishing, ameliorating or maintaining the existing disease or one or more symptoms of disease). The "therapeutically effective amount" may vary depending on the antisense polynucleotide agent, how the agent is administered, the disease and its severity and the history, age, weight, family history, genetic makeup, the types of preceding or concomitant treatments, if any, and other individual characteristics of the subject to be treated.

A "therapeutically effective amount" also includes an amount of an antisense polynucleotide agent that produces some desired local or systemic effect at a reasonable benefit/risk ratio applicable to any treatment. Antisense polynucleotide agents employed in the methods of the present invention may be administered in a sufficient amount to produce a reasonable benefit/risk ratio applicable to such treatment.

In another aspect, the present invention provides uses of a therapeutically effective amount of an antisense polynucleotide agent of the invention for treating a subject, e.g., a subject that would benefit from a reduction or inhibition of Factor XII expression.

In another aspect, the present invention provides uses of a therapeutically effective amount of an antisense polynucleotide agent of the invention and an additional therapeutic agent, such as an androgen, such as danazol or oxandrolone, Berinert®, Cinryze™, Rhuconest®, Ecallantide, Firazyr®, Kalbitor®, and a combination of any of the foregoing, for treating a subject, e.g., a subject that would benefit from a reduction or inhibition of Factor XII expression.

In yet another aspect, the present invention provides use of an antisense polynucleotide agent of the invention targeting a Factor XII gene or a pharmaceutical composition comprising an antisense polynucleotide agent targeting a Factor XII gene in the manufacture of a medicament for treating a subject, e.g., a subject that would benefit from a reduction or inhibition of Factor XII expression, such as a subject having a disorder that would benefit from reduction in Factor XII expression, e.g., a Factor XII-associated disease, e.g., heredity angioedema (HAE), prekallikrein deficiency, malignant essential hypertension, hypertension, end stage renal disease, or Fletcher Factor Deficiency.

In another aspect, the present invention provides uses of an antisense polynucleotide agent of the invention targeting a Factor XII gene or a pharmaceutical composition comprising an antisense polynucleotide agent targeting a Factor XII gene in the manufacture of a medicament for use in combination with an additional therapeutic agent, such as an androgen, such as danazol or oxandrolone, Berinert®, Cinryze™, Rhuconest®, Ecallantide, Firazyr®, Kalbitor®, and a combination of any of the foregoing, for treating a subject, e.g., a subject that would benefit from a reduction or inhibition of Factor XII expression, e.g., a Factor XII-associated disease, e.g., heredity angioedema (HAE), prekallikrein deficiency, malignant essential hypertension, hypertension, end stage renal disease, or Fletcher Factor Deficiency.

In yet another aspect, the invention provides uses of an antisense polynucleotide agent of the invention, and an additional therapeutic agent, such as an androgen, such as danazol or oxandrolone, Berinert®, Cinryze™, Rhuconest®, Ecallantide, Firazyr®, Kalbitor®, and a combination of any of the foregoing, for preventing at least one symptom in a subject suffering from a disorder that would benefit from a reduction or inhibition of Factor XII expression, such as a Factor XII-associated disease, e.g., heredity angioedema (HAE), prekallikrein deficiency, malignant essential hypertension, hypertension, end stage renal disease, or Fletcher Factor Deficiency.

In a further aspect, the present invention provides uses of an antisense polynucleotide agent of the invention in the manufacture of a medicament for preventing at least one symptom in a subject suffering from a disorder that would benefit from a reduction or inhibition of Factor XII expression, such as a a Factor XII-associated disease, e.g., heredity angioedema (HAE) (such as hereditary angioedema type I; hereditary angioedema type II; hereditary angioedema type III; or any other hereditary angioedema caused by elevated levels of bradykinin), prekallikrein deficiency, malignant essential hypertension, hypertension, end stage renal disease, Fletcher Factor Deficiency, edema swelling of the extremities, face, larynx, upper respiratory tract, abdomen, trunk, and genitals, prodrome; laryngeal swelling; nonpruritic rash; nausea; vomiting; abdominal pain.

In one embodiment, an antisense polynucleotide agent targeting Factor XII is administered to a subject having a Factor XII-associated disease such that Factor XII levels, e.g., in a cell, tissue, blood, urine or other tissue or fluid of the subject are reduced as compared to an appropriate control by at least 20%, 25%, 30%, 35%, 40%, 45%, 50%, 55%, 60%, 65%, 70%, 75%, 80%, 85%, 90%, 95%, or to a level below the level of detection of the assay method as compared to an appropriate control. In certain embodiments, the Factor XII level a similar level of reduction in the difference between a disease level and a normal level in an appropriate control subject.

The additional therapeutic may be an androgen, such as danazol or oxandrolone, Berinert®, Cinryze™, Rhuconest®, Ecallantide, Firazyr®, Kalbitor®, and a combination of any of the foregoing.

The additional therapeutic, e.g., an androgen, such as danazol or oxandrolone, Berinert®, Cinryze™, Rhuconest®, Ecallantide, Firazyr®, Kalbitor®, and a combination of any of the foregoing, may be administered to the subject at the same time as the antisense polynucleotide agent targeting Factor XII or at a different time.

Moreover, the additional therapeutic, e.g., an androgen, such as danazol or oxandrolone, Berinert®, Cinryze™, Rhuconest®, Ecallantide, Firazyr®, Kalbitor®, and a combination of any of the foregoing, may be administered to the subject in the same formulation as the antisense polynucleotide agent targeting Factor XII or in a different formulation as the antisense polynucleotide agent targeting Factor XII.

The methods and uses of the invention include administering a composition described herein such that expression of the target Factor XII gene is decreased, such as for at least about 1, 2, 3, 4, 5, 6, 7, 8, 12, 16, 18, 24, 28, 32, 36, 40, 44, 48, 52, 56, 60, 64, 68, 72, 76, or 80 hours. In one embodiment, expression of the target Factor XII gene is decreased for an extended duration, e.g., at least two, three, four, five, six, seven days or more, e.g., one week, two weeks, three weeks, or four weeks, or longer.

Administration of the antisense polynucleotide agent according to the methods and uses of the invention may result in a reduction of the severity, signs, symptoms, or markers of such diseases or disorders in a patient with a Factor XII-associated disease. By "reduction" in this context is meant a statistically significant decrease in such level as compared to an appropriate control. The reduction can be, for example, at least 30%, 35%, 40%, 45%, 50%, 55%, 60%, 65%, 70%, 75%, 80%, 85%, 90%, 95%, or to below the level of detection of the assay used for detection; or a similar level of reduction in the difference between a disease level and a normal level in an appropriate control subject. In certain embodiments, the reduction is the normalization of the level of a sign or symptom of a disease, a reduction in the difference between the subject level of a sign of the disease and the normal level of the sign for the disease (e.g., upper level of normal, lower level of normal, average of upper and lower level of normal). For example, reduction can be understood as normalization of blood pressure, decreasing an elevated blood pressure or increasing a low blood pressure to reduce the difference from a normal reading.

Efficacy of treatment or prevention of disease can be assessed, for example by measuring disease progression, disease remission, reduction in symptom severity, e.g., severity of edema and swelling, nonpruritic rash, nausea, and vomiting; reduction in pain e.g., abdominal pain, and the dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of HAE can be determined by assessing severe swelling of the arms, legs, hands, feet, face, tongue and larynx, abdomen, nausea, vomiting, and nonpriuric rash. Elevated levels of bradykinin peptide are observed during HAE attacks or episdes. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an antisense polynucleotide agent targeting Factor XII or pharmaceutical composition thereof, "effective against" a Factor XII-associated disease indicates that administration in a clinically appropriate manner results in a beneficial effect for at least a statistically significant fraction of patients, such as improvement of symptoms, a cure, a reduction in disease, extension of life, or other effect generally recognized as positive by medical doctors familiar with treating a Factor XII-associated disease and the related causes.

A treatment effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given antisense polynucleotide agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted criteria based on the disease state. Any positive change resulting in e.g., lessening of severity of disease measured using the appropriate scale, represents adequate treatment using an antisense polynucleotide agent or antisense polynucleotide agent formulation as described herein.

Subjects can be administered a therapeutic amount of antisense polynucleotide agent, such as about 0.01 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 9.0 mg/kg, 10 mg/kg, 15 mg/kg, 20 mg/kg, 25 mg/kg, 30 mg/kg, 35 mg/kg, 40 mg/kg, 45 mg/kg, or 50 mg/kg. Values and ranges intermediate to the recited values are also intended to be part of this invention.

In certain embodiments, for example, when a composition of the invention comprises a antisense polynucleotide agent as described herein and a lipid, subjects can be administered a therapeutic amount of antisense polynucleotide agent, such as about 0.01 mg/kg to 5 mg/kg, 0.01 mg/kg to 10 mg/kg, 0.05 mg/kg to 5 mg/kg, 0.05 mg/kg to 10 mg/kg, 0.1 mg/kg to 5 mg/kg, 0.1 mg/kg to 10 mg/kg, 0.2 mg/kg to 5 mg/kg, 0.2 mg/kg to 10 mg/kg, 0.3 mg/kg to 5 mg/kg, 0.3 mg/kg to 10 mg/kg, 0.4 mg/kg to 5 mg/kg, 0.4 mg/kg to 10 mg/kg, 0.5 mg/kg to 5 mg/kg, 0.5 mg/kg to 10 mg/kg, 1 mg/kg to 5 mg/kg, 1 mg/kg to 10 mg/kg, 1.5 mg/kg to 5 mg/kg, 1.5 mg/kg to 10 mg/kg, 2 mg/kg to 2.5 mg/kg, 2 mg/kg to 10 mg/kg, 3 mg/kg to 5 mg/kg, 3 mg/kg to 10 mg/kg, 3.5 mg/kg to 5 mg/kg, 4 mg/kg to 5 mg/kg, 4.5 mg/kg to 5 mg/kg, 4 mg/kg to 10 mg/kg, 4.5 mg/kg to 10 mg/kg, 5 mg/kg to 10 mg/kg, 5.5 mg/kg to 10 mg/kg, 6 mg/kg to 10 mg/kg, 6.5 mg/kg to 10 mg/kg, 7 mg/kg to 10 mg/kg, 7.5 mg/kg to 10 mg/kg, 8 mg/kg to 10 mg/kg, 8.5 mg/kg to 10 mg/kg, 9 mg/kg to 10 mg/kg, or 9.5 mg/kg to 10 mg/kg. Values and ranges intermediate to the recited values are also intended to be part of this invention.

For example, the antisense polynucleotide agent may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a antisense polynucleotide agent as described herein and an N-acetylgalactosamine, subjects can be administered a therapeutic amount of antisense polynucleotide agent, such as a dose of about 0.1 to 50 mg/kg, 0.25 to 50 mg/kg, 0.5 to 50 mg/kg, 0.75 to 50 mg/kg, 1 to 50 mg/mg, 1.5 to 50 mg/kb, 2 to 50 mg/kg, 2.5 to 50 mg/kg, 3 to 50 mg/kg, 3.5 to 50 mg/kg, 4 to 50 mg/kg, 4.5 to 50 mg/kg, 5 to 50 mg/kg, 7.5 to 50 mg/kg, 10 to 50 mg/kg, 15 to 50 mg/kg, 20 to 50 mg/kg, 20 to 50 mg/kg, 25 to 50 mg/kg, 25 to 50 mg/kg, 30 to 50 mg/kg, 35 to 50 mg/kg, 40 to 50 mg/kg, 45 to 50 mg/kg, 0.1 to 45 mg/kg, 0.25 to 45 mg/kg, 0.5 to 45 mg/kg, 0.75 to 45 mg/kg, 1 to 45 mg/mg, 1.5 to 45 mg/kb, 2 to 45 mg/kg, 2.5 to 45 mg/kg, 3 to 45 mg/kg, 3.5 to 45 mg/kg, 4 to 45 mg/kg, 4.5 to 45 mg/kg, 5 to 45 mg/kg, 7.5 to 45 mg/kg, 10 to 45 mg/kg, 15 to 45 mg/kg, 20 to 45 mg/kg, 20 to 45 mg/kg, 25 to 45 mg/kg, 25 to 45 mg/kg, 30 to 45 mg/kg, 35 to 45 mg/kg, 40 to 45 mg/kg, 0.1 to 40 mg/kg, 0.25 to 40 mg/kg, 0.5 to 40 mg/kg, 0.75 to 40 mg/kg, 1 to 40 mg/mg, 1.5 to 40 mg/kb, 2 to 40 mg/kg, 2.5 to 40 mg/kg, 3 to 40 mg/kg, 3.5 to 40 mg/kg, 4 to 40 mg/kg, 4.5 to 40 mg/kg, 5 to 40 mg/kg, 7.5 to 40 mg/kg, 10 to 40 mg/kg, 15 to 40 mg/kg, 20 to 40 mg/kg, 20 to 40 mg/kg, 25 to 40 mg/kg, 25 to 40 mg/kg, 30 to 40 mg/kg, 35 to 40 mg/kg, 0.1 to 30 mg/kg, 0.25 to 30 mg/kg, 0.5 to 30 mg/kg, 0.75 to 30 mg/kg, 1 to 30 mg/mg, 1.5 to 30 mg/kb, 2 to 30 mg/kg, 2.5 to 30 mg/kg, 3 to 30 mg/kg, 3.5 to 30 mg/kg, 4 to 30 mg/kg, 4.5 to 30 mg/kg, 5 to 30 mg/kg, 7.5 to 30 mg/kg, 10 to 30 mg/kg, 15 to 30 mg/kg, 20 to 30 mg/kg, 20 to 30 mg/kg, 25 to 30 mg/kg, 0.1 to 20 mg/kg, 0.25 to 20 mg/kg, 0.5 to 20 mg/kg, 0.75 to 20 mg/kg, 1 to 20 mg/mg, 1.5 to 20 mg/kb, 2 to 20 mg/kg, 2.5 to 20 mg/kg, 3 to 20 mg/kg, 3.5 to 20 mg/kg, 4 to 20 mg/kg, 4.5 to 20 mg/kg, 5 to 20 mg/kg, 7.5 to 20 mg/kg, 10 to 20 mg/kg, or 15 to 20 mg/kg. In one embodiment, when a composition of the invention comprises a antisense polynucleotide agent as described herein and an N-acetylgalactosamine, subjects can be administered a therapeutic amount of 10 to 30 mg/kg of antisense polynucleotide agent. Values and ranges intermediate to the recited values are also intended to be part of this invention.

For example, subjects can be administered a therapeutic amount of antisense polynucleotide agent, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or 50 mg/kg. Values and ranges intermediate to the recited values are also intended to be part of this invention.

The antisense polynucleotide agent can be administered by intravenous infusion over a period of time, such as over a 5, 6, 7, 8, 9, 10, 11, 12, 13, 14, 15, 16, 17, 18, 19, 20, 21, 22, 23, 24, or a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the antisense polynucleotide agent can reduce Factor XII levels, e.g., in a cell, tissue, blood, urine or other compartment of the patient by at least 20%, 25%, 30%, 35%, 40%, 45%, 50%, 55%, 60%, 65%, 70%, 75%, 80%, 85%, 90%, 95%, or to below the level of detection of the assay method used; or a similar level of reduction in the difference between a disease level and a normal level in an appropriate control subject.

Before administration of a full dose of the antisense polynucleotide agent, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on Factor XII expression, a composition according to the invention or a pharmaceutical composition prepared therefrom can enhance the quality of life.

An antisense polynucleotide agent of the invention may be administered in "naked" form, or as a "free antisense polynucleotide agent." A naked antisense polynucleotide agent is administered in the absence of a pharmaceutical composition. The naked antisense polynucleotide agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the antisense polynucleotide agent can be adjusted such that it is suitable for administering to a subject.

Alternatively, an antisense polynucleotide agent of the invention may be administered as a pharmaceutical composition, such as an antisense polynucleotide agent liposomal formulation.

Subjects that would benefit from a reduction or inhibition of Factor XII gene expression are those having a Factor XII-associated disease or disorder as described herein. In one embodiment, a subject having a Factor XII-associated disease has heredity angioedema (HAE). In another embodiment, a subject having a Factor XII-associated disease has prekallikrein deficiency. In another embodiment, a subject having a Factor XII-associated disease has hypertension, e.g., malignant essential hypertension. In yet another embodiment, a subject having a Factor XII-associated disease has end stage renal disease. In one embodiment, a subject having a Factor XII-associated disease has Fletcher Factor Deficiency.

The invention further provides methods and uses of an antisense polynucleotide agent or a pharmaceutical composition thereof (including methods and uses of an antisense polynucleotide agent or a pharmaceutical composition comprising an antisense polynucleotide agent and an androgen, such as danazol or oxandrolone, Berinert®, Cinryze™, Rhuconest®, Ecallantide, Firazyr®, Kalbitor®, and a combination of any of the foregoing for treating a subject that would benefit from reduction or inhibition of Factor XII expression, e.g., a subject having a Factor XII-associated disease, in combination with other pharmaceuticals or other therapeutic methods, e.g., with known pharmaceuticals or known therapeutic methods, such as, for example, those which are currently employed for treating these disorders. For example, in certain embodiments, an antisense polynucleotide agent targeting Factor XII is administered in combination with, e.g., an agent useful in treating a Factor XII-associated disease as described elsewhere herein.

The antisense polynucleotide agent and an additional therapeutic agent or treatment may be administered at the same time or in the same combination, e.g., parenterally, or the additional therapeutic agent can be administered as part of a separate composition or at separate times or by another method known in the art or described herein.

The present invention also provides methods of using an antisense polynucleotide agent of the invention or a composition containing an antisense polynucleotide agent of the invention to reduce or inhibit Factor XII expression in a cell. In other aspects, the present invention provides an antisense polynucleotide agent of the invention or a composition comprising an antisense polynucleotide agent of the invention for use in reducing or inhibiting Factor XII expression in a cell. In yet other aspects, use of an antisense polynucleotide agent of the invention or a composition comprising an antisense polynucleotide agent of the invention for the manufactuire of a medicament for reducing or inhibiting Factor XII expression in a cell are provided.

The methods and uses include contacting the cell with an antisense polynucleotide agent, e.g., a antisense polynucleotide agent, of the invention and maintaining the cell for a time sufficient to obtain antisense inhibition of a Factor XII gene, thereby inhibiting expression of the Factor XII gene in the cell.

Reduction in gene expression can be assessed by any methods known in the art and as provided herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the antisense polynucleotide agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Antisense Polynucleotide Synthesis

A set of antisense polynucleotide agents targeting the human F12 gene (coagulation factor XII) (human NCBI refseqID: NM_000505; NCBI GeneID: 2161) were designed using custom R and Python scripts. The rationale and method for the set of designs is as follows: the predicted efficacy for every potential 19mer from position 1 through the end of the mRNA was determined with a linear model derived the direct measure of mRNA knockdown from more than 20,000 distinct ASO designs targeting a large number of vertebrate genes. Starting from position 1 a set of s was created by systematically picking a design whose 5' base began every 11 bases along the entire length of the mRNA. Predicted efficacy was used to allow for the substitution of a neighboring, predicted-to-be-more-potent design where the neighboring was 1 base either toward the 5' or 3' end of the mRNA. Low complexity designs were removed by filtering with a Shannon entropy index greater than 1.35.

The antisense polynucleotides targeting Factor XII were synthesized using standard synthesis methods well known in the art.

A detailed list of antisense polynucleotide agents targeting Factor XII is shown in Table 3.

Example 2

In Vitro Screening

Human hepatocarcinoma cells, Huh-7 cells, were obtained from American Type Culture Collection (Rockville, Md., cat. No. PTA-8561) and cultured in Dulbecco's MEM (Biochrom GmbH, Berlin #FG0435), supplemented to contain 10% fetal calf serum (FCS) (Biochrom AG, Berlin, Germany, cat. No. 50115), 200 µM L-Glutamin (Biochrom GmbH, Berlin, Germany, cat. No. K0283) and Penicillin 100 U/ml, Streptomycin 100 mg/ml (Biochrom GmbH, Berlin, Germany, cat. No. A2213), at 37° C. in an atmosphere with 5% $CO_2$ in a humidified incubator (Heraeus HERAcell, Kendro Laboratory Products, Langenselbold, Germany).

Transfection of Huh-7 cells with an antisense polynucleotide agent was performed directly after seeding 20,000 cells/well in a 96-well plate, and was carried out with Lipofectamine 2000 (Invitrogen GmbH, Karlsruhe, Germany, cat. No. 11668-019) as described by the manufacturer. Transfections were performed in quadruplicates and cells were transfected with theantisense polynucleotide agents at a concentration of 5 nM.

For measurement of FXII mRNA cells were harvested 24 hours after transfection and lysed at 53° C. following procedures recommended by the manufacturer of the Quantigene II Kit for FXII and Quantigene I Explore Kit for GAPDH (Affymetrix/eBioscience, Frankfurt, Germany, cat. No. 15735 or QG0004, respectively) bDNA. Afterwards, 50 µl of the lysates were incubated with probesets specific to human FXII and 10 µl of the lysates for human GAPDH and processed according to the manufacturer's protocol for QuantiGene. Chemoluminescence was measured in a Victor2-Light (Perkin Elmer, Wiesbaden, Germany) as RLUs (relative light units) and values obtained with the human FXII probeset were normalized to the respective human GAPDH values for each well and then related to the mean of three unrelated control antisense polynucleotide agents.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| a | 2'-O-methyladenosine-3'-phosphate |
| as | 2'-O-methyladenosine-3'-phosphorothioate |
| C | cytidine-3'-phosphate |
| dA | 2'-deoxyadenosine-3'-phosphate |
| dAs | 2'-deoxyadenosine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| c | 2'-O-methylcytidine-3'-phosphate |
| cs | 2'-O-methylcytidine-3'-phosphorothioate |
| dC | 2'-deoxycytidine-3'-phosphate |
| dCs | 2'-deoxycytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| g | 2'-O-methylguanosine-3'-phosphate |
| gs | 2'-O-methylguanosine-3'-phosphorothioate |
| dG | 2'-deoxyguanosine-3'-phosphate |
| dGs | 2'-deoxyguanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| t | 2'-O-methyl-5-methyluridine-3'-phosphate |
| ts | 2'-O-methyl-5-methyluridine-3'-phosphorothioate |
| dT | 2'-deoxythymidine-3'-phosphate |
| dTs | 2'-deoxythymidine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| u | 2'-O-methyluridine-3'-phosphate |
| us | 2'-O-methyluridine-3'-phosphorothioate |
| dU | 2'-deoxyuridine-3'-phosphate |
| dUs | 2'-deoxyuridine-3'-phosphorothioate |
| s | phosphorothioate linkage |
| N | any nucleotide (G, A, C, T or U) |
| L96 | N-[tris(GalNAc-alkyl)-amidodecanoyl)]-4-hydroxyprolinol Hyp-(GalNAc-alkyl)3 |
| (dt) | deoxy-thymine |
| (5MdC) | 5'-methyl-deoxycytidine-3'-phosphate |
| (5MdC)s | 5'-methyl-deoxycytidine-3'-phosphorothioate |

TABLE 3

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145494 | AGCUGCCTATCCAGGAGUCC | 9 | 11-30 | asgscsusgs(m5dCs)(m5dCs)dTsdAsdTs(m5dCs)(m5dCs)dAsdGsdGsasgsuscsc | 194 |
| A-145495 | CCGUUGGTCCAGCTGCCUAU | 10 | 21-40 | cscsgsusudsGsdGsdTs(m5dCs)(m5dCs)dAsdGs(m5dCs)dTsdGscscsusasu | 195 |
| A-145496 | AUGGCATCCGTCCGTUGGUC | 11 | 32-51 | asusgsgscsdAsdTs(m5dCs)(m5dCs)dGsdTs(m5dCs)(m5dCs)dGsdTsusgsgsusc | 196 |
| A-145497 | AGCAGAGCCCTCATGGCAUC | 12 | 44-63 | asgscsasgsdAsdGs(m5dCs)(m5dCs)(m5dCs)dTs(m5dCs)dAsdTsdGsgscsasusc | 197 |
| A-145498 | ACCCCAGGAGCAGCAGAGCC | 13 | 55-74 | ascscscscsdAsdGsdGsdAsdGs(m5dCs)dAsdGs(m5dCs)dAsgsasgscsc | 198 |
| A-145499 | ACCAGCAGGAACCCCAGGAG | 14 | 65-84 | ascscsasgs(m5dCs)dAsdGsdGsdAsdAs(m5dCs)(m5dCs)(m5dCs)(m5dCs)asgsgsasg | 199 |
| A-145500 | ACUCCAAGCTCACCAGCAGG | 15 | 76-95 | ascsuscscsdAsdAsdGs(m5dCs)dTs(m5dCs)dAs(m5dCs)(m5dCs)dAsgscsasgsg | 200 |
| A-145501 | CGAAAGTGTTGACTCCAAGC | 16 | 87-106 | csgsasasasdGsdTsdGsdTsdTsdGsdAs(m5dCs)dTs(m5dCs)csasasgsc | 201 |
| A-145502 | CCAAGGTGGAATCGAAAGUG | 17 | 99-118 | cscsasasgsdGsdTsdGsdGsdAsdAsdTs(m5dCs)dGsdAsasasgsusg | 202 |
| A-145503 | UGGGGGCTTCCCAAGGUGGA | 18 | 109-128 | usgsgsgsgsdGs(m5dCs)dTsdTs(m5dCs)(m5dCs)(m5dCs)dAsdAsdGsgsusgsgsa | 203 |
| A-145504 | ACUUATGCTCCTTGGGGGCU | 19 | 121-140 | ascsususasdTsdGs(m5dCs)dTs(m5dCs)(m5dCs)dTsdTsdGsdGsgsgsgscsu | 204 |
| A-145505 | CUUCAGCTTTGTACTUAUGC | 20 | 133-152 | csususcsasdGs(m5dCs)dTsdTsdTsdGsdTsdAs(m5dCs)dTsusasusgsc | 205 |
| A-145506 | ACUGUGTGCTCTTCAGCUUU | 21 | 143-162 | ascsusgsusdGsdTsdGs(m5dCs)dTs(m5dCs)dTsdTs(m5dCs)dAsgscsususu | 206 |
| A-145507 | ACAGUGAGAACGACTGUGUG | 22 | 155-174 | ascsasgsusdGsdAsdGsdAsdAs(m5dCs)dGsdAs(m5dCs)dTsgsusgsusg | 207 |
| A-145508 | UCCCCGGTGACAGTGAGAAC | 23 | 164-183 | uscscscscsdGsdGsdTsdGsdAs(m5dCs)dAsdGsdTsdGsasgsasasc | 208 |
| A-145509 | AGUGGCAGGGCTCCCCGGUG | 24 | 175-194 | asgsusgsgs(m5dCs)dAsdGsdGsdGs(m5dCs)dTs(m5dCs)(m5dCs)(m5dCs)csgsgsusg | 209 |
| A-145510 | ACUGGAAGGGGAAGTGGCAG | 25 | 187-206 | ascsusgsgsdAsdAsdGsdGsdGsdGsdAsdAsdGsdTsgsgscsasg | 210 |
| A-145511 | GCUGCCGGTGGTACTGGAAG | 26 | 199-218 | gscsusgscs(m5dCs)dGsdGsdTsdGsdGsdTsdAs(m5dCs)dTsgsgsasasg | 211 |
| A-145512 | UUGUGGTACAGCTGCCGGUG | 27 | 209-228 | ususgsusgsdGsdTsdAs(m5dCs)dAsdGs(m5dCs)dTsdGs(m5dCs)csgsgsusg | 212 |
| A-145513 | UGUGGGTACATTTGTGGUAC | 28 | 220-239 | usgsusgsgsdGsdTsdAs(m5dCs)dAsdTsdTsdTsdGsdTsgsgsusasc | 213 |
| A-145514 | UGGCCGGCCCTTGTGGGUAC | 29 | 231-250 | usgsgscscsdGsdGs(m5dCs)(m5dCs)(m5dCs)dTsdTsdGsdTsdGsgsgsusasc | 214 |
| A-145515 | GGCUGAGGGCCTGGCCGGCC | 30 | 242-261 | gsgscsusgsdAsdGsdGsdGs(m5dCs)(m5dCs)dTsdGsdGs(m5dCs)csgsgscsc | 215 |
| A-145516 | GUAGCACACCAGGGCUGAGG | 31 | 254-273 | gsusasgscsdAs(m5dCs)dAs(m5dCs)(m5dCs)dAsdGsdGsdGs(m5dCs)usgsasgsg | 216 |
| A-145517 | AGUUGGGGGTGGTAGCACAC | 32 | 265-284 | asgsususgsdGsdGsdGsdGsdTsdGsdGsdTsdAsdGscsascscasc | 217 |
| A-145518 | CCUGATCAAAGTTGGGGGUG | 33 | 274-293 | cscsusgsasdTs(m5dCs)dAsdAsdAsdGsdTsdTsdGsdGsgsgsgsusg | 218 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145519 | CCCCATCGCTGGTCCTGATC | 34 | 287-306 | cscscscsasdTs(m5dCs)dGs(m5dCs)dTsdGsdGsdTs(m5dCs)(m5dCs)usgsasusc | 219 |
| A-145520 | AAACAGTATCCCCATCGCTG | 35 | 296-315 | asasasascsasdGsdTsdAsdTs(m5dCs)(m5dCs)(m5dCs)(m5dCs)dAsdTscsgscsusg | 220 |
| A-145521 | UCUUGGGCTCCAAACAGUAU | 36 | 307-326 | uscsususgsdGsdGs(m5dCs)dTs(m5dCs)(m5dCs)dAsdAsdAs(m5dCs)asgsusasu | 221 |
| A-145522 | UGGUCUUUCACUUUCUUGGG | 37 | 320-339 | usgsgsuscsdTsdTsdTs(m5dCs)dAs(m5dCs)dTsdTsdTs(m5dCs)ususgsgsg | 222 |
| A-145523 | GUUUGCUGCAGUGGUCUUUC | 38 | 331-350 | gsusususgs(m5dCs)dTsdGs(m5dCs)dAsdGsdTsdGsdGsdTscsusususc | 223 |
| A-145524 | AGGGGCUGUGUUUGCUGCAG | 39 | 340-359 | asgsgsgsgs(m5dCs)dTsdGsdTsdGsdTsdTsdGs(m5dCs)usgscsasg | 224 |
| A-145525 | CUCCUUUCUGGCAGGGGCUG | 40 | 352-371 | csuscscsusdTsdTs(m5dCs)dTsdGsdGs(m5dCs)dAsdGsdGsgscsusg | 225 |
| A-145526 | ACACAGGTCCCTCCTTTCTG | 41 | 362-381 | ascsascsasdGsdGsdTs(m5dCs)(m5dCs)(m5dCs)dTs(m5dCs)(m5dCs)dTsususcsusg | 226 |
| A-145527 | UUGGCATGTTCACACAGGUC | 42 | 373-392 | ususgsgscsdAsdTsdGsdTsdTs(m5dCs)dAs(m5dCs)dAs(m5dCs)asgsgsusc | 227 |
| A-145528 | AGUGGGGCCGCUUGGCAUG | 43 | 385-404 | asgsusgsgsdGsdGsdGs(m5dCs)(m5dCs)dGs(m5dCs)dTsdTsdGsgscsasusg | 228 |
| A-145529 | GGACAGAGACAGUGGGGCC | 44 | 395-414 | gsgsascsasdGsdAsdGsdAs(m5dCs)dAsdGsdTsdGsdGsgsgsgscsc | 229 |
| A-145530 | UGAGGTGUUGUGGACAGAGA | 45 | 406-425 | usgsasgsgsdTsdGsdTsdTsdGsdTsdGsdGsdAs(m5dCs)asgsasgsa | 230 |
| A-145531 | AGUGGUUUCCAGUGAGGUGU | 46 | 418-437 | asgsusgsgsdTsdTsdTs(m5dCs)(m5dCs)dAsdGsdTsdGsdAsgsgsusgsu | 231 |
| A-145532 | UCUCUUUCUGGCAGTGGUUU | 47 | 430-449 | uscsuscsusdTsdTs(m5dCs)dTsdGsdGs(m5dCs)dAsdGsdTsgsgsususu | 232 |
| A-145533 | CAAAGCACTTCTCTTUCUGG | 48 | 439-458 | csasasasgs(m5dCs)dAs(m5dCs)dTsdTs(m5dCs)dTs(m5dCs)dTsdTsuscsusgsg | 233 |
| A-145534 | GAAGCTGAGGCUCAAAGCAC | 49 | 451-470 | gsasasgscsdTsdGsdAsdGsdGs(m5dCs)dTs(m5dCs)dAsdAsasgscsasc | 234 |
| A-145535 | GGAAAAACCGGAGAAGCUGA | 50 | 463-482 | gsgsasasasasdAsdAs(m5dCs)(m5dCs)dGsdGsdAsdGsdAsdAsgscsusgsa | 235 |
| A-145536 | CAUUCUUGTGGAAAAACCGG | 51 | 472-491 | csasususcsdTsdTsdGsdTsdGsdGsdAsdAsdAsdAsascscsgsg | 236 |
| A-145537 | AUACCAUAUCUCAUUCUUGU | 52 | 483-502 | asusascscsdAsdTsdAsdTs(m5dCs)dTs(m5dCs)dAsdTsdTscsususgsu | 237 |
| A-145538 | UGCUCAGUUCUAUACCAUAU | 53 | 494-513 | usgscsuscsdAsdGsdTsdTs(m5dCs)dTsdAsdTsdAs(m5dCs)csasusasu | 238 |
| A-145539 | GGCCACAGCUGCUUGCUCAG | 54 | 507-526 | gsgscscsas(m5dCs)dAsdGs(m5dCs)dTsdGs(m5dCs)dTsdTsdGscsuscsasg | 239 |
| A-145540 | ACUGGCAUCUGGCCACAGCU | 55 | 517-536 | ascsusgsgs(m5dCs)dAsdTs(m5dCs)dTsdGsdGs(m5dCs)(m5dCs)dAscsasgscsu | 240 |
| A-145541 | AGGACCCUUGCACUGGCAUC | 56 | 528-547 | asgsgsascscs(m5dCs)(m5dCs)dTsdTsdGs(m5dCs)dAsdTsdGsgscsasusc | 241 |
| A-145542 | AGUGGGCAUCAGGACCCUUG | 57 | 538-557 | asgsusgsgsgsdGs(m5dCs)dAsdTs(m5dCs)dAsdGsdGsdAs(m5dCs)cscsususg | 242 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145543 | CAGCCGCTGGCAGTGGGCAU | 58 | 549-568 | csasgscscsdGs(m5dCs)dTsdGsdGs(m5dCs)dAsdG sdTsdGsgsgscsasu | 243 |
| A-145544 | AGGCCTGGCTGGCCAGCCGC | 59 | 562-581 | asgsgscscsdTsdGsdGs(m5dCs)dTsdGsdGs (m5dCs)(m5dCs)dAsgscscsgsc | 244 |
| A-145545 | UGGUGCGGCAGGCCTGGCUG | 60 | 571-590 | usgsgsusgs(m5dCs)dGsdGs(m5dCs)dAsdGsdGs (m5dCs)(m5dCs)dTsgsgscsusg | 245 |
| A-145546 | GGAGGCACGGGTTGGUGCGG | 61 | 583-602 | gsgsasgsgs(m5dCs)dAs(m5dCs)dGsdGsdGsdTsdT sdGsdGsusgscsgsg | 246 |
| A-145547 | AGCGACCCCATGGAGGCAC | 62 | 595-614 | asgscsgsas(m5dCs)(m5dCs)(m5dCs)(m5dCs) (m5dCs)dAsdTsdGsdGsdAsgsgscsasc | 247 |
| A-145548 | ACCUCTAGGCAGCGACCCCC | 63 | 605-624 | ascscsuscsdTsdAsdGsdGs(m5dCs)dAsdGs (m5dCs)dGsdAscscscscsc | 248 |
| A-145549 | GGUGGCCCTCCACCTCUAGG | 64 | 616-635 | gsgsusgsgs(m5dCs)(m5dCs)(m5dCs)dTs(m5dCs) (m5dCs)dAs(m5dCs)(m5dCs)dTscsusasgsg | 249 |
| A-145550 | UGGCACAGGCGGTGGCCCUC | 65 | 626-645 | usgsgscsas(m5dCs)dAsdGsdGs(m5dCs)dGsdGsdT sdGsdGscscscsusc | 250 |
| A-145551 | CCCACCGGGCAGTGGCACAG | 66 | 638-657 | cscscsascs(m5dCs)dGsdGsdGs(m5dCs)dAsdGsdT sdGsdGscsascsasg | 251 |
| A-145552 | GCUCCGGTGTAGCCCACCGG | 67 | 650-669 | gscsuscscsdGsdGsdTsdGsdTsdAsdGs(m5dCs) (m5dCs)(m5dCs)ascscsgsg | 252 |
| A-145553 | CGUCGCAGAAGGCTCCGGUG | 68 | 661-680 | csgsuscsgs(m5dCs)dAsdGsdAsdAsdGsdGs (m5dCs)dTs(m5dCs)csgsgsusg | 253 |
| A-145554 | UGGUGTCCACGTCGCAGAAG | 69 | 670-689 | usgsgsusgsdTs(m5dCs)(m5dCs)dAs(m5dCs)dGsd Ts(m5dCs)dGs(m5dCs)asgsasasg | 254 |
| A-145555 | AGCAGCTTGCCTTGGUGUCC | 70 | 682-701 | asgscsasgs(m5dCs)dTsdTsdGs(m5dCs)(m5dCs)d TsdTsdGsdGsusgsuscsc | 255 |
| A-145556 | CGGCCATCATAGCAGCUUGC | 71 | 692-711 | csgsgscscsdAsdTs(m5dCs)dAsdTsdAsdGs (m5dCs)dAsdGscsususgsc | 256 |
| A-145557 | AGCUGAGCCCGCGGCCAUCA | 72 | 703-722 | asgscsusgsdAsdGs(m5dCs)(m5dCs)(m5dCs)dGs (m5dCs)dGsdGs(m5dCs)csasuscsa | 257 |
| A-145558 | GCCAGGCCGCGGTAGCUGAG | 73 | 716-735 | gscscsasgsdGs(m5dCs)dGs(m5dCs)dGsd GsdTsdAsdGscsusgsasg | 258 |
| A-145559 | CGUGGTCCTGGCCAGGCCGC | 74 | 726-745 | csgsusgsgsdTs(m5dCs)(m5dCs)dTsdGsdGs (m5dCs)(m5dCs)dAsdGsgscscsgsc | 259 |
| A-145560 | CACCCGAGAGCGTGGUCCUG | 75 | 736-755 | csascscscsdGsdAsdGsdAsdGs(m5dCs)dGsdTsdGs dGsuscscsusg | 260 |
| A-145561 | GCUGACAGGGCGCACCCGAG | 76 | 748-767 | gscsusgsas(m5dCs)dAsdGsdGsdGs(m5dCs)dGs (m5dCs)dAs(m5dCs)cscsgsasg | 261 |
| A-145562 | CGAGGCCCACGGCTGACAGG | 77 | 759-778 | csgsasgsgs(m5dCs)(m5dCs)(m5dCs)dAs(m5dCs) dGsdGs(m5dCs)dTsdGsascsasgsg | 262 |
| A-145563 | AGGUGGCCTCCGAGGCCCAC | 78 | 769-788 | asgsgsusgsdGs(m5dCs)(m5dCs)dTs(m5dCs) (m5dCs)dGsdAsdGsdGscscscsasc | 263 |
| A-145564 | GUCACGTTCCGGTAGGUGGC | 79 | 782-801 | gsuscsascsdGsdTsdTs(m5dCs)(m5dCs)dGsdGsdT sdAsdGsgsusgsgsc | 264 |
| A-145565 | CUUGCTCGGCAGTCACGUUC | 80 | 793-812 | csususgscsdTs(m5dCs)dGsdGs(m5dCs)dAsdGsdT s(m5dCs)dAscsgsusuusc | 265 |
| A-145566 | CCAGUTCCGCGCTTGCUCGG | 81 | 804-823 | cscsasgsusdTs(m5dCs)(m5dCs)dGs(m5dCs)dGs (m5dCs)dTsdTsdGscsuscsgsg | 266 |
| A-145567 | CGCCCAGTCCCCAGTUCCGC | 82 | 814-833 | csgscscscsdAsdGsdTs(m5dCs)(m5dCs)(m5dCs) (m5dCs)dAsdGsdTsuscscsgsc | 267 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145568 | AAGGCGTGGCCGCCCAGUCC | 83 | 824-843 | asasgsgscsdGsdTsdGsdGs(m5dCs)(m5dCs)dGs(m5dCs)(m5dCs)(m5dCs)asgsuscsc | 268 |
| A-145569 | GGGUUCCGGCAGAAGGCGUG | 84 | 836-855 | gsgsgsusus(m5dCs)(m5dCs)dGsdGs(m5dCs)dAsdGsdAsdAsdGsgscsgsusg | 269 |
| A-145570 | UGUCGUUGUCCGGGUUCCGG | 85 | 847-866 | usgsuscsgsdTsdTsdGsdTs(m5dCs)(m5dCs)dGsdGsdGsdTsuscscsgsg | 270 |
| A-145571 | ACCACGGGCGGATGTCGUUG | 86 | 859-878 | ascscsascsdGsdGsdGs(m5dCs)dGsdGsdAsdTsGsdTscsgsususg | 271 |
| A-145572 | AGCACGAAGCACCACGGGCG | 87 | 869-888 | asgscsascsdGsdAsdAsdGs(m5dCs)dAs(m5dCs)(m5dCs)dAs(m5dCs)gsgsgscsg | 272 |
| A-145573 | GGUCGCGGUUCAGCACGAAG | 88 | 880-899 | gsgsuscsgs(m5dCs)dGsdGsdGsdTsdTs(m5dCs)dAsdGs(m5dCs)dAscsgsasasg | 273 |
| A-145574 | CAGCUCAGCCGGUCGCGGUU | 89 | 890-909 | csasgscsus(m5dCs)dAsdGs(m5dCs)(m5dCs)dGsdGsdTs(m5dCs)dGscsgsgsusu | 274 |
| A-145575 | CGCAGTACTCCCAGCUCAGC | 90 | 901-920 | csgscsasgsdTsdAs(m5dCs)dTs(m5dCs)(m5dCs)(m5dCs)dAsdGs(m5dCs)uscsasgsc | 275 |
| A-145576 | ACUGUGCCAGGTCGCAGUAC | 91 | 913-932 | ascsusgsusdGs(m5dCs)(m5dCs)dAsdGsdGsdTs(m5dCs)dGs(m5dCs)asgsusasc | 276 |
| A-145577 | GGGGUCTGGCACTGTGCCAG | 92 | 923-942 | gsgsgsgsus(m5dCs)dTsdGsdGs(m5dCs)dAs(m5dCs)dTsdGsdTsgscscsasg | 277 |
| A-145578 | GCCGCCTGGGUUGGGGUCUG | 93 | 935-954 | gscscsgscs(m5dCs)dTsdGsdGsdGsdGsdTsdGsdGsdGsgsuscsusg | 278 |
| A-145579 | GGGGUCGGAGGCGCCGCCUG | 94 | 947-966 | gsgsgsgsus(m5dCs)dGsdGsdAsdGsdGs(m5dCs)dGs(m5dCs)(m5dCs)gscscsusg | 279 |
| A-145580 | AGGGGACACCGGGGUCGGAG | 95 | 957-976 | asgsgsgsgsdAs(m5dCs)dAs(m5dCs)(m5dCs)dGsdGsdGsdGsdTscsgsgsasg | 280 |
| A-145581 | ACAUGAAGCCTAGGGGACAC | 96 | 968-987 | ascsasusgsdAsdAsdGs(m5dCs)(m5dCs)dTsdAsdGsdGsdGsgsascsasc | 281 |
| A-145582 | GGCAUGAGTGGGACAUGAAG | 97 | 980-999 | gsgscsasusdGsdAsdGsdTsdGsdGsdGsdAs(m5dCs)dAsusgsasasg | 282 |
| A-145583 | CGGCUGCGCGGGCATGAGUG | 98 | 990-1009 | csgsgscsusdGs(m5dCs)dGs(m5dCs)dGsdGsdGs(m5dCs)dAsdTsgsasgsusg | 283 |
| A-145584 | UUCGGCGGTGCCGGCUGCGC | 99 | 1001-1020 | ususcsgsgs(m5dCs)dGsdGsdGsdGs(m5dCs)(m5dCs)dGsdGs(m5dCs)usgscsgsc | 284 |
| A-145585 | GGGCUGAGGCTTCGGCGGUG | 100 | 1011-1030 | gsgsgscsusdGsdAsdGsdGs(m5dCs)dTsdTs(m5dCs)dGsdGscsgsgsusg | 285 |
| A-145586 | GGUCCGGGTCGTGGGCUGAG | 101 | 1023-1042 | gsgsuscscsdGsdGsdGsdTs(m5dCs)dGsdTsdGsdGsdGscsusgsasg | 286 |
| A-145587 | ACUGAGGCGGGTCCGGGUC | 102 | 1033-1052 | ascsusgsasdGsdGs(m5dCs)dGsdGsdGsdGsdTs(m5dCs)(m5dCs)gsgsgsusc | 287 |
| A-145588 | CCGGGGTCTGGGACTGAGGC | 103 | 1045-1064 | cscsgsgsgsdGsdTs(m5dCs)dTsdGsdGsdGsdAs(m5dCs)dTsgsasgsgsc | 288 |
| A-145589 | GGCAAGGCTCCCGGGGUCUG | 104 | 1055-1074 | gsgscsasasdGsdGs(m5dCs)dTs(m5dCs)(m5dCs)(m5dCs)dGsdGsdGsgsuscsusg | 289 |
| A-145590 | UCCCGCTTCGCCGGCAAGGC | 105 | 1067-1086 | uscscscsgsdTsdTs(m5dCs)dGs(m5dCs)(m5dCs)dGsdGs(m5dCs)asasgsgsc | 290 |
| A-145591 | AAGGCGGCTGCTCCCGCUUC | 106 | 1078-1097 | asasgsgsgscsdGsdGs(m5dCs)dTsdGs(m5dCs)dTs(m5dCs)(m5dCs)(m5dCs)gscsususc | 291 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145592 | CUGGUCAGGGAAGGCGGCUG | 107 | 1088-1107 | csusgsgsus(m5dCs)dAsdGsdGsdGsdGsdAsdAsdGsdGs(m5dCs)gsgscsusg | 292 |
| A-145593 | AGUGGGCCGUUCCUGGUCAG | 108 | 1100-1119 | asgsusgsgsdGs(m5dCs)(m5dCs)dGsdTsdTs(m5dCs)(m5dCs)dTsdGsgsuscsasg | 293 |
| A-145594 | CCCGCAGCUCAGUGGGCCGU | 109 | 1110-1129 | cscscsgscsdAsdGs(m5dCs)dTs(m5dCs)dAsdGsdTsdGsdGsgscscsgsu | 294 |
| A-145595 | UGCGGAGCCGCUGCCCGCAG | 110 | 1123-1142 | usgscsgsgsdAsdGs(m5dCs)(m5dCs)dGs(m5dCs)dTsdGs(m5dCs)(m5dCs)csgscsasg | 295 |
| A-145596 | ACAGACUCUUGCGGAGCCGC | 111 | 1132-1151 | ascsasgsgsas(m5dCs)dTs(m5dCs)dTsdTsdTsdGs(m5dCs)dGsdGsdAsgscscsgsc | 296 |
| A-145597 | GGGUCAUCGAAGACAGACUC | 112 | 1144-1163 | gsgsgsuscsdAsdTs(m5dCs)dGsdAsdAsdGsdAs(m5dCs)dAsgsascsusc | 297 |
| A-145598 | CCAACGACGCGGGUCAUCGA | 113 | 1154-1173 | cscsasascsdGsdAs(m5dCs)dGs(m5dCs)dGsdGsdGsdTs(m5dCs)asuscsgsa | 298 |
| A-145599 | GCCACCAGCCCGCCAACGAC | 114 | 1166-1185 | gscscsascs(m5dCs)dAsdGs(m5dCs)(m5dCs)(m5dCs)dGs(m5dCs)(m5dCs)dAsascsgsasc | 299 |
| A-145600 | GCCCCGCGUAGCGCCACCAG | 115 | 1178-1197 | gscscscscsdGs(m5dCs)dGsdTsdAsdGs(m5dCs)dGs(m5dCs)(m5dCs)ascscsasg | 300 |
| A-145601 | UAGGGGUGCGCCCCGCGUAG | 116 | 1187-1206 | usasgsgsgsdGsdTsdGs(m5dCs)dGs(m5dCs)(m5dCs)(m5dCs)(m5dCs)dGscsgsusasg | 301 |
| A-145602 | AGCGCGGCGAUGUAGGGGUG | 117 | 1199-1218 | asgscsgscsdGsdGs(m5dCs)dGsdAsdTsdGsdTsdAsdGsgsgsgsusg | 302 |
| A-145603 | GGCCCCAGUACAGCGCGGCG | 118 | 1210-1229 | gsgscscscs(m5dCs)dAsdGsdTsdAs(m5dCs)dAsdGs(m5dCs)dGscsgsgscsg | 303 |
| A-145604 | GCAGAAACUGUGGCCCCAGU | 119 | 1221-1240 | gscsasgsasdAsdAs(m5dCs)dTsdGsdTsdGsdGs(m5dCs)(m5dCs)cscsasgsu | 304 |
| A-145605 | GAGGCUGCCGGCGCAGAAAC | 120 | 1233-1252 | gsasgsgscsdTsdGs(m5dCs)(m5dCs)dGsdGs(m5dCs)dGs(m5dCs)dAsgsasasasc | 305 |
| A-145606 | GGGGGCGAUGAGGCUGCCGG | 121 | 1242-1261 | gsgsgsgsgs(m5dCs)dGsdAsdTsdGsdAsdGsdGs(m5dCs)dTsgscscsgsg | 306 |
| A-145607 | AGCACCCAGCAGGGGGCGAU | 122 | 1253-1272 | asgscsascs(m5dCs)(m5dCs)dAsdGs(m5dCs)dAsdGsdGsdGsdGsgscsgsasu | 307 |
| A-145608 | GAGCGGCCGUCAGCACCCAG | 123 | 1264-1283 | gsasgscsgsdGs(m5dCs)(m5dCs)dGsdTs(m5dCs)dAsdGs(m5dCs)dAscscscsasg | 308 |
| A-145609 | CCUGCAGGCAGUGAGCGGCC | 124 | 1276-1295 | cscsusgscsdAsdGsdGs(m5dCs)dAsdGsdTsdGsdAsdGscsgsgscsc | 309 |
| A-145610 | GUGCGGGCCGGUCCUGCAGG | 125 | 1288-1307 | gsusgscsgsdGsdGs(m5dCs)(m5dCs)dGsdGsdTs(m5dCs)(m5dCs)dTsgscsasgsg | 310 |
| A-145611 | AGAUCCUCGGGUGCGGCCG | 126 | 1298-1317 | asgsasuscs(m5dCs)dTs(m5dCs)dGsdGsdGsdTsdGs(m5dCs)dGsgsgscscsg | 311 |
| A-145612 | CACCACCGUCAGAUCCUCGG | 127 | 1308-1327 | csascscsas(m5dCs)(m5dCs)dGsdTs(m5dCs)dAsdGsdAsdTs(m5dCs)csuscsgsg | 312 |
| A-145613 | GUUCCUGGCCGAGCACCACC | 128 | 1321-1340 | gsususcscsdTsdGsdGs(m5dCs)(m5dCs)dGsdAsdGs(m5dCs)dAscscsascsc | 313 |
| A-145614 | UGGUUACGGCGUUCCUGGCC | 129 | 1331-1350 | usgsgsususdAs(m5dCs)dGsdGs(m5dCs)dGsdTsdTs(m5dCs)(m5dCs)usgsgscsc | 314 |
| A-145615 | GCUCACAGCUGUGGUACGG | 130 | 1342-1361 | gscsuscsas(m5dCs)dAsdGs(m5dCs)dTsdGsdTsdGsdGsdTsusascsgsg | 315 |
| A-145616 | ACGUCUGGCACGGCUCACAG | 131 | 1354-1373 | ascsgsuscsdTsdGsdGs(m5dCs)dAs(m5dCs)dGsdGs(m5dCs)dTscscsascscsasg | 316 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145617 | GCACGGCCAACGTCTGGCAC | 132 | 1363-1382 | gscsascsgsdGs(m5dCs)(m5dCs)dAsdAs(m5dCs)dGsdTs(m5dCs)dTsgsgscsasc | 317 |
| A-145618 | AGCGGTAGGAGCGCACGGCC | 133 | 1375-1394 | asgscsgsgsdTsdAsdGsdGsdAsdGs(m5dCs)dGs(m5dCs)dAscsgsgscsc | 318 |
| A-145619 | AGGCCTCGTGCAAGCGGUAG | 134 | 1387-1406 | asgsgscscsdTs(m5dCs)dGsdTsdGs(m5dCs)dAsdAsdGs(m5dCs)gsgsusasg | 319 |
| A-145620 | ACGGGCGAGAAGGCCUCGUG | 135 | 1397-1416 | ascsgsgsgs(m5dCs)dGsdAsdGsdAsdAsdGsdGs(m5dCs)(m5dCs)uscsgsusg | 320 |
| A-145621 | GCUGGTAGCTGACGGGCGAG | 136 | 1408-1427 | gscsusgsgsdTsdAsdGs(m5dCs)dTsdGsdAs(m5dCs)dGsdGsgscsgsasg | 321 |
| A-145622 | AGCCAGGTCGTGCTGGUAGC | 137 | 1419-1438 | asgscscsasdGsdGsdTs(m5dCs)dGsdTsdGs(m5dCs)dTsdGsgsusasgsc | 322 |
| A-145623 | AGGCGCAACAGAGCCAGGUC | 138 | 1430-1449 | asgsgscscsgs(m5dCs)dAsdAs(m5dCs)dAsdGsdAsdGs(m5dCs)(m5dCs)asgsgsusc | 323 |
| A-145624 | CAUCCTCCTGAAGGCGCAAC | 139 | 1441-1460 | csasuscscsdTs(m5dCs)(m5dCs)dTsdGsdAsdAsdGsdGs(m5dCs)gscsasasc | 324 |
| A-145625 | AGCUGCCGTCCGCATCCUCC | 140 | 1453-1472 | asgscsusgs(m5dCs)(m5dCs)dGsdTs(m5dCs)(m5dCs)dGs(m5dCs)dAsdTscscsuscsc | 325 |
| A-145626 | AGGAGCGCGCAGCTGCCGUC | 141 | 1463-1482 | asgsgsasgs(m5dCs)dGs(m5dCs)dGs(m5dCs)dAsdGs(m5dCs)dTsdGscscsgsusc | 326 |
| A-145627 | ACGUAAGGCGACAGGAGCGC | 142 | 1475-1494 | ascsgsusasdAsdGsdGs(m5dCs)dAsdGsdGsasgscsgsc | 327 |
| A-145628 | ACACCGGCTGAACGTAAGGC | 143 | 1486-1505 | ascsasascscsdGsdGs(m5dCs)dTsdGsdAsdAs(m5dCs)dGsdTsasasgsgsc | 328 |
| A-145629 | CUUGGCAGGCACACCGGCUG | 144 | 1496-1515 | csususgsgs(m5dCs)dAsdGsdGs(m5dCs)dAs(m5dCs)dAs(m5dCs)(m5dCs)gsgscsusg | 329 |
| A-145630 | CGCGCGGCGCCGCTTGGCAG | 145 | 1508-1527 | csgscsgscsdGsdGs(m5dCs)dGs(m5dCs)(m5dCs)dGs(m5dCs)dTsdTsgsgscsasg | 330 |
| A-145631 | UCGGAGGGTCGCGCGGCGCC | 146 | 1517-1536 | uscsgsgsasdGsdGsdGsdTs(m5dCs)dGs(m5dCs)dGs(m5dCs)dGsgscsgscsc | 331 |
| A-145632 | AGAGCGTGGTCTCGGAGGGU | 147 | 1528-1547 | asgsasgscsdGsdTsdGsdGsdTs(m5dCs)dTs(m5dCs)dGsdGsasgsgsgsu | 332 |
| A-145633 | CCGGCCACCTGGCAGAGCGU | 148 | 1541-1560 | cscsgsgscs(m5dCs)dAs(m5dCs)(m5dCs)dTsdGsdGs(m5dCs)dAsdGsasgscsgsu | 333 |
| A-145634 | UGGCCCAGCCGGCCACCUG | 149 | 1550-1569 | usgsgscscs(m5dCs)(m5dCs)dAsdGs(m5dCs)(m5dCs)dGsdGs(m5dCs)(m5dCs)ascscsusg | 334 |
| A-145635 | CCUCGAACTGGTGGCCCCAG | 150 | 1561-1580 | cscsuscsgsdAsdAs(m5dCs)dTsdGsdGsdTsdGsdGs(m5dCs)cscscsasg | 335 |
| A-145636 | AUUCCTCCGCCCCCTCGAAC | 151 | 1573-1592 | asususcscsdTs(m5dCs)(m5dCs)dGs(m5dCs)(m5dCs)(m5dCs)(m5dCs)(m5dCs)dTscsgsasasc | 336 |
| A-145637 | AAGCUGGCATATTCCUCCGC | 152 | 1583-1602 | asasgscsusdGsdGs(m5dCs)dAsdTsdAsdTsdTs(m5dCs)(m5dCs)uscscsgsc | 337 |
| A-145638 | CGCCUCCTGCAGGAAGCUGG | 153 | 1596-1615 | csgscscsus(m5dCs)(m5dCs)dTsdGs(m5dCs)dAsdGsdGsdAsdAsgscsusgsg | 338 |
| A-145639 | AACGGTACCTGCGCCUCCUG | 154 | 1607-1626 | asasascsgsgsdTsdAs(m5dCs)(m5dCs)dTsdGs(m5dCs)dGs(m5dCs)(m5dCs)uscscsusg | 339 |
| A-145640 | AGGGAGAGGAACGGTACCUG | 155 | 1616-1635 | asgsgsgsgsasdAsdGsdAsdGsdGsdAsdAs(m5dCs)dGsdGsdTsascscsusg | 340 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145641 | AGCAGCGCTCCAGGGAGAGG | 156 | 1627-1646 | asgscsasgs(m5dCs)dGs(m5dCs)dTs(m5dCs)(m5dCs)dAsdGsdGsdGsasgsasgsg | 341 |
| A-145642 | CGUCCGGGCTGAGCAGCGC | 157 | 1639-1658 | csgsuscscsdGsdGsdGsdDs(m5dCs)dTsdGsdAsdGs(m5dCs)asgscsgsc | 342 |
| A-145643 | AGGAUCCGTGCACGTCCGGG | 158 | 1651-1670 | asgsgsasus(m5dCs)(m5dCs)dGsdTsdGs(m5dCs)dAs(m5dCs)dGsdTscscsgsgsg | 343 |
| A-145644 | GGGGAGGATGGAGGAUCCGU | 159 | 1662-1681 | gsgsgsgsasdGsdGsdAsdTsdGsdGsdAsdGsdGsdAsuscscsgsu | 344 |
| A-145645 | GAGCATGCCGGGGAGGAUGG | 160 | 1671-1690 | gsasgscsasdTsdGs(m5dCs)(m5dCs)dGsdGsdGsdGsdAsdGsgsasusgsg | 345 |
| A-145646 | GAACCCTGCGCAGAGCAUGC | 161 | 1683-1702 | gsasascscs(m5dCs)dTsdGs(m5dCs)dGs(m5dCs)dAsdGsdAsdGscsasusgsc | 346 |
| A-145647 | GCCGCCCTCGAGGAACCCUG | 162 | 1695-1714 | gscscsgscs(m5dCs)(m5dCs)dTs(m5dCs)dGsdAsdGsdGsdAscscscsusg | 347 |
| A-145648 | ACGCATCGGTGCCGCCCUCG | 163 | 1705-1724 | ascsgscsasdTs(m5dCs)dGsdGsdTsdGs(m5dCs)(m5dCs)dGs(m5dCs)cscsuscsg | 348 |
| A-145649 | AAUCACCCTGGCACGCAUCG | 164 | 1717-1736 | asasasuscsas(m5dCs)(m5dCs)(m5dCs)dTsdGsdGs(m5dCs)dAs(m5dCs)dGscsasuscsg | 349 |
| A-145650 | GGGCCTCCGGAATCACCCUG | 165 | 1727-1746 | gsgsgscscsdTs(m5dCs)(m5dCs)dGsdGsdAsdAsdTs(m5dCs)dAscscscsusg | 350 |
| A-145651 | ACACACCAGCGGGCCUCCGG | 166 | 1737-1756 | ascsascsasdCs(m5dCs)(m5dCs)dAsdGs(m5dCs)dGsdGsdGs(m5dCs)(m5dCs)uscscsgsg | 351 |
| A-145652 | AGCUUGGTCCTCACACACCA | 167 | 1749-1768 | asgscsusus dGsdGsdTs(m5dCs)(m5dCs)dTs(m5dCs)dAs(m5dCs)dAscsascscsa | 352 |
| A-145653 | CCGGCGCTCTGCAGCUUGGU | 168 | 1761-1780 | cscsgsgscsdGs(m5dCs)dTs(m5dCs)dTsdGs(m5dCs)dAsdGs(m5dCs)ususgsgsu | 353 |
| A-145654 | CAGGGTGAGCCGGCGCUCUG | 169 | 1770-1789 | csasgsgsgsdTsdGsdAsdGs(m5dCs)(m5dCs)dGsdGs(m5dCs)dGscsuscsusg | 354 |
| A-145655 | AUGAUGCCTTGCAGGGUGAG | 170 | 1781-1800 | asusgsasusdGs(m5dCs)(m5dCs)dTsdTsdGs(m5dCs)dAsdGsdGsgsusgsasg | 355 |
| A-145656 | AUCCCCAGCTGATGAUGCCU | 171 | 1792-1811 | asuscscscs(m5dCs)dAsdGs(m5dCs)dTsdGsdAsdTsdGsdAsusgscscsu | 356 |
| A-145657 | ACCACAGCCCGATCCCCAGC | 172 | 1803-1822 | ascscsascsdAsdGs(m5dCs)(m5dCs)(m5dCs)dGsdAsdTs(m5dCs)(m5dCs)cscsasgsc | 357 |
| A-145658 | GCUUGTTGCGGTCACCACAG | 173 | 1816-1835 | gscsusus usgsdTsdTsdGs(m5dCs)dGsdGsdTs(m5dCs)dAs(m5dCs)csascsasg | 358 |
| A-145659 | GUAGACGCCTGGCTTGUUGC | 174 | 1827-1846 | gsusasgsas(m5dCs)dGs(m5dCs)(m5dCs)dTsdGsdGs(m5dCs)dTsdTsgsususgsc | 359 |
| A-145660 | CACAUCGGTGTAGACGCCUG | 175 | 1836-1855 | csascsasus(m5dCs)dGsdGsdTsdGsdTsdAsdGsdAs(m5dCs)gscscsusg | 360 |
| A-145661 | CCAGGTAGTAGGCCACAUCG | 176 | 1849-1868 | cscsasgsgsdTsdAsdGsdTsdAsdGsdGs(m5dCs)(m5dCs)dAscsasuscsg | 361 |
| A-145662 | GGAUCCAGGCCAGGTAGUAG | 177 | 1858-1877 | gsgsasusces(m5dCs)dAsdGsdGs(m5dCs)(m5dCs)dAsdGsdGsdTsasgsusasg | 362 |
| A-145663 | GGUGUGCTCCCGGATCCAGG | 178 | 1869-1888 | gsgsusgsusdGs(m5dCs)dTs(m5dCs)(m5dCs)(m5dCs)dGsdGsdAsdTscscsasgsg | 363 |
| A-145664 | AAUCAGGAAACGGTGUGCUC | 179 | 1880-1899 | asasuscsasdGsdGsdAsdAsdAs(m5dCs)dGsdGsdTsdGsusgscsusc | 364 |
| A-145665 | AGUCCCTGAGCAATCAGGAA | 180 | 1891-1910 | asgsuscscs(m5dCs)dTsdGsdAsdGs(m5dCs)dAsdAsdTs(m5dCs)asgsgsasa | 365 |

TABLE 3-continued

Antisense polynucleotide agents targeting Factor XII.

| Oligo Name | Unmodified Sequence (5' to 3') | SEQ ID NO: | Target site on SEQ ID 1 | Modified Sequence (5' to 3') | SEQ ID NO: |
|---|---|---|---|---|---|
| A-145666 | AGGGAAAGATGAGTCCCTGA | 181 | 1902-1921 | asgsgsgsasdAsdAsdGsdAsdTsdGsdAsdGsdTs(m5dCs)cscsusgsa | 366 |
| A-145667 | GAAUCACCAAGGAGGGAAAG | 182 | 1914-1933 | gsasasuscsdAs(m5dCs)(m5dCs)dAsdAsdGsdGsdAsdGsdGsgsasasasg | 367 |
| A-145668 | UCUCACTGCGGAATCACCAA | 183 | 1924-1943 | uscsuscsas(m5dCs)dTsdGs(m5dCs)dGsdGsdAsdAsdTs(m5dCs)ascscsasa | 368 |
| A-145669 | CCCCAGCCACTCTCTCACTG | 184 | 1936-1955 | cscscscsasdGs(m5dCs)(m5dCs)dAs(m5dCs)dTs(m5dCs)dTs(m5dCs)dTscsascsusg | 369 |
| A-145670 | UUGCCTTCCATGCCCCAGCC | 185 | 1948-1967 | ususgscscsdTsdTs(m5dCs)(m5dCs)dAsdTsdGs(m5dCs)(m5dCs)(m5dCs)csasgscsc | 370 |
| A-145671 | GACACAATCTTGCCTUCCAU | 186 | 1957-1976 | gsascsascsdAsdAsdTs(m5dCs)dTsdTsdGs(m5dCs)(m5dCs)dTsuscscsasu | 371 |
| A-145672 | CUGGGGGAATGGGACACAAU | 187 | 1969-1988 | csusgsgsgsdGsdGsdAsdAsdTsdGsdGsdGsdAs(m5dCs)ascsasasu | 372 |
| A-145673 | AGCUGGCCGCACTGGGGGAA | 188 | 1980-1999 | asgscsusgsdGs(m5dCs)(m5dCs)dGs(m5dCs)dAs(m5dCs)dTsdGsdGsgsgsgsasa | 373 |
| A-145674 | AUCCUGGCGCGGAGCUGGCC | 189 | 1992-2011 | asuscscsusdGsdGs(m5dCs)dGs(m5dCs)dGsdGsdAsdGs(m5dCs)usgsgscsc | 374 |
| A-145675 | GUUCCTGCGCCATCCUGGCG | 190 | 2003-2022 | gsususcscsdTsdGs(m5dCs)dGs(m5dCs)(m5dCs)dAsdTs(m5dCs)(m5dCs)usgsgscsg | 375 |
| A-145676 | CACUUTATTGAGTTCCUGCG | 191 | 2014-2033 | csascsusudTsdAsdTsdTsdGsdAsdGsdTsdTs(m5dCs)csusgscsg | 376 |
| A-145677 | AUUUUCAAAGCACTTUAUUG | 192 | 2024-2043 | asusususus(m5dCs)dAsdAsdAsdGs(m5dCs)dAs(m5dCs)dTsdTsusasususg | 377 |
| A-145678 | UUUUUCTCAGCATTTUCAAA | 193 | 2035-2054 | ususususus(m5dCs)dTs(m5dCs)dAsdGs(m5dCs)dAsdTsdTsdTsuscsasasa | 378 |

TABLE 4

Factor XII single dose screen in primary human cells

| Oligo Name | % Residual mRNA | SD | Target site on SEQ ID 1 |
|---|---|---|---|
| A-145494 | 77% | 7% | 11-30 |
| A-145495 | 54% | 7% | 21-40 |
| A-145496 | 54% | 6% | 32-51 |
| A-145497 | 56% | 6% | 44-63 |
| A-145498 | 57% | 7% | 55-74 |
| A-145499 | 65% | 13% | 65-84 |
| A-145500 | 66% | 3% | 76-95 |
| A-145501 | 57% | 6% | 87-106 |
| A-145502 | 76% | 8% | 99-118 |
| A-145503 | 71% | 11% | 109-128 |
| A-145504 | 94% | 14% | 121-140 |
| A-145505 | 73% | 10% | 133-152 |
| A-145506 | 42% | 4% | 143-162 |
| A-145507 | 54% | 11% | 155-174 |
| A-145508 | 57% | 8% | 164-183 |
| A-145509 | 66% | 9% | 175-194 |
| A-145510 | 81% | 7% | 187-206 |
| A-145511 | 65% | 6% | 199-218 |
| A-145512 | 48% | 3% | 209-228 |
| A-145513 | 58% | 13% | 220-239 |
| A-145514 | 66% | 13% | 231-250 |
| A-145515 | 69% | 9% | 242-261 |
| A-145516 | 53% | 13% | 254-273 |
| A-145517 | 66% | 11% | 265-284 |
| A-145518 | 66% | 13% | 274-293 |
| A-145519 | 31% | 5% | 287-306 |
| A-145520 | 32% | 6% | 296-315 |
| A-145521 | 69% | 5% | 307-326 |
| A-145522 | 52% | 4% | 320-339 |
| A-145523 | 45% | 6% | 331-350 |
| A-145524 | 63% | 11% | 340-359 |
| A-145525 | 52% | 5% | 352-371 |
| A-145526 | 56% | 6% | 362-381 |
| A-145527 | 28% | 4% | 373-392 |
| A-145528 | 60% | 15% | 385-404 |
| A-145529 | 53% | 6% | 395-414 |
| A-145530 | 69% | 13% | 406-425 |
| A-145531 | 60% | 6% | 418-437 |
| A-145532 | 37% | 7% | 430-449 |
| A-145533 | 40% | 4% | 439-458 |
| A-145534 | 51% | 3% | 451-470 |
| A-145535 | 70% | 11% | 463-482 |
| A-145536 | 48% | 5% | 472-491 |
| A-145537 | 38% | 9% | 483-502 |
| A-145538 | 31% | 2% | 494-513 |
| A-145539 | 27% | 5% | 507-526 |
| A-145540 | 33% | 4% | 517-536 |
| A-145541 | 36% | 5% | 528-547 |

TABLE 4-continued

Factor XII single dose screen in primary human cells

| Oligo Name | % Residual mRNA | SD | Target site on SEQ ID 1 |
|---|---|---|---|
| A-145542 | 36% | 5% | 538-557 |
| A-145543 | 46% | 4% | 549-568 |
| A-145544 | 96% | 11% | 562-581 |
| A-145545 | 104% | 3% | 571-590 |
| A-145546 | 70% | 5% | 583-602 |
| A-145547 | 33% | 11% | 595-614 |
| A-145548 | 28% | 4% | 605-624 |
| A-145549 | 28% | 3% | 616-635 |
| A-145550 | 33% | 5% | 626-645 |
| A-145551 | 33% | 4% | 638-657 |
| A-145552 | 45% | 8% | 650-669 |
| A-145553 | 59% | 5% | 661-680 |
| A-145554 | 71% | 9% | 670-689 |
| A-145555 | 36% | 4% | 682-701 |
| A-145556 | 30% | 4% | 692-711 |
| A-145557 | 46% | 11% | 703-722 |
| A-145558 | 68% | 15% | 716-735 |
| A-145559 | 64% | 11% | 726-745 |
| A-145560 | 57% | 5% | 736-755 |
| A-145561 | 41% | 8% | 748-767 |
| A-145562 | 50% | 6% | 759-778 |
| A-145563 | 58% | 12% | 769-788 |
| A-145564 | 53% | 3% | 782-801 |
| A-145565 | 35% | 4% | 793-812 |
| A-145566 | 27% | 6% | 804-823 |
| A-145567 | 22% | 4% | 814-833 |
| A-145568 | 34% | 9% | 824-843 |
| A-145569 | 40% | 10% | 836-855 |
| A-145570 | 29% | 9% | 847-866 |
| A-145571 | 36% | 11% | 859-878 |
| A-145572 | 20% | 2% | 869-888 |
| A-145573 | 28% | 5% | 880-899 |
| A-145574 | 61% | 10% | 890-909 |
| A-145575 | 34% | 11% | 901-920 |
| A-145576 | 49% | 4% | 913-932 |
| A-145577 | 50% | 7% | 923-942 |
| A-145578 | 61% | 7% | 935-954 |
| A-145579 | 71% | 16% | 947-966 |
| A-145580 | 62% | 10% | 957-976 |
| A-145581 | 58% | 8% | 968-987 |
| A-145582 | 67% | 5% | 980-999 |
| A-145583 | 48% | 8% | 990-1009 |
| A-145584 | 35% | 4% | 1001-1020 |
| A-145585 | 43% | 4% | 1011-1030 |
| A-145586 | 39% | 3% | 1023-1042 |
| A-145587 | 59% | 12% | 1033-1052 |
| A-145588 | 50% | 4% | 1045-1064 |
| A-145589 | 52% | 12% | 1055-1074 |
| A-145590 | 57% | 5% | 1067-1086 |
| A-145591 | 56% | 8% | 1078-1097 |
| A-145592 | 70% | 19% | 1088-1107 |
| A-145593 | 45% | 9% | 1100-1119 |
| A-145594 | 32% | 3% | 1110-1129 |
| A-145595 | 43% | 8% | 1123-1142 |
| A-145596 | 36% | 5% | 1132-1151 |
| A-145597 | 29% | 3% | 1144-1163 |
| A-145598 | 45% | 5% | 1154-1173 |
| A-145599 | 36% | 6% | 1166-1185 |
| A-145600 | 29% | 3% | 1178-1197 |
| A-145601 | 51% | 8% | 1187-1206 |
| A-145602 | 69% | 10% | 1199-1218 |
| A-145603 | 37% | 5% | 1210-1229 |
| A-145604 | 41% | 15% | 1221-1240 |
| A-145605 | 53% | 16% | 1233-1252 |
| A-145606 | 68% | 18% | 1242-1261 |
| A-145607 | 52% | 11% | 1253-1272 |
| A-145608 | 66% | 21% | 1264-1283 |
| A-145609 | 69% | 25% | 1276-1295 |
| A-145610 | 64% | 14% | 1288-1307 |
| A-145611 | 57% | 10% | 1298-1317 |
| A-145612 | 38% | 11% | 1308-1327 |
| A-145613 | 44% | 5% | 1321-1340 |
| A-145614 | 54% | 11% | 1331-1350 |
| A-145615 | 44% | 7% | 1342-1361 |
| A-145616 | 35% | 4% | 1354-1373 |
| A-145617 | 36% | 7% | 1363-1382 |
| A-145618 | 43% | 8% | 1375-1394 |
| A-145619 | 31% | 3% | 1387-1406 |
| A-145620 | 64% | 27% | 1397-1416 |
| A-145621 | 75% | 12% | 1408-1427 |
| A-145622 | 71% | 27% | 1419-1438 |
| A-145623 | 49% | 8% | 1430-1449 |
| A-145624 | 47% | 6% | 1441-1460 |
| A-145625 | 48% | 11% | 1453-1472 |
| A-145626 | 49% | 12% | 1463-1482 |
| A-145627 | 57% | 14% | 1475-1494 |
| A-145628 | 56% | 9% | 1486-1505 |
| A-145629 | 47% | 10% | 1496-1515 |
| A-145630 | 64% | 10% | 1508-1527 |
| A-145631 | 60% | 11% | 1517-1536 |
| A-145632 | 62% | 6% | 1528-1547 |
| A-145633 | 45% | 14% | 1541-1560 |
| A-145634 | 61% | 9% | 1550-1569 |
| A-145635 | 66% | 17% | 1561-1580 |
| A-145636 | 79% | 12% | 1573-1592 |
| A-145637 | 55% | 8% | 1583-1602 |
| A-145638 | 64% | 7% | 1596-1615 |
| A-145639 | 65% | 3% | 1607-1626 |
| A-145640 | 78% | 10% | 1616-1635 |
| A-145641 | 92% | 9% | 1627-1646 |
| A-145642 | 67% | 8% | 1639-1658 |
| A-145643 | 61% | 9% | 1651-1670 |
| A-145644 | 62% | 10% | 1662-1681 |
| A-145645 | 83% | 13% | 1671-1690 |
| A-145646 | 47% | 3% | 1683-1702 |
| A-145647 | 56% | 10% | 1695-1714 |
| A-145648 | 86% | 9% | 1705-1724 |
| A-145649 | 79% | 9% | 1717-1736 |
| A-145650 | 50% | 5% | 1727-1746 |
| A-145651 | 38% | 3% | 1737-1756 |
| A-145652 | 57% | 9% | 1749-1768 |
| A-145653 | 69% | 9% | 1761-1780 |
| A-145654 | 80% | 34% | 1770-1789 |
| A-145655 | 36% | 6% | 1781-1800 |
| A-145656 | 30% | 3% | 1792-1811 |
| A-145657 | 33% | 4% | 1803-1822 |
| A-145658 | 29% | 6% | 1816-1835 |
| A-145659 | 30% | 7% | 1827-1846 |
| A-145660 | 25% | 4% | 1836-1855 |
| A-145661 | 28% | 4% | 1849-1868 |
| A-145662 | 51% | 7% | 1858-1877 |
| A-145663 | 36% | 3% | 1869-1888 |
| A-145664 | 42% | 3% | 1880-1899 |
| A-145665 | 37% | 6% | 1891-1910 |
| A-145666 | 22% | 5% | 1902-1921 |
| A-145667 | 19% | 5% | 1914-1933 |
| A-145668 | 15% | 6% | 1924-1943 |
| A-145669 | 13% | 3% | 1936-1955 |
| A-145670 | 23% | 8% | 1948-1967 |
| A-145671 | 30% | 5% | 1957-1976 |
| A-145672 | 57% | 14% | 1969-1988 |
| A-145673 | 66% | 18% | 1980-1999 |
| A-145674 | 24% | 4% | 1992-2011 |
| A-145675 | 30% | 6% | 2003-2022 |
| A-145676 | 25% | 3% | 2014-2033 |
| A-145677 | 44% | 9% | 2024-2043 |
| A-145678 | 70% | 14% | 2035-2054 |

I claim:

1. A single stranded antisense polynucleotide agent for inhibiting expression of a Factor XII (F12) gene, wherein the agent comprises 14 to 20 contiguous nucleotides, wherein at least one of the contiguous nucleotides is a modified nucleotide, and wherein the nucleotide sequence of the agent is fully complementary over its entire length to nucleotides 287-306 of SEQ ID NO:1.

2. The agent of claim 1, wherein substantially all of the nucleotides of the antisense polynucleotide agent are modified nucleotides.

3. The agent of claim 1, wherein all of the nucleotides of the antisense polynucleotide agent are modified nucleotides.

4. The agent of claim 1, which is 14 nucleotides in length or 20 nucleotides in length.

5. The agent of claim 1, wherein the modified nucleotide comprises a modified sugar moiety selected from the group consisting of: a 2'-O-methoxyethyl modified sugar moiety, a 2'-methoxy modified sugar moiety, a 2'-O-alkyl modified sugar moiety, a bicyclic sugar moiety, a 5-methylcytosine, and a modified internucleoside linkage.

6. The agent of claim 5, wherein the bicyclic sugar moiety has a (—CRH—)n group forming a bridge between the 2' oxygen and the 4' carbon atoms of the sugar ring, wherein n is 1 or 2 and wherein R is H, $CH_3$ or $CH_3OCH_3$.

7. The agent of claim 5, wherein the modified internucleoside linkage is a phosphorothioate internucleoside linkage.

8. The agent of claim 1, wherein the agent is a gapmer comprising a plurality of 2'-deoxynucleotides flanked on each of a 5' and a 3' side by a wing segment comprising at least one nucleotide having a modified sugar moiety.

9. The agent of claim 8, wherein the modified sugar moiety is selected from the group consisting of a 2'-O-methoxyethyl modified sugar moiety, a 2'-methoxy modified sugar moiety, a 2'-O-alkyl modified sugar moiety, and a bicyclic sugar moiety.

10. The agent of claim 8, wherein the 5'-wing segment is 1 to 6 nucleotides in length; 2 nucleotides in length; 3 nucleotides in length; 4 nucleotides in length; or 5 nucleotides in length.

11. The agent of claim 8, wherein the 3'-wing segment is 1 to 6 nucleotides in length; 2 nucleotides in length; 3 nucleotides in length; 4 nucleotides in length; or 5 nucleotides in length.

12. The agent of claim 8, wherein the gap segment is 5 to 14 nucleotides in length; or 10 nucleotides in length.

13. The agent of claim 1, wherein the agent further comprises a ligand.

14. The agent of claim 13, wherein the antisense polynucleotide agent is conjugated to the ligand at the 3'-terminus.

15. The agent of claim 13, wherein the ligand is an N-acetylgalactosamine (GalNAc) derivative.

16. The agent of claim 15, wherein the ligand is

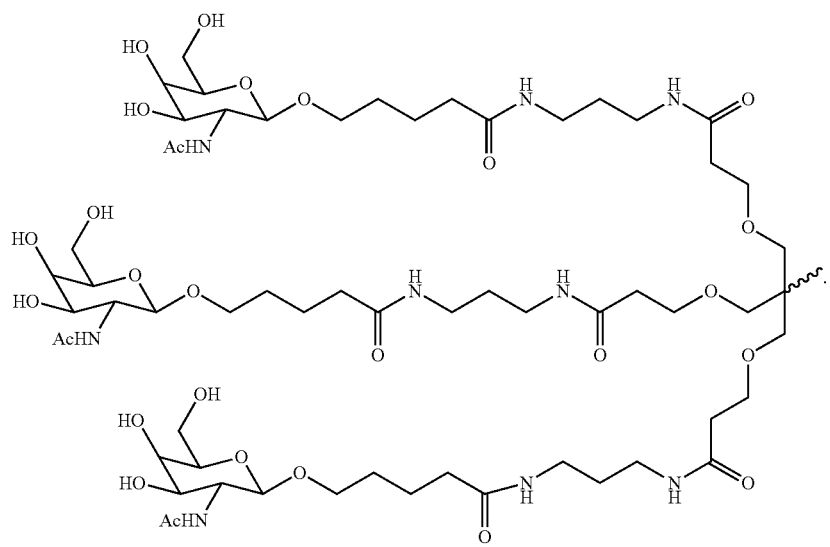 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

17. A pharmaceutical composition for inhibiting expression of a Factor XII gene, comprising the agent of claim 1.

18. A method of inhibiting expression of a Factor XII (F12) gene in a cell, the method comprising:
  (a) contacting the cell with the agent of claim 1; and
  (b) maintaining the cell produced in step (a) for a time sufficient to obtain antisense inhibition of a Factor XII (F12) gene, thereby inhibiting expression of the Factor XII gene in the cell.

* * * * *